US012790364B2

(12) United States Patent
Covey et al.

(10) Patent No.: US 12,790,364 B2
(45) Date of Patent: Nov. 10, 2026

(54) NMDAR INHIBITING AGENTS AND GABAAR POTENTIATING AGENTS AND USES THEREOF

(71) Applicant: Washington University, St. Louis, MO (US)

(72) Inventors: Douglas Covey, St. Louis, MO (US); Steven Mennerick, St. Louis, MO (US)

(73) Assignee: Washington University, St. Louis, MO (US)

( * ) Notice: Subject to any disclaimer, the term of this patent is extended or adjusted under 35 U.S.C. 154(b) by 1025 days.

(21) Appl. No.: 17/771,718

(22) PCT Filed: Oct. 16, 2020

(86) PCT No.: PCT/US2020/056171
§ 371 (c)(1),
(2) Date: Apr. 25, 2022

(87) PCT Pub. No.: WO2021/080880
PCT Pub. Date: Apr. 29, 2021

(65) Prior Publication Data
US 2022/0396597 A1 Dec. 15, 2022

Related U.S. Application Data

(60) Provisional application No. 63/051,713, filed on Jul. 14, 2020, provisional application No. 62/926,144, filed on Oct. 25, 2019.

(51) Int. Cl.
*C07J 31/00* (2006.01)
*C07J 1/00* (2006.01)
*C07J 13/00* (2006.01)

(52) U.S. Cl.
CPC ........... *C07J 31/006* (2013.01); *C07J 1/0003* (2013.01); *C07J 13/007* (2013.01)

(58) Field of Classification Search
CPC ...... C07J 31/006; C07J 1/0003; C07J 13/007; C07J 1/0011; C07J 7/0095; C07J 9/00; C07J 9/005; C07J 51/00; A61P 35/00
See application file for complete search history.

(56) References Cited

U.S. PATENT DOCUMENTS 8,796,249 B2 8/2014 Pellicciari
2003/0108583 A1 6/2003 Li
2006/0111333 A1 5/2006 Sorensen

FOREIGN PATENT DOCUMENTS

CN 107973834 A 5/2018
WO 1998003207 A1 1/1998
(Continued)

OTHER PUBLICATIONS

Gong et al., Synlett 2010, No. 3, 480-482. (Year: 2010).*
(Continued)

*Primary Examiner* — George W Kosturko
*Assistant Examiner* — Izabela Schmidt
(74) *Attorney, Agent, or Firm* — Stinson LLP

(57) ABSTRACT

N-methyl-d-aspartate receptors (NMDAR) and/or potentiating y-aminobutyric acid receptors (GABAAR) agents and uses thereof are described. Uses of these agents include methods of treating or preventing various psychiatric diseases, disorders, or conditions and methods of treating or preventing alcohol use disorder in a subject in need thereof.

7 Claims, 44 Drawing Sheets

(56) References Cited

FOREIGN PATENT DOCUMENTS

| | | | | |
|---|---|---|---|---|
| WO | 2006055009 A1 | 5/2006 | | |
| WO | 2009032321 A2 | 3/2009 | | |
| WO | 2010014836 A1 | 2/2010 | | |
| WO | 2015133776 A1 | 9/2015 | | |
| WO | WO-2015181275 A1 * | 12/2015 | ........... | A61K 31/575 |
| WO | 2017062763 A1 | 4/2017 | | |
| WO | WO-2018075699 A1 * | 4/2018 | ........... | A61K 31/575 |

OTHER PUBLICATIONS

STN, CAS registry No. 947296-80-2 (CAS registry No. 947296-80-2, entered to STN Sep. 14, 2007. (Year: 2007).*
STN, RN: 111900-81-3, Entered to STN Dec. 19, 1987. (Year: 1987).*
M. Wilpart, p. Mainguet, A. Maskens, M. Roberfroid, Structure-activity relationship amongst biliary acids showing co-mutagenic activity towards 1,2-dimethylhydrazine, Carcinogenesis, vol. 4, Issue 10, Oct. 1983, pp. 1239-1241 (Year: 1983).*
STN, RN: 2276-93-9, Entered to STN Nov. 16, 1984. (Year: 1984).*
Adam Bisaga et al., Exp. Opin. Invest. Drugs (2000) 9(10):2233-2248. (Year: 2000).*
Förstera B, et al., (2016) Front. Cell. Neurosci. 10:114. (Year: 2016).*
Gandal, et al., Transl Psychiatry 2, e142, (2012). (Year: 2012).*
Abdallah et al., “The Neurobiology of Depression, Ketamine and Rapid-Acting Antidepressants: Is It Glutamate Inhibition or Activation?,” Pharmacol Ther., 190:148-158, Oct. 2018.
Abrahao et al. “Alcohol and the Brain: Neuronal Molecular Targets, Synapses, and Circuits,” Neuron 96:1223-1238, Dec. 2017.
Adhikari et al., “Factors Affecting Enhanced Permeation of Amphotericin B Across Cell Membranes and Safety of Formulation,” AAPS PharmSciTech., 17(4):820-828, Aug. 2016.
Anderson et al., “Comparative Studies of ‘Bile Salts’,” Biochem J., 93(1): 34-39, Oct. 1964.
Anderson et al., “A More Detailed Study of Bile Salt Evolution, Including Techniques for Small-Scale Identification and their Application to Amphibian Biles” Biochem J., 141(2):485-494, Aug. 1974.
Baker et al., “Electrographic Responses to Intrahippocampal Injections of Convulsant Drugs,” Exp. Neurol. 12(2):136-145, Jun. 1965.
Belelli et al., “Realising the Therapeutic Potential of Neuroactive Steroid Modulators of the GABAA Receptor,” Neurobiol Stress, 12:100207, Dec. 2019.
Brant et al., “Biosynthesis and Release of Pheromonal Bile Salts In Mature Male Sea Lamprey,” BMC Biochem., 14:30, Nov. 2013.
Brown et al., “Pharmacological Characterization of a Novel Cell Line Expressing Human $\alpha4\beta3\delta$ GABAA Receptors,” Br J Pharmacol. 136(7):965-974, Aug. 2022.
Buchinger et al., “Evidence for a Receiver Bias Underlying Female Preference for a Male Mating Pheromone in Sea Lamprey,” Proc. Royal Soc. B, 280(1771):20131966, Sep. 2013.
Burns et al., “Synthesis and olfactory activity of unnatural, sulfated 5β-bile acid derivatives in the sea lamprey (Petromyzon marinus),” Steroids, 76(3):291-300, Feb. 2011.
Cai et al., “Adult sea lamprey tolerates biliary atresia by altering bile salt composition and renal excretion,” Hepatology, 57(6):2418-2426, Jun. 2013.
Chisari et al., “Structurally Diverse Amphiphiles Exhibit Biphasic Modulation of GABAA Receptors: Similarities and Differences With Neurosteroid Actions,” Br. J. Pharmacol. 160:130-141, May 2010.
Chisari et al., “Visualizing Pregnenolone Sulfate-Like Modulators of NMDA Receptor Function Reveals Intracellular and Plasma-Membrane Localization,” Neuropharmacology 144:91-103, Jan. 2019.
Chung-Davidson et al., “Pheromonal bile acid 3-ketopetromyzonol sulfate primes the neuroendocrine system in sea lamprey,” BMC Neurosci., 14:11, Jan. 2013.
Chung-Davidson et al., “Hsp90 and hepatobiliary transformation during sea lamprey metamorphosis,” BMC Dev Biol. 15:47, Dec. 2015.
Chung-Davidson et al., “Pheromone 3kPZS evokes context-dependent serotonin sexual dimorphism in the brain of the sea lamprey (Petromyzon marinus),” Integr Zool. 10(1):91-101, Jan. 2015.
Covey et al. “Recent Developments in Structure-Activity Relationships for Steroid Modulators of GABAA Receptors,” Brain Res Brain Res Rev. 37(1-3):91-97, Nov. 2011.
D’More et al., “Design, Synthesis, and Biological Evaluation of Potent Dual Agonists of Nuclear and Membrane Bile Acid Receptors,” J. Med. Chem., 57(3):937-954, Jan. 2014.
Duman et al., “Neurobiology of Rapid-Acting Antidepressants: Convergent Effects on GluA1-Synaptic Function,” Mol Psychiatry, 24(12):1816-1832, Dec. 2019.
Eisenman et al., “Activation-Dependent Properties of Pregnenolone Sulfate Inhibition of GABAA Receptor-Mediated Current,” J Physiol., 550(Pt 3): 679-691, Aug. 2003.
Ekins et al., “Challenges Predicting Ligand-Receptor Interactions of Promiscuous Proteins: The Nuclear Receptor PXR,” PLoS Comput Biol., 5(12): e1000594, Dec. 2009.
Emnett et al., “Interaction Between Positive Allosteric Modulators and Trapping Blockers of the NMDA Receptor Channel,” Br. J. Pharmacol., 172(5):1333-1347, Mar. 2015.
Eyssen et al., “Sulfated Bile Acids in Germ-Free and Conventional Mice,” Eur J Biochem., 66(3):507-514, Jul. 1976.
Festa et al., “Exploitation of Cholane Scaffold for the Discovery of Potent and Selective Farnesoid X Receptor (FXR) and G-Protein Coupled Bile Acid Receptor 1 (GP-BAR1) Ligands,” J. Med. Chem., 57(20):8477-8495, Sep. 2014.
Fine et al., “Evidence That Petromyzontid Lampreys Employ a Common Migratory Pheromone That Is Partially Comprised of Bile Acids,” J Chem Ecol., 30(11):2091-2110, Nov. 2004.
Fine et al., “Biologically Relevant Concentrations of Petromyzonol Sulfate, a Component of the Sea Lamprey Migratory Pheromone, Measured in Stream Water,” J Chem Ecol., 31(9):2205-2210, Sep. 2005.
Fine et al., “Isolation and Biological Activity of the Multi-Component Sea Lamprey Migratory Pheromone,” J Chem Ecol., 34(10):1259-1267, Oct. 2008.
Fine et al., “Production and fate of the sea lamprey migratory pheromone,” Fish Physiol Biochem., 36(4):1013-1020, Dec. 2010.
Flynn et al., “Correlation and Prediction of Mass Transport across Membranes I: Influence of Alkyl Chain Length on Flux-Determining Properties of Barrier and Diffusant,” J Pharm Sci., 61(6):838-852, Jun. 1972.
Gangadhar et al., “Synthesis and Evaluation of Sodium Deoxycholate Sulfate as a Lipid Drug Carrier to Enhance the Solubility, Stability and Safety of an Amphotericin B Inhalation Formulation,” Int. J. Pharm.,471(1-2):430-438, Aug. 2014.
Gong et al. “Stereoselective Synthesis of Methyl Spongoate, a New Steroid with Potent Antitumor Activities,” Synlett, 2010(3):480-482, Feb. 2010.
Gunduz-Bruce et al., “Trial of SAGE-217 in Patients With Major Depressive Disorder,” N. Engl. J. Med. 381(10):903-911, Sep. 2019.
Hagey et al., “Diversity of Bile Salts in Fish and Amphibians: Evolution of a Complex Biochemical Pathway,” Physiol Biochem Zool., 83(2): 308-321, Mar.-Apr. 2010.
Hardingham et al., “Synaptic Versus Extrasynaptic NMDA Receptor Signalling: Implications for Neurodegenerative Disorders,” Nat Rev Neurosci., 11(10): 682-696, Oct. 2010.
Harrison et al., “A Steroid Anesthetic Prolongs Inhibitory Postsynaptic Currents in Cultured Rat Hippocampal Neurons,” J Neurosci., 7(2):604-609, Feb. 1987.
Haslewood, “Comparative Studies of ‘Bile Salts’,” Biochem J., 90(2): 309-313, Feb. 1964.
Haslewood, “Petromyzonol Sulphate, a Bile Salt of Lampreys,” Bio Chem J., 6P, 1967.
Haslewood, “Specificity and Some Characteristics of a 7A-Hydroxysteroid Dehydrogenase From *E. coli*,” Adv. Bile Acid Res., Bile Acid Meet., 3rd, pp. 105-107, 1975.

(56) References Cited

OTHER PUBLICATIONS

Iaslewood, "The Specificity of a 7a-Hydroxy Steroid Dehydrogenase from *Escherichia* coil," Biochem. J., 157(1):207-210, Jul. 1976.
Honorio et al., "Hologram Qsar Studies on Farnesoid X Receptor Activators," Lett Drug Des Discov., 3(4):261-267, 2006.
Horak et al., "Subtype-Dependence of N-Methyl-D-Aspartate Receptor Modulation by Pregnenolone Sulfate," Neuroscience 137(1):93-102, Feb. 2006.
Horak et al., "Molecular Mechanism of Pregnenolone Sulfate Action at NR1/NR2B Receptors," J. Neurosci., 24(46):10318-10325, Nov. 2004.
Hosie et al., "Endogenous Neurosteroids Regulate GABAA Receptors via Two Discrete Transmembrane Sites," Nature 444:486-489, Nov. 2006.
Hosie et al., "Neurosteroid Binding Sites on GABA(A) Receptors," Pharmacol Ther., 116(1):7-19, Oct. 2007.
Hoye et al., "Details of the Structure Determination of the Sulfated Steroids PSDS and PADS: New Components of the Sea Lamprey (Petromyzon marinus) Migratory Pheromone," J. Org. Chem. 72(20):7544-50, Oct. 2007.
Hu et al., "The Major Cholesterol Metabolite Cholestane-3beta, 5alpha, 6beta-Triol Functions as an Endogenous Neuroprotectant," J. Neurosci., 34:11426-11438, Aug. 2014.
Ishizawa et al., "Lithocholic acid derivatives act as selective vitamin D receptor modulators without inducing hypercalcemia," J Lipid Res., 49(4):763-772, Apr. 2008.
Johnson et al., "Recent Insights Into the Mode of Action of Memantine and Ketamine," Curr Opin Pharmacol., 20:54-63, Feb. 2015.
Kanes et al., "Brexanolone (SAGE-547 Injection) in Post-Partum Depression: A Randomised Controlled Trial," Lancet 390:480-489, Jul. 2017.
Korinek et al., "Neurosteroid Modulation of N-Methyl-D-Aspartate Receptors: Molecular Mechanism and Behavioral Effects," Steroids, 76(13):1409-1418, Dec. 2011.
Krasowski et al., "Evolution of the Pregnane X Receptor: Adaptation to Cross-Species Differences in Biliary Bile Salts," Mol Endocrinol., 19(7):1720-2739, Jul. 2005.
Kufahl et al., "The Development of Acamprosate as a Treatment Against Alcohol Relapse," Expert Opin. Drug Discov., 9(11):1355-1369, Nov. 2014.
Li et al., "Highly Independent Olfactory Receptor Sites for Naturally Occurring Bile Acids in the Sea Lamprey, Petromyzon Marinus," J. Comp. Physiol., 180(4):429-438, Mar. 1997.
Li et al., "Multiplex Quantification of Lamprey Specific Bile Acid Derivatives in Environmental Water Using Uhplc-Ms/MS," J Chromatogr B., 15;879(32):3879-86, Dec. 2011.
Li et al., "Isolation and Identification of Petromyzestrosterol, a Polyhydroxysteroid From Sexually Mature Male Sea Lamprey (*Petromyzon marinus* L.)," Steroids, 77(7):806-810, Jun. 2012.
Li et al., "Characterization of a Novel Bile Alcohol Sulfate Released by Sexually Mature Male Sea Lamprey (Petromyzon marinus)," PLoS One, 8(7):e68157, Jul. 2013.
Linsenbardt et al., "Different Oxysterols Have Opposing Actions at N-Methyl-D-Aspartate Receptors," Neuropharmacol., 85:232-242, Oct. 2014.
Lipinski, "Drug-like properties and the causes of poor solubility and poor permeability," J Pharmacol Toxicol Methods, 44(1):235-249, Jul.-Aug. 2000.
MacDonald et al., "Use-Dependent Block of Excitatory Amino Acid Currents in Cultured Neurons by Ketamine," J. Neurophysiol., 58(2):251-266, Aug. 1987.
Madhumanchi et al., "Binding Interactions of Bacterial Lipopolysaccharides to Polymyxin-B Antibiotic in an Amphiphilic Carrier 'Sodium Deoxycholate Sulfate'," The 11th IMT-GT UNINET Conference 2018—Bioscience for a Sustainable Future, Dec. 2018, 1pg.
Malayev et al., "Inhibition of the NMDA Response by Pregnenolone Sulphate Reveals Subtype Selective Modulation of NMDA Receptors by Sulphated Steroids," Br J Pharmacol., 135(4):901-909, Feb. 2000.
Meckley et al., "Field Evaluation of Larval Odor and Mixtures of Synthetic Pheromone Components for Attracting Migrating Sea Lampreys in Rivers," J Chem Ecol. 38(8):1062-1069, Aug. 2012.
Meltzer-Brody et al., "Brexanolone Injection in Post-Partum Depression: Two Multicentre, Double-Blind, Randomised, Placebo- Controlled, Phase 3 Trials," Lancet, 39(2):1058-1070, Jun. 2019.
Meltzer-Brody et al., "Allopregnanolone in Postpartum Depression: Role in Pathophysiology and Treatment," Neurobiol Stress, 12:100212, Feb. 2020.
Mennerick et al., "Effects on γ-Aminobutyric Acid GABAA Receptors of a Neuroactive Steroid That Negatively Modulates Glutamate Neurotransmission and Augments GABA Neurotransmission," Mol. Pharmacol., 60(4):732-741, Oct. 2001.
Miller et al., "GluN2B-Containing NMDA Receptors Regulate Depression-Like Behavior and Are Critical for the Rapid Antidepressant Actions of Ketamine," Elife, 3:e03581, Oct. 2014.
Nilsson et al., "Neurosteroid analogues. 6. The Synthesis and GABAA Receptor Pharmacology of Enantiomers of Dehydroepiandrosterone Sulfate, Pregnenolone Sulfate, and (3a, 5b)-3-Hydroxypregnan-20-One Sulfate," J Med Chem., 41(14):2604-2613, Jul. 1998.
Park-Chung et al., "Distinct Sites for Inverse Modulation of N-Methyl-D-Aspartate Receptors by Sulfated Steroids," Mol Pharmacol., 52(6):1113-1123, Dec. 1997.
Parsons et al., "Patch Clamp Studies on the Kinetics and Selectivity of N-Methyl-D-Aspartate Receptor Antagonism by Memantine (1-Amino-3,5-Dimethyladamantan)," Neuropharmacology, 32(12):1337-1350, Dec. 1993.
Paul et al., "The Major Brain Cholesterol Metabolite 24(S)-Hydroxycholesterol Is a Potent Allosteric Modulator of N-Methyl-D-Aspartate Receptors," J. Neurosci., 33(44):17290-17300, Oct. 2013.
Pellicciari et al., "Bile Acid Derivatives as Ligands of the Farnesoid X Receptor. Synthesis, Evaluation, and Structure-Activity Relationship of a Series of Body and Side Chain Modified Analogues of Chenodeoxycholic Acid," J Med Chem., 47(18):4559-4569, Aug. 2004.
Petrovic et al., "20-Oxo-5β-Pregnan-3α:-Yl Sulfate Is a Use-Dependent NMDA Receptor Inhibitor," J. Neurosci., 25(37):8439-8450, Sep. 2005.
Polkinghorne et al., "Larval Sea Lamprey Release Two Unique Bile Acids to the Water at a Rate Sufficient to Produce Detectable Riverine Pheromone Plumes," Fish Physiol. Biochem., 24:15-30, Jan. 2001.
Reschly et al., "Functional evolution of the vitamin D and pregnane X receptors," BMC Evol Biol., 7:222, Nov. 2007.
Reschly et al., "Ligand specificity and evolution of liver X receptors," J Steroid Biochem Mol Biol., 110(1-2):83-94, May 2008.
Robinson, "Olfactory Sensitivity of Pacific Lampreys to Lamprey Bile Acids," Trans Am Fish Soc., 138(1):144-152, Jan. 2009.
Sato et al., "Novel, Major 2a-and 2b-Hydroxy Bile Alcohols and Bile Acids in the Bile of Arapaima gigas, a Large South American River Fish," Steroids, 107:112-120, Mar. 2016.
Schubring et al., "The Bile Steroid Chenodeoxycholate Is a Potent Antagonist at NMDA and GABA a Receptors," Neurosci. Lett., 506(2):322-326, Jan. 2012.
Shimizu et al., "Hypocholesterolemic Effect of 5B-Cholane-3A,7B,24-Triol-24-Sulfate in Hamsters," Biol Pharm Bull., 18(1):28-32, Jan. 1995.
Siefkes et al., "Electrophysiological evidence for detection and discrimination of pheromonal bile acids by the olfactory epithelium of female sea lampreys (Petromyzon marinus)," J Comp Physiol A Neuroethol Sens Neural Behav Physiol., 190(3):193-199, Mar. 2004.
Smith et al., "APA Role for Picomolar Concentrations of Pregnenolone Sulfate in Synaptic Activity-Dependent Ca2+ Signaling and CREB Activation," Mol Pharmacol., 86:390-398, Oct. 2014.
Song et al., "A Novel Sterol Sulfate and New Oligosaccharide Polyester from the Aerial Parts of Polygala sibirica," Nat Prod Commun., 7(9):1165-1168, Sep. 2012.
Sorensen et al, "Mixture of new sulfated steroids functions as a migratory pheromone in the sea lamprey," Nat Chem Biol., 1(6):324-328, Nov. 2005.

(56) References Cited

OTHER PUBLICATIONS

Sorensen et al, "A Critical Review of the Discovery and Application of a Migratory Pheromone in an Invasive Fish, the Sea Lamprey *Petromyzon marinus* L.," J. Fish Biol., 71(sd):100-114, Dec. 2007.
Sorensen et al, "A Multi-Component Migratory Pheromone in the Sea Lamprey," Fish Physiol. Biochem., 28:253-257, Mar. 2003.
Sorensen et al, "The Chemical Ecology and Potential Application of the Sea Lamprey Migratory Pheromone," J. Great Lakes Res., 29(Suppl. 1):66-84, Dec. 2003.
Stewart et al., "A Rapid, Sensitive, and Selective Method for Quantitation of Lamprey Migratory Pheromones in River Water," J Chem Ecol., 37(11):1203-1207, Nov. 2011.
Stewart et al., "A Sensitive Analytical Method for Quantifying Petromyzonol Sulfate in Water as a Potential Tool for Population Monitoring of the Southern Pouched Lamprey, Geotria Australis, in New Zealand Streams," J Chem Ecol., 38(2):135-144, Feb. 2012.
Stewart et al., "Chemical Analysis of Aquatic Pheromones in Fish," Methods Mol Biol., 1068:55-69, Sep. 2013.
Teague et al., "The Design of Leadlike Combinatorial Libraries," Angew Chem Int Ed Engl., 38(24):3743-3748, Dec. 1999.
Usman et al., "Pharmacologically Safe Nanomicelles of Amphotericin B With Lipids: Nuclear Magnetic Resonance and Molecular Docking Approach," J. Pharm. Sci., 106(12):3574-3582, Aug. 2017.
Venkatachalam et al., "Isolation, partial purification, and characterization of a novel petromyzonol sulfotransferase from Petromyzon marinus (lamprey) larval liver," J Lipid Res., 45(3):486-495 , Mar. 2004.
Walaszczyk et al., "Differential Effects of Sex Pheromone Compounds on Adult Female Sea Lamprey (Petromyzon marinus) Locomotor Patterns," J Biol Rhythms, 31(3):289-298, Jun. 2016.
Wang et al., "Hydroxypregnane Steroids Are Pregnenolone Sulfate-Like GABAA Receptor Antagonists," J. Neurosci., 22(9):3366-3375, May 2002.
Wang et al., "Monitoring Sea Lamprey Pheromones and Their Degradation Using Rapid Stream-Side Extraction Coupled With Uplc-Ms/MS," J Sep Sci.,36(9-10):1612-1620, May 2013.
Wang et al., "An UPLC-MS/MS Method for Quantitative Profiling of Bile Acids in Sea Lamprey Plasma and Tissues," J Chromatogr B Analyt Technol Biomed Life Sci., 980:72-78, Feb. 2015.
Weaver et al., "Geometry and Charge Determine Pharmacological Effects of Steroids on N-Methyl-D-Aspartate Receptor-Induced Ca(2+) Accumulation and Cell Death," J. Pharmacol. Exp. Ther., 293:747-754, Jun. 2000.
Weiming et al., "The Olfactory System of Migratory Adult Sea Lamprey (Petromyzon marinus) Is Specifically and Acutely Sensitive to Unique Bile Acids Released by Conspecific Larvae," J Gen Physiol., 105(5):569-587, May 1995.
Williams et al., "NMDA Antagonist Treatment of Depression," Curr. Opin. Neurobiol., 36:112-117, Feb. 2016.
Yao et al., "Nontargeted Analysis of the Urine Nonpolar Sulfateome: A Pathway to the Nonpolar Xenobiotic Exposome," Rapid Commun Mass Spectrom., 30(21):2341-2350, Nov. 2016.
Yun et al., "Pheromones of the Male Sea Lamprey, *Petromyzon marinus* L.: Structural Studies on a New Compound, 3-Keto Allocholic Acid, and 3-Keto Petromyzonol Sulfate," Steroids, 68(3):297-304, Mar. 2003.
Yun et al., "HPLC and ELISA Hplc and Elisa Analyses of Larval Bile Acids From Pacific and Western Brook Lampreys," Steroids, 68(6):515-523, Aug. 2003.
Yun, "Comparative Studies of Bile Acid Release in the Mature Male Lampreys," Fish Aquat Sci., 15(1):63-67, Mar. 2012.
Yun et al., "Sulfated Bile Acids as Putative Sex Pheromone Components in Pacific Lamprey," Trans. Am. Fish. Soc., 143(6):1455-1459, Oct. 2014.
Zanos et al., "Mechanisms of Ketamine Action as an Antidepressant," Mol. Psychiatry, 23(4):801-811, Apr. 2018.
Zhang et al., "Lake Char (Salvelinus Namaycush) Olfactory Neurons Are Highly Sensitive and Specific to Bile Acids," J Comp Physiol A Neuroethol Sens Neural Behav Physiol., 195(2):203-215, Feb. 2009.
Zielinski et al., "Morphological and Electrophysiological Examination of Olfactory Sensory Neurons During the Early Developmental Prolarval Stage of the Sea Lamprey *Petromyzon marinus* L," J Neurocytol., 34(3-5):209-216, Sep. 2005.
Zorumski et al., "NMDA receptors and beyond," J. Neurosci., 36(44):11158-11164, Nov. 2016.
International Preliminary Report on Patentability of the International Bureau of WIPO in PCT/US2020/056171, dated May 5, 2022; 8pgs.
International Search Report and Written Opinion of the ISA/US in PCT/US2020/056171, dated Feb. 26, 2021; 11pgs.
PubChem Compound Summary—Isoursodeoxyholic acid I C24H40O4; PubChem CID 127601; Dec. 14, 2020; 3pgs.
PubChem Compound Summary—[(4R)-4-[(3R,5R,8R,9S,10S,13R,14S,17R)-3-Hydroxy-10,13-dimethyl-2,3,4,5,6,7,8,9,11,12,14,15,16,17-tetradecahydro-1H-cyclopenta[a]phenanthren-17-yl]pentyl] hydrogen sulfate; PubChem CID 51034056; Dec. 14, 2020; 6pgs.
Irwin et al., "ZINC—A Free Database of Commercially Available Compounds for Virtual Screening," J Chem Inf Model., 45(1):177-182, Jan.-Feb. 2005.
Haslewood, "Comparative Biochemistry of Bile Salts," Biliary System, Symp. NATO Advan. Study Inst., Newcastle-upon-Tyne, Engl. (1965), 1963, 107-15, discussion 115-16.

* cited by examiner

A

C

E

D

NMDAR INHIBITING AGENTS AND GABAAR POTENTIATING AGENTS AND USES THEREOF

STATEMENT REGARDING FEDERALLY SPONSORED RESEARCH OR DEVELOPMENT

This invention was made with government support under MH110550 awarded by the National Institutes of Health. The government has certain rights in the invention.

FIELD OF THE INVENTION

The present disclosure generally relates to N-methyl-d-aspartate receptors (NMDAR) and/or potentiating γ-aminobutyric acid receptors (GABAAR) agents and uses thereof are described. Uses of these agents include methods of treating or preventing various psychiatric diseases, disorders, or conditions and methods of treating or preventing alcohol use disorder in a subject in need thereof.

BACKGROUND

Neuroactive steroids are a class of compounds that are emerging as potentially efficacious for treating neuropsychiatric disorders. Neuroactive steroids and ketamine are two classes of compounds that possess rapid antidepressant action and may be useful when conventional antidepressants fail (Abdallah et al., 2018; Duman et al., 2019; Gunduz-Bruce et al., 2019; Kanes et al., 2017; Meltzer-Brody et al., 2018; Meltzer-Brody and Kanes, 2020; Zanos and Gould, 2018). Neurosteroids and synthetic neuroactive steroids in clinical development primarily act as positive allosteric modulators (PAMS) of $GABA_A$ receptors ($GABA_A$Rs). These compounds prolong IPSCs and augment tonic current at $GABA_A$Rs (Belelli et al., 2020). In contrast, ketamine is an NMDAR antagonist (MacDonald et al., 1987). Although the relevance of $GABA_A$R potentiation and NMDAR antagonism to therapeutic, anti-depressant benefit are still under active investigation, compounds with dual actions at $GABA_A$Rs and NMDA receptors could be particularly effective antidepressants. In addition, drugs with dual actions at both of these receptor classes, such as acamprosate, are of interest in alcohol use disorder (Kufahl et al., 2014). Thus, combined $GABA_A$R PAM and NMDAR negative allosteric modulator (NAM) effects may have high clinical applicability.

Brexanolone is a formulation of allopregnanolone, an endogenous neurosteroid, and is FDA approved for treatment of postpartum depression. Allopregnanolone is representative of neurosteroids and their analogues that are 3α-hydroxy neurosteroids. This 3α-hydroxyl group appears to be requisite for strong $GABA_A$R PAM action (Covey et al., 2001). However, 3α-hydroxysteroids are typically ineffective at NMDARs.

Sulfated neurosteroids, such as pregnenolone sulfate and pregnanolone sulfate, modulate both $GABA_A$Rs and NMDARs. These steroids can be either NMDAR PAMs or NAMs, depending on NMDAR subunit composition and neurosteroid structure (Horak et al., 2006; Korinek et al., 2011; Malayev et al., 2002; Park-Chung et al., 1997). Although the mechanisms of NMDAR modulation have not been fully elucidated, inhibition by some sulfated neurosteroids, including pregnanolone sulfate, is dependent on channel activation (Petrovic et al., 2005). The actions of sulfated neurosteroids on NMDARs are typically not very potent compared with $GABA_A$R actions of either 3α-hydroxy neurosteroids or sulfated neurosteroids. Further, sulfated steroids inhibit, rather than augment, $GABA_A$R function. The structural requirements for this inhibition are quite diverse: the enantiomer of pregnenolone sulfate is an effective NAM (Nilsson et al., 1998); the position of the negatively charged group can vary with little impact on inhibition (Mennerick et al., 2001; Schubring et al., 2012); and a wide variety of negatively charged amphiphiles inhibit $GABA_A$R function by a similar mechanism (Chisari et al., 2010).

Further, there is large unmet clinical need for medications to treat alcohol use disorder (AUD), which takes a very high personal and public health toll in the United States and worldwide. Medications remain underdeveloped. Only three drugs are FDA approved to treat AUD: disulfiram (Antabuse), acamprosate (Campral), and naltrexone (Revia, Vivitrol). Disulfiram works by inhibiting acetaldehyde dehydrogenase, causing nausea in patients who drink, and it outperforms placebo only when the study is open label rather than blinded, suggesting that psychological threat may provide most of the benefit. Acamprosate is modestly efficacious in patients and is the only drug of the three that mainly works by reducing craving in abstinent patients. It appears somewhat more effective in patients than naltrexone, based on meta-analysis of aggregated abstinence measures. However, the efficacy of acamprosate has been called into question. Therefore, there remains a critical need for medications to treat alcohol use disorder (AUD).

SUMMARY OF THE INVENTION

Aspects of the present invention are directed to various compounds that are useful as NMDAR inhibiting and/or $GABA_A$R potentiating agents. These compounds include those of formula (I) and pharmaceutically acceptable salts thereof:

(I)

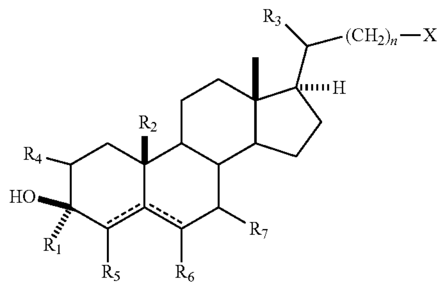

wherein:

$R_1$ is hydrogen, $C_1$ to $C_6$ alkyl, $C_1$ to $C_6$ alkenyl, $C_1$ to $C_6$ alkynyl, $C_1$ to $C_6$ alkoxy, or $C_1$ to $C_6$ haloalkyl;

$R_2$ is hydrogen, $C_1$ to $C_6$ alkyl, $C_1$ to $C_6$ alkenyl, $C_1$ to $C_6$ alkynyl, $C_1$ to $C_6$ alkoxy, $C_1$ to $C_6$ haloalkyl, $-CH_2O-R_A$, or $-CH_2O(C{=}O)-R_B$;

$R_3$ is hydrogen, $C_1$ to $C_6$ alkyl, $C_1$ to $C_6$ alkenyl, $C_1$ to $C_6$ alkynyl, $C_1$ to $C_6$ haloalkyl, $-CH_2O-R_A$, or $-CH_2O(C{=}O)-R_B$;

each $R_A$ is independently $C_1$ to $C_6$ alkyl or $C_1$ to $C_6$ haloalkyl;

each $R_B$ is independently hydrogen, $C_1$ to $C_6$ alkyl, or $C_1$ to $C_6$ haloalkyl;

$R_4$ is hydrogen, hydroxy, $C_1$ to $C_6$ alkyl, $C_1$ to $C_6$ alkenyl, $C_1$ to $C_6$ alkynyl, $C_1$ to $C_6$ alkoxy, or $C_1$ to $C_6$ haloalkyl;

$R_5$ is hydrogen, hydroxy, $C_1$ to $C_6$ alkyl, $C_1$ to $C_6$ alkenyl, $C_1$ to $C_6$ alkynyl, $C_1$ to $C_6$ alkoxy, or $C_1$ to $C_6$ haloalkyl;

$R_6$ is hydrogen, hydroxy, $C_1$ to $C_6$ alkyl, $C_1$ to $C_6$ alkenyl, $C_1$ to $C_6$ alkynyl, $C_1$ to $C_6$ alkoxy, or $C_1$ to $C_6$ haloalkyl;

$R_7$ is hydrogen, hydroxy, $C_1$ to $C_6$ alkyl, $C_1$ to $C_6$ alkenyl, $C_1$ to $C_6$ alkynyl, $C_1$ to $C_6$ alkoxy, or $C_1$ to $C_6$ haloalkyl;

X is hydroxy, $OSO_3H$, $OSO_3^-NH_4^+$, $SO_3H$, $SO_2H$, COOH, $NH(CH_2)_m$—Y, $H_2PO_4$, $HPO_3R_8$, $C(R_9)_2COOH$, $C(R_9)_2$—Y, or other negatively charged group at physiological pH;

Y is $OSO_3H$, $SO_3H$, $SO_2H$, COOH, $H_2PO_4$, $HPO_3R_8$, or other negatively charged group at physiological pH;

each $R_8$ is independently hydrogen, $C_1$ to $C_6$ alkyl or $C_1$ to $C_6$ haloalkyl;

each $R_9$ is independently hydrogen, $C_1$ to $C_6$ alkyl, $C_1$ to $C_6$ haloalkyl, or halo;

m is an integer from 1 to 6; and n is an integer from 1 to 8.

In some embodiments, the compound of formula (I) has NMDA receptor inhibitory activity and/or $GABA_A$ receptor potentiation activity.

Aspects of the present disclosure also provide for a method of inhibiting N-methyl-d-aspartate receptors (NMDAR) and/or potentiating γ-aminobutyric acid receptors ($GABA_AR$). In some embodiments, the method comprises administering to a subject a composition comprising an effective amount of a compound of formula (I) or a pharmaceutically acceptable salt thereof.

In some embodiments, the subject has or is suspected of having a psychiatric disease, disorder, or condition. As such, various methods are for treating or preventing a psychiatric disease, disorder, or condition in a subject in need thereof. For example, the psychiatric disease, disorder, or condition is a depression related disease, major depressive disorder, or anxiety.

Further aspects relate to methods of treating or preventing alcohol use disorder in a subject in need thereof comprising administering to the subject a composition comprising an effective amount of a compound of formula (I) or a pharmaceutically acceptable salt thereof. In some embodiments, the compound has the following structure:

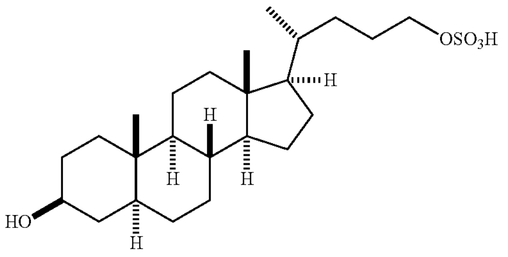

or pharmaceutically acceptable salt thereof.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

μM NMDA (A) and 100 μM (B). C, Steady-state inhibition by MQ-221 did not detectably differ between 5 μM and 100 μM NMDA ($t=0.1328$, $p=0.8964$, two-sample unpaired t test, ns). On the other hand, the time constant of both onset and offset of inhibition was accelerated at the high NMDA concentration (*$t=2.731$, $p=0.0171$, $n=6$; *$t=2.614$, $p=0.0214$, $n=9$ two sample unpaired t test). D, E. Sample traces showing responses to 20 μM NMDA in the absence (D) and presence (E) of 30 μM KK-169, and inhibition by 2.5 μM MQ-221. F. Summary of MQ-221 effect shows similar inhibition despite PAM presence but accelerated inhibition and offset time constants (**$t=16.85$, $p<0.0001$; $t=3.671$, $p<0.0079$ two sample paired t test, $n=8$).

Figure 8:
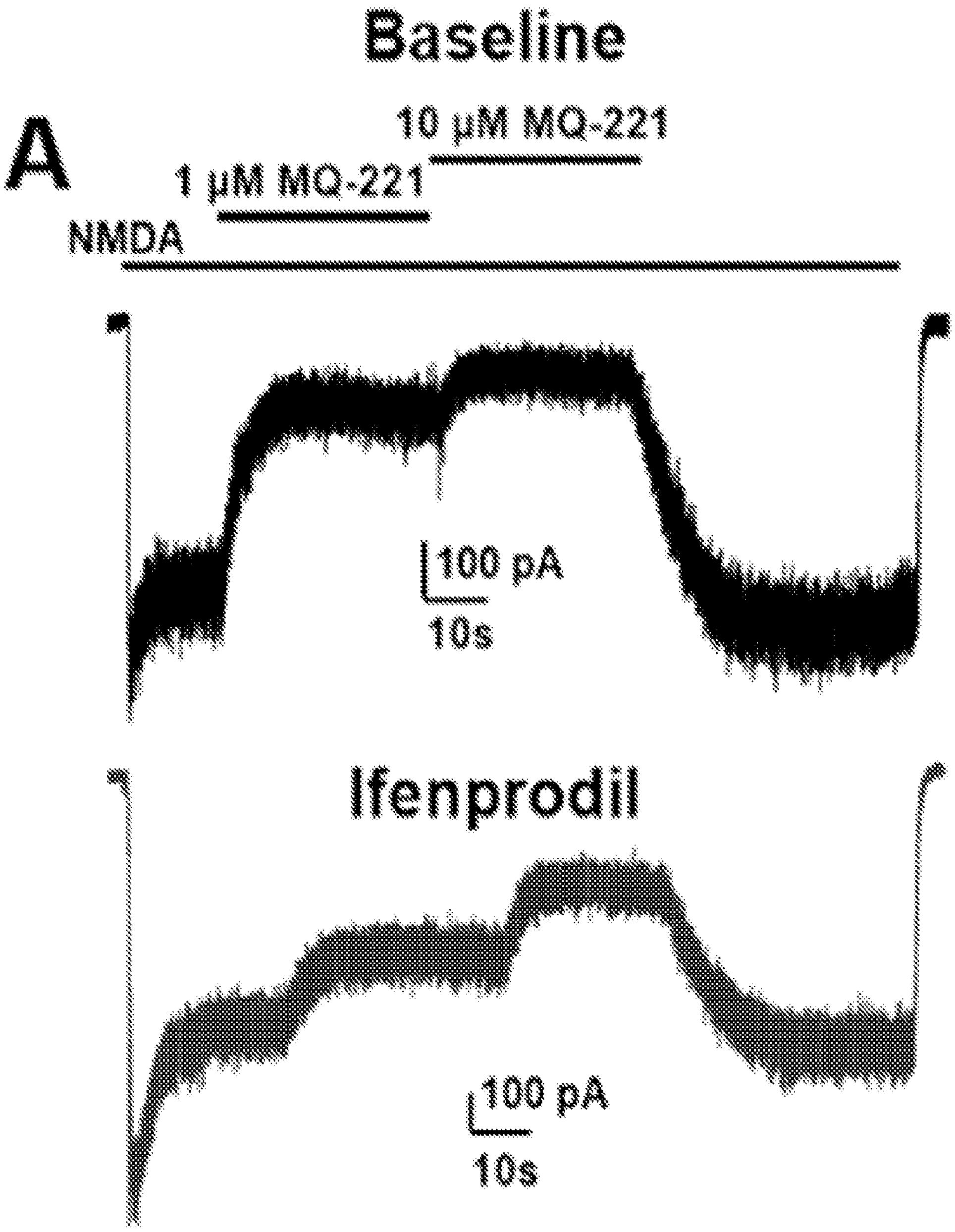
Figure 8:
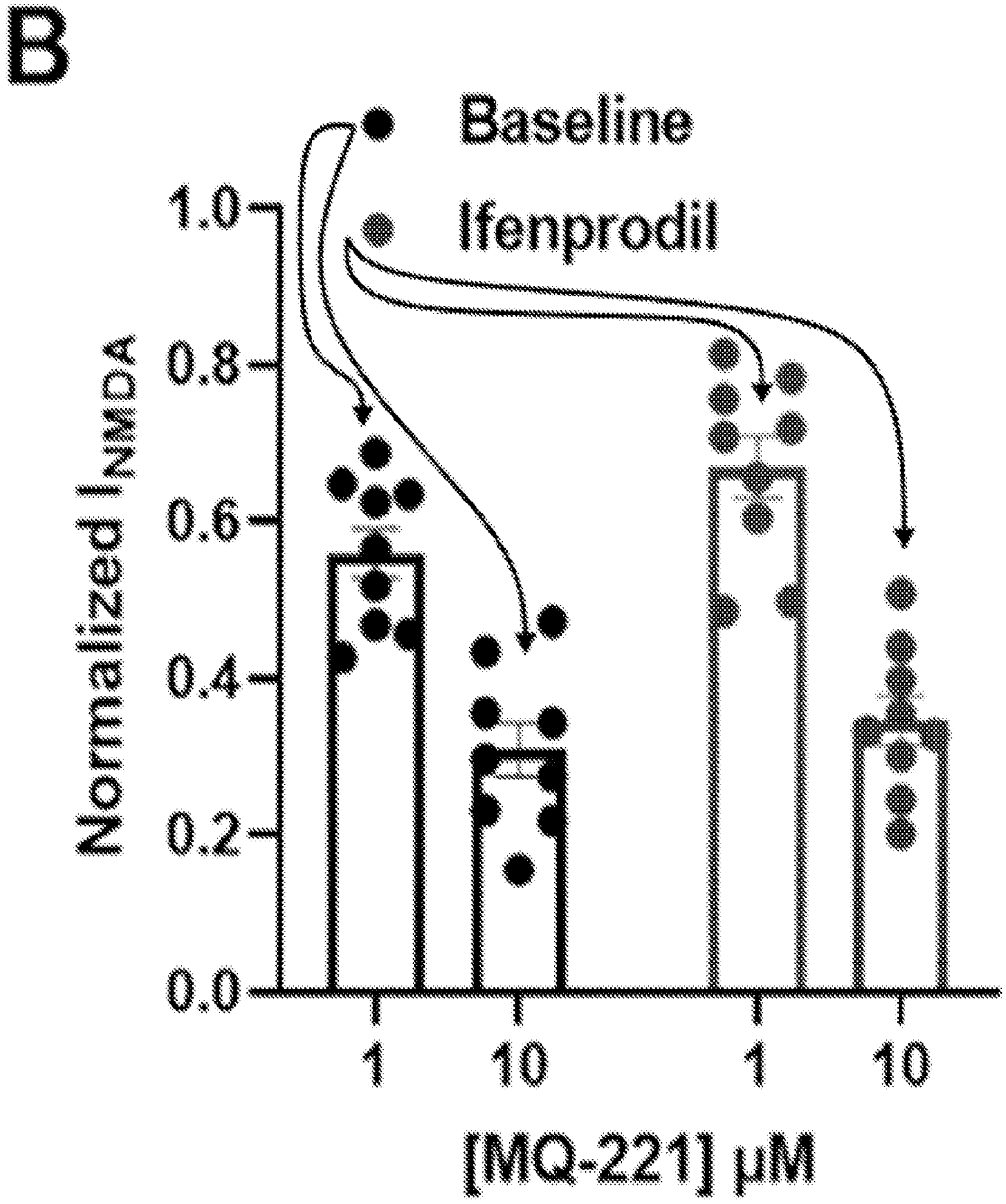
Figure 8:
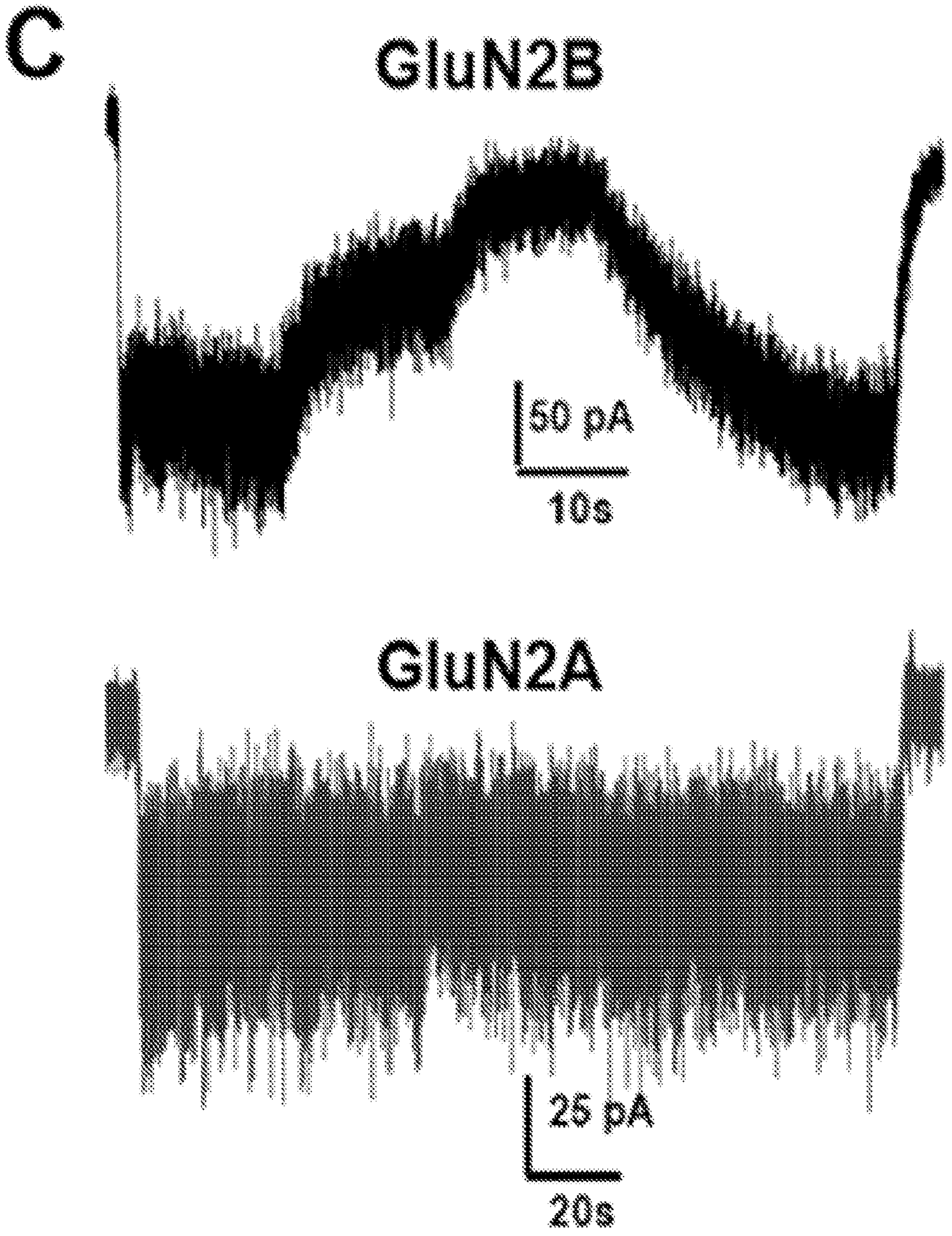
Figure 8:
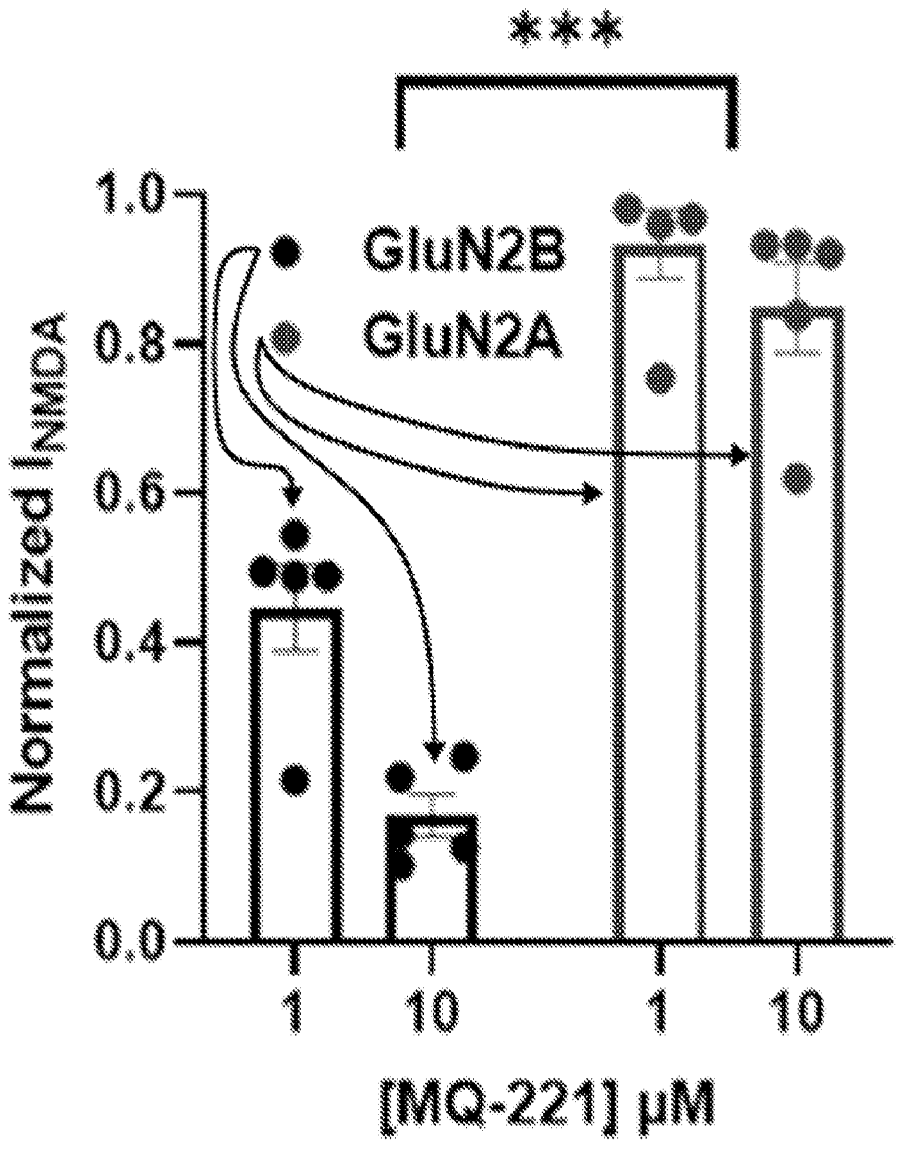

FIG. 8. Tests of GluN2A and GluN2B subunit selectivity. A, B. In hippocampal neurons, the inhibitory effect of MQ-221 at 2 concentrations was compared with the effect in the presence of 10 μM ifenprodil, which inhibits GluN2B-containing NMDARs. NMDA (10 μM) was used as agonist. A two-way ANOVA showed an interaction between drugs ($F(1, 16)=4.884$; $p=0.04$) and Sidak post hoc test suggested a differing response at 1 μM MQ-221 ($p=0.06$) that drives the interaction. C, D. N2a cells were transfected with GluN1a and either GluN2A or GluN2B subunits and challenged with the same protocol of NMDA and MQ-221 co-application. A two-way ANOVA showed a lower sensitivity of GluN2A-containing receptors to MQ-221 ($F(1, 8)=83.98$; $p<0.001$). Application bars above baseline trace in panel A apply to all traces in panels A and C.

Figure 9:
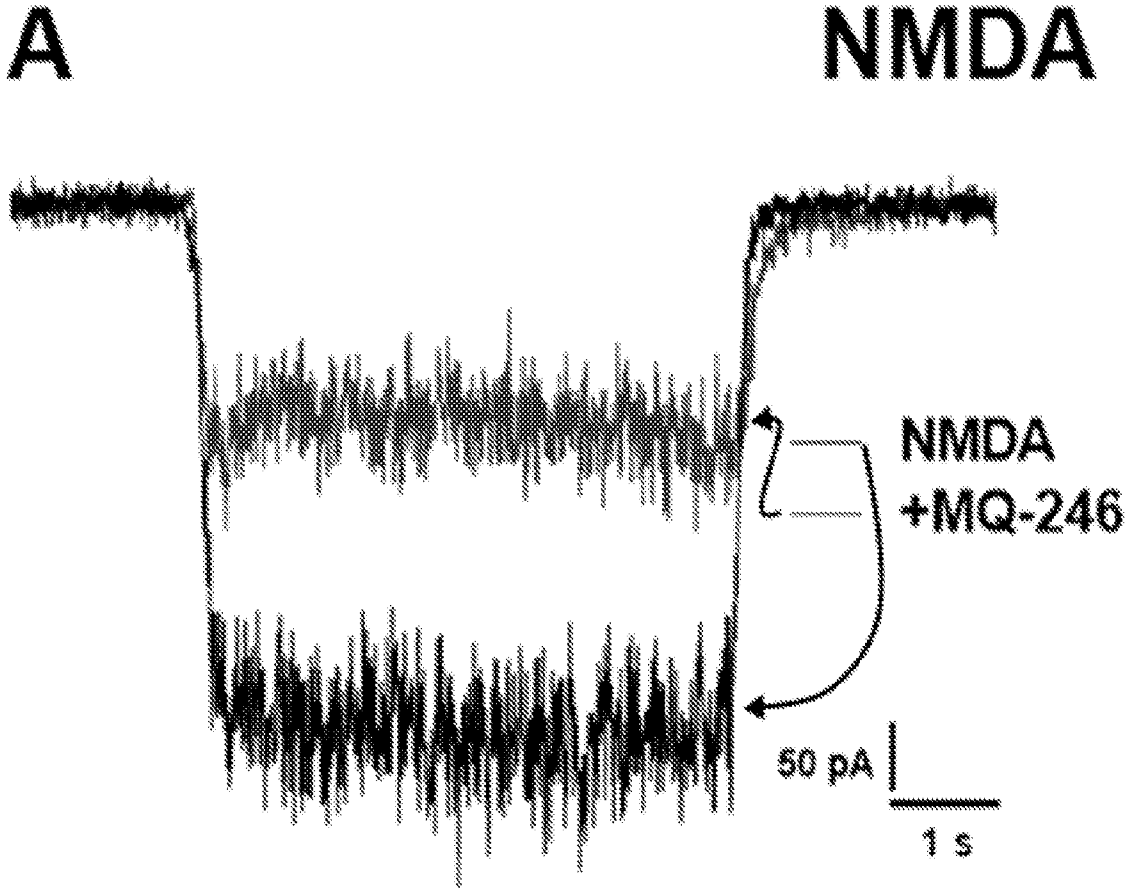
Figure 9:
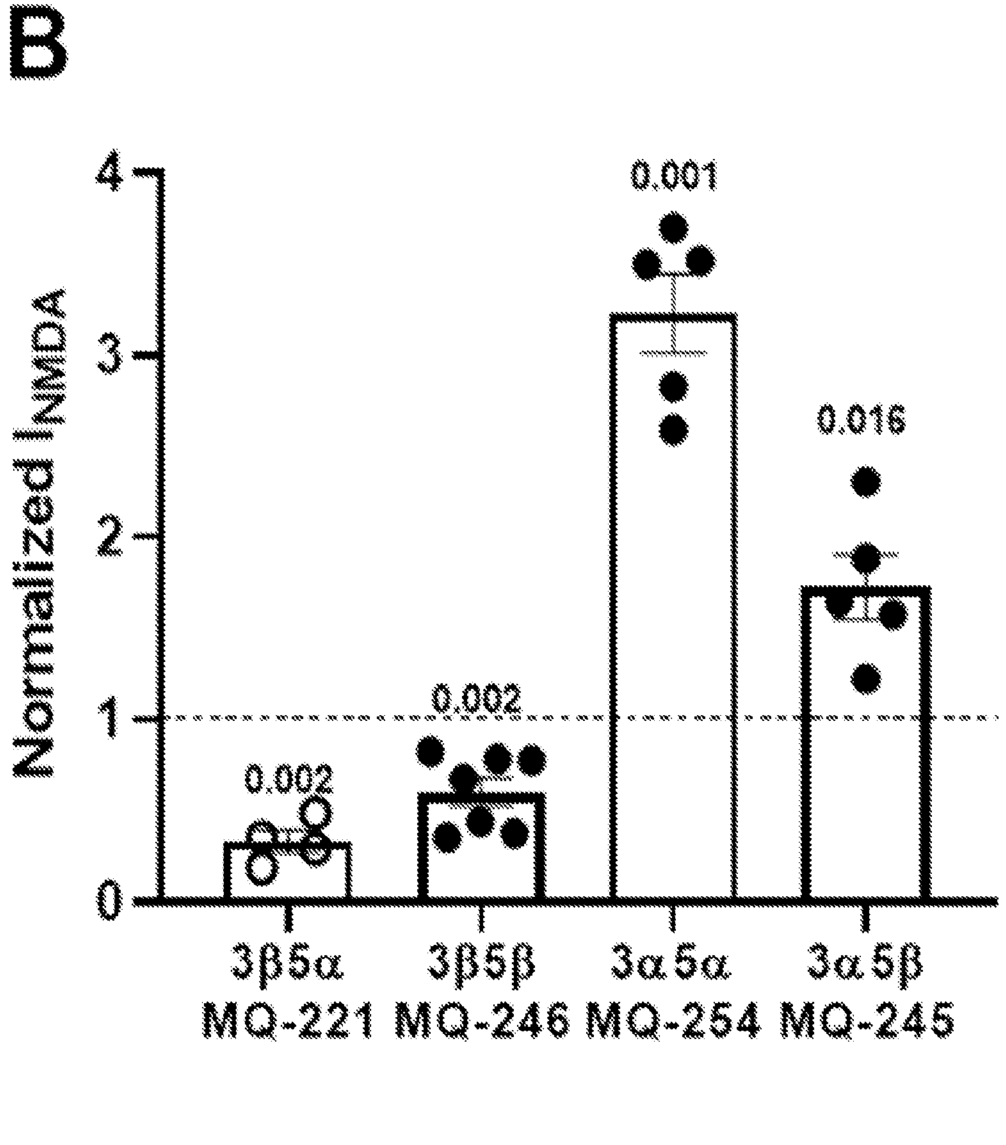
Figure 9:
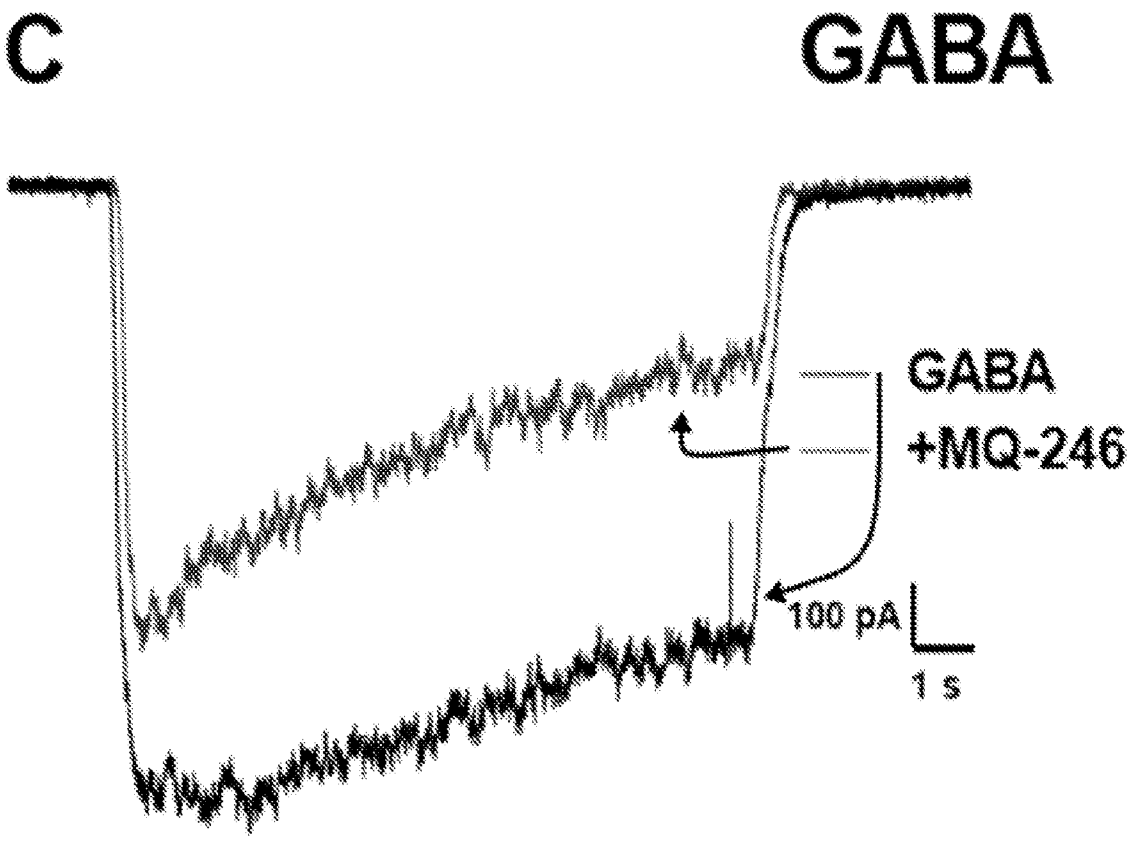
Figure 9:
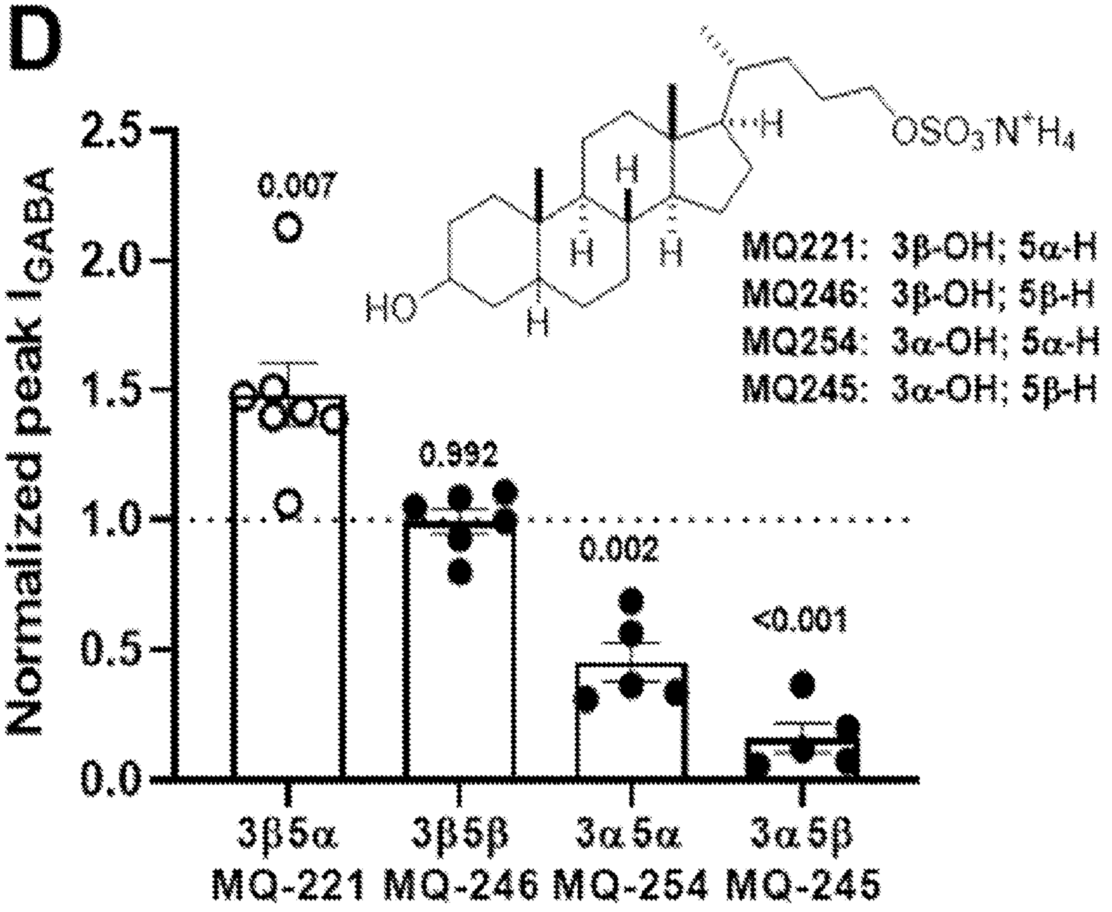

FIG. 9. Effects of MQ-221 stereoisomers. A, B. Effect of stereoisomers of MQ-221 on NMDA function. Panel A shows sample traces from a cell challenged with the only other inhibitor of NMDAR function, MQ-246, at 10 μM. B shows a summary of the impact of all compounds on response to 10 μM NMDA. C, D. Effects on responses to 2 μM GABA. The inset shows the structural scaffolding and isomer designations. MQ-246 (10 μM) had little effect on peak current but consistently inhibited steady-state current (73±3%, $n=6$, not shown). The other stereoisomers inhibited peak current and steady-state current. Values above bars show p values for one-sample t-tests.

Figure 10:
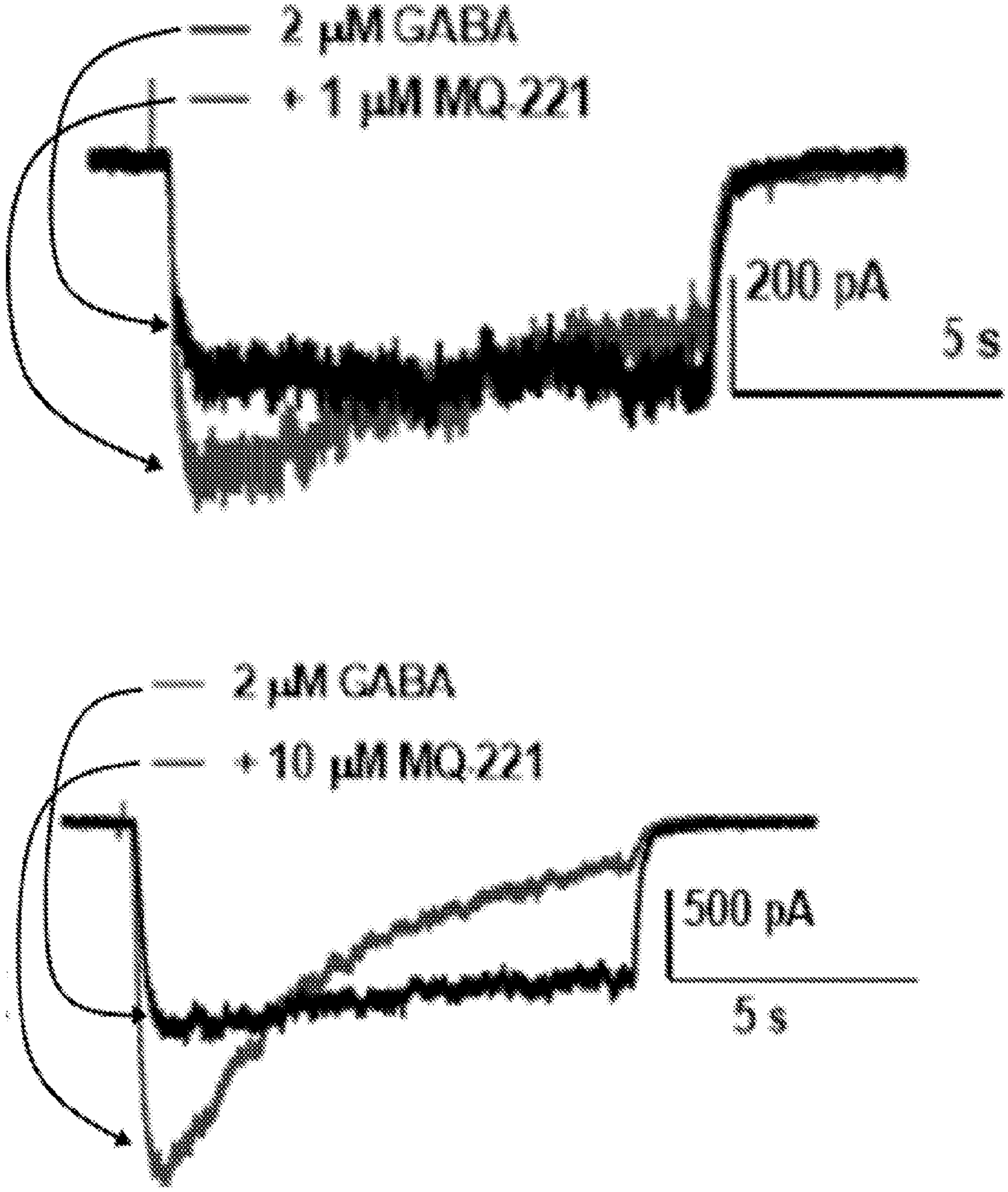
Figure 10:
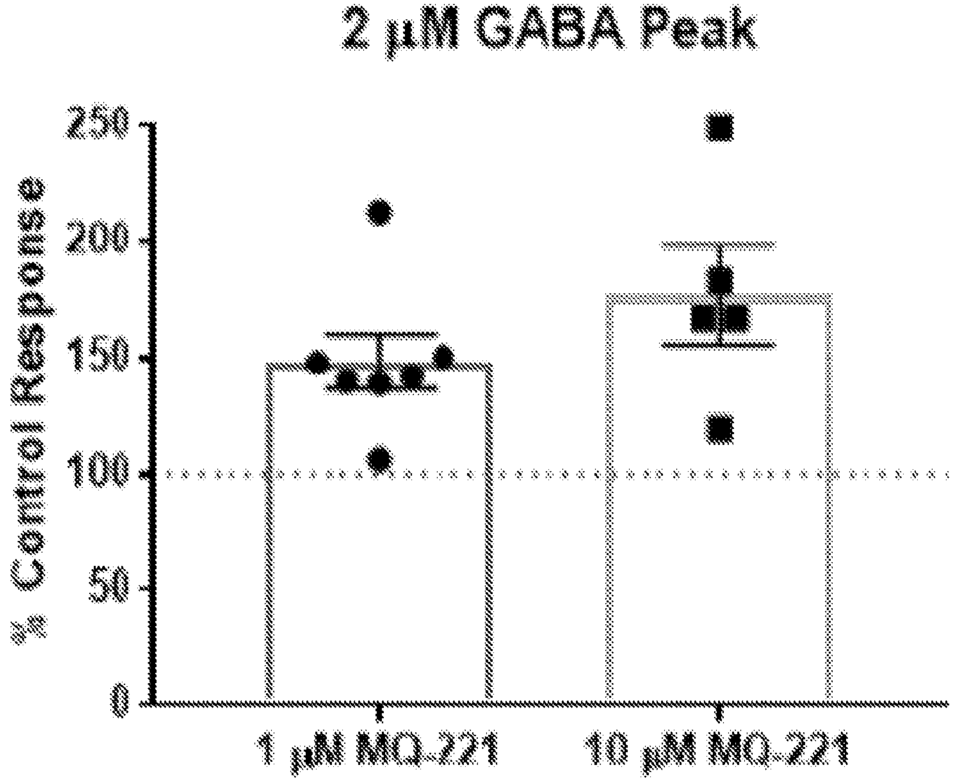
Figure 10:
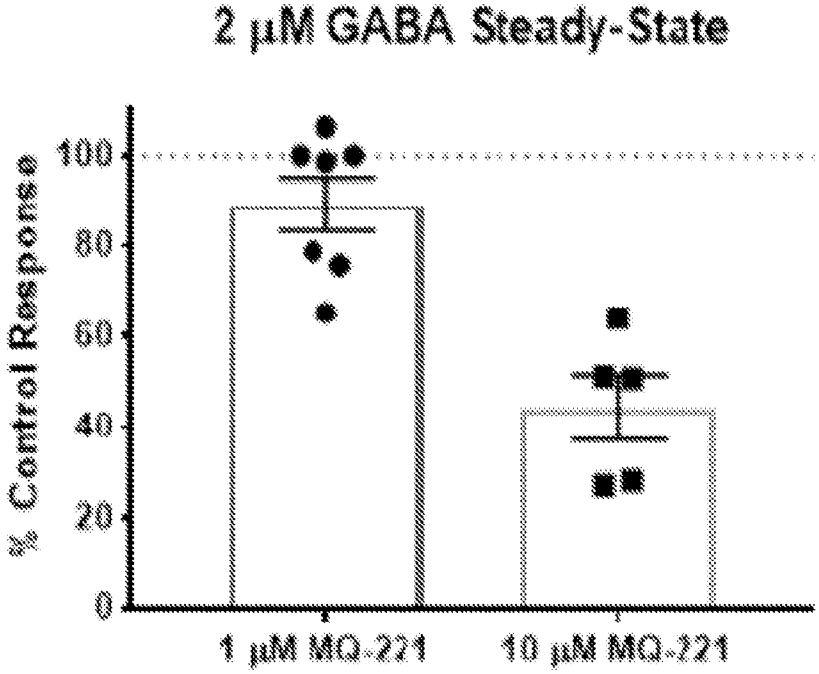
Figure 10:
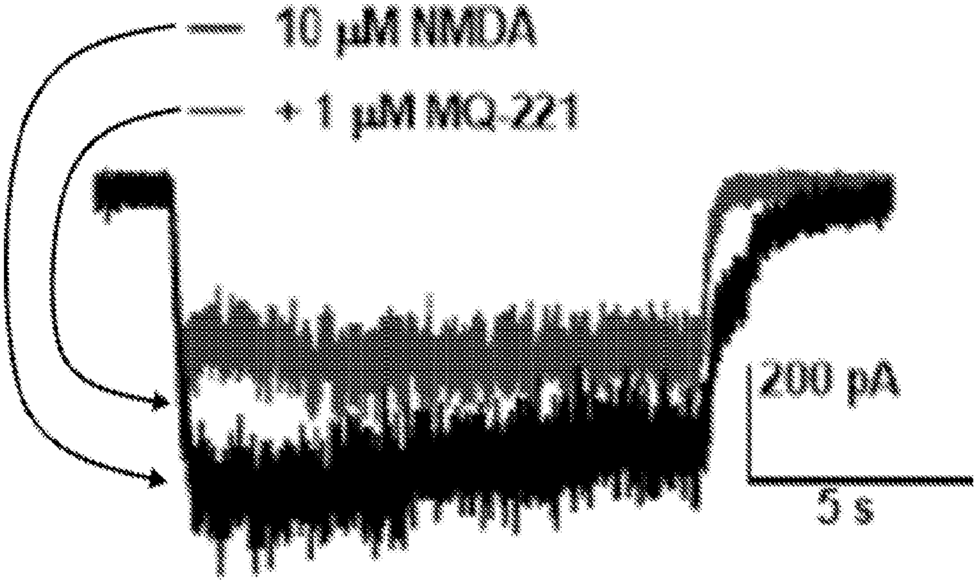
Figure 10:
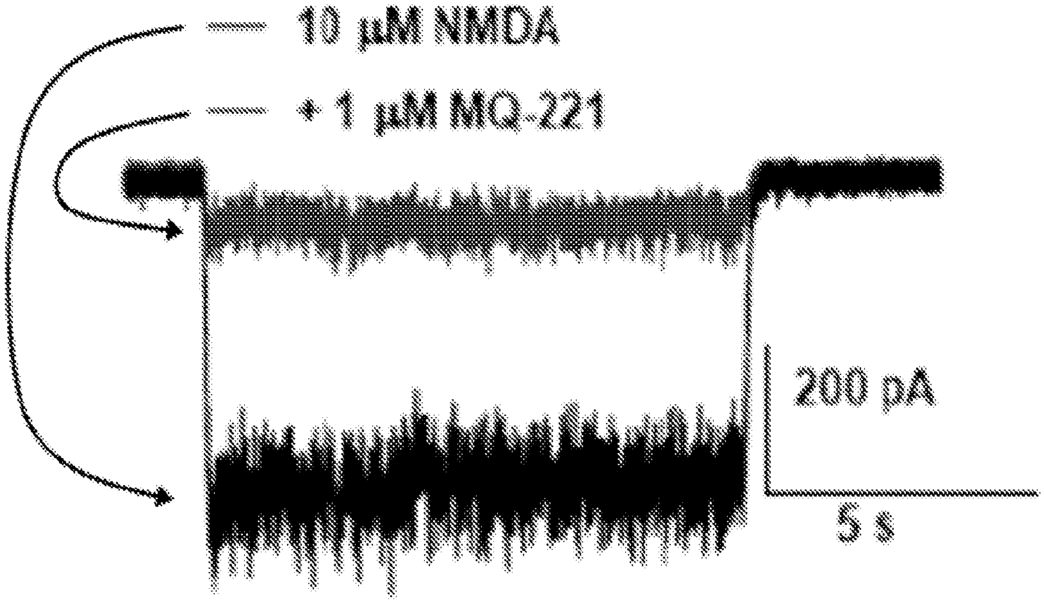
Figure 10:
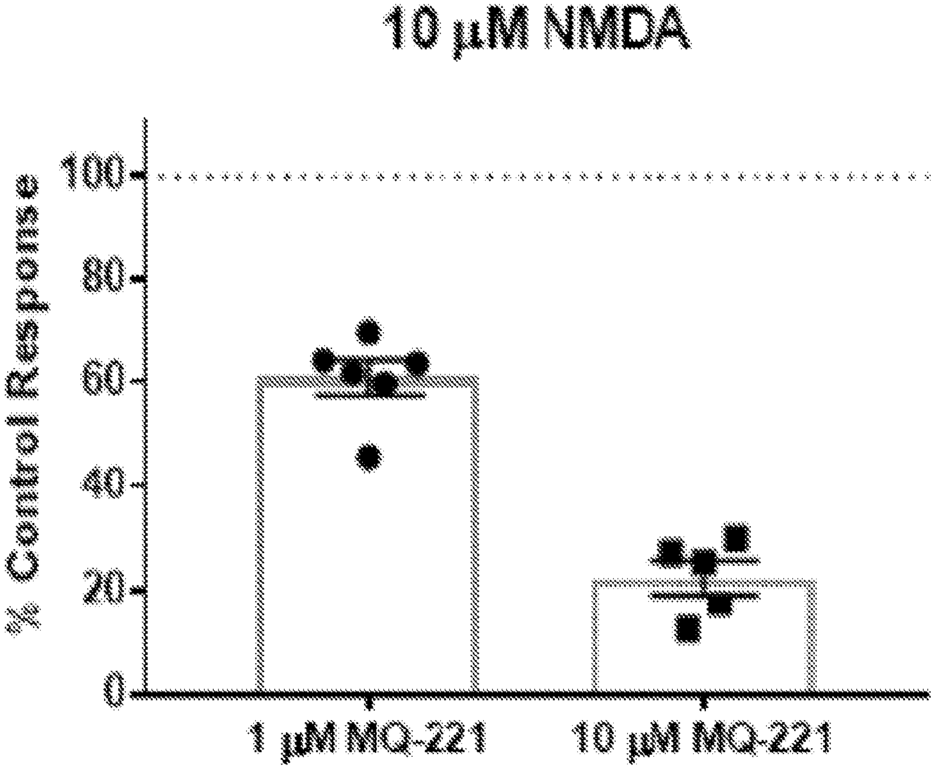

FIG. 10. MQ-221 pharmacological actions at NMDA (negative allosteric modulator) and $GABA_A$ (positive allosteric modulator) receptors.

DETAILED DESCRIPTION OF THE INVENTION

The present disclosure is based, at least in part, on the discovery of compounds exhibiting steroid modulating activity with actions at both NMDA and $GABA_A$ receptors. As shown herein, various compounds of formula (I) (e.g., MQ-221) exhibit action relative to other similar (sulfated, 3β hydroxyl) compounds is the unique effect of GABA, rather than NMDA, potentiation.

Surprisingly, it has been discovered that a sulfated, 3β-hydroxy neurosteroid analogue, MQ-221, inhibits NMDAR function but also potentiates $GABA_A$R function, thereby exhibiting an unusual but potentially clinically desirable constellation of effects. Although prolonged channel activation yielded the expected inhibition of $GABA_A$R function, IPSCs showed net potentiation under physiological conditions. Potentiation of $GABA_A$R function was distinct from the mechanism governing potentiation by anesthetic neurosteroids (Hosie et al., 2007). Inhibition of NMDAR function showed weaker channel activation dependence than pregnanolone sulfate (3α5βPS). MQ-221 was unique among four stereoisomers explored in the constellation of actions at $GABA_A$ and NMDARs. Taken together, MQ-221 and like analogs represent a new class of compounds with unique psychoactive effects that is beneficial for treating a variety of neuropsychiatric disorders.

The FDA approval of ketamine, an antagonist of N-methyl-D-aspartate (NMDA) receptors, and brexanolone, a neurosteroid that potentiates $GABA_A$ receptor function, has unveiled two separate inroads for treating depression-related illness. Compounds with both actions may represent a new generation of antidepressant drugs, and this invention discloses a compound with this unusual constellation of actions. It has unusual potentiating actions at $GABA_A$Rs and negatively modulates NMDARs. At both NMDARs and $GABA_A$Rs, it acted in the low μM range, making it unusual among steroidal NMDAR modulators, which typically require >30 μM for effectiveness.

The disclosed compositions and analogs thereof can be anew treatment for major depressive disorder.

Up to one third of patients suffering from depressive disorders are not aided by current medication. The FDA approval of ketamine, an antagonist of N-methyl-D-aspartate (NMDA) receptors, and brexanolone, a neurosteroid that potentiates $GABA_A$ receptor function, has unveiled two complementary inroads for the development of treatments for depression-related disorders. Compounds with both actions may represent a new generation of antidepressant drugs. Sulfated steroids have been of some interest as therapeutic agents in other contexts. Although some sulfated neurosteroids negatively modulate NMDARs, all known sulfated steroids antagonize $GABA_A$R function, an action that is likely counterproductive in the search for antidepressant drugs. Here, the compounds described herein, e.g., MQ-221, which bears structural similarity to sulfated neurosteroids was characterized. However, MQ-221 has unexpected potentiating actions at $GABA_A$Rs and negatively modulates NMDARS. At both NMDARs and $GABA_A$Rs, MQ-221 acted in the low μM range, making it unique among steroidal NMDAR modulators, which typically require >30 μM for effectiveness. Activity at $GABA_A$Rs was biphasic with inhibition increasing with both GABA and MQ-221 concentration, but potentiation dominated the actions of 1 μM MQ-221 on inhibitory synaptic currents. At NMDARs, inhibition by MQ-221 was independent of membrane potential and NMDA concentration. Unlike ketamine and the well-studied sulfated steroid pregnanolone sulfate (3α5βS), MQ-221 acted on closed NMDA channels, although it exhibited some activation dependence, as assessed by comparing drug pre-application with agonist co-application protocols. Three stereoisomers of MQ-221 were also examined and found that none of them had the actions of MQ-221.

The compounds described herein can be useful in treating psychiatric diseases, disorders, and conditions, such as neuropathological conditions.

Such psychiatric diseases, disorders, and conditions can be a depression-related illness, such as major depressive disorder. As such, the compounds described herein can be an anti-depressant drug.

Such psychiatric diseases, disorders, and conditions can be anxiety. As such, the compositions described herein can be an anti-anxiety drug.

Other psychiatric diseases, disorders, and conditions can be a disorder associated with NMDR or $GABA_A$R, such as sleep disorders, epilepsy, or schizophrenia.

The compounds described herein can also be used to treat or prevent alcohol use disorder in a subject in need thereof.

As noted, there is large unmet clinical need for novel medications to treat alcohol use disorder (AUD), which takes a very high personal and public health toll in the United States and worldwide. Medications remain underdeveloped. Acamprosate may be the most useful treatment, although it shows weak clinical and pharmacodynamic efficacy. Based on the acamprosate targets of $GABA_A$ receptors ($GABA_A$Rs) and NMDA receptors (NMDARs), the unique neurosteroid analogues described herein, e.g., MQ-221, acts more potently at the dual targets of $GABA_A$Rs and NMDARs. Without being bound by theory, the enhanced potency and efficacy of MQ-221-like compounds over acamprosate provides a superior medication to existing drug treatments of AUD. Accordingly, the disclosed compositions and analogs thereof can be a new treatment for AUD.

Accordingly, one preferred method of treating or preventing alcohol use disorder in a subject in need thereof comprises administering to the subject a composition comprising an effective amount of a compound of the following structure:

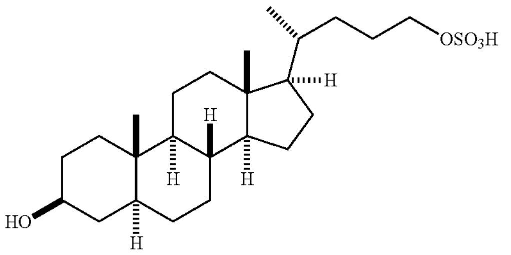

or pharmaceutically acceptable salt thereof.

NMDA Receptor Inhibiting/$GABA_A$ Receptor Potentiating Agents

Compositions as described herein are N-methyl-d-aspartate (NMDA) receptor negative allosteric modulators, negative allosteric modulators (NAM), and/or inhibitors of the NMDA receptor. They are closely related and similar to NMDA receptor antagonists. The N-methyl-d-aspartate receptor (NMDAR) family has many critical roles in CNS function and in various neuropathological and psychiatric conditions.

Compositions as described herein are $GABA_A$ receptor positive allosteric modulators (or $GABA_A$ receptor potentiators). $GABA_A$ receptor positive allosteric modulators are positive allosteric modulator (PAM) molecules that increase the activity of the $GABA_A$ receptor protein in the vertebrate central nervous system. GABA is a major inhibitory neurotransmitter in the central nervous system. Upon binding, it triggers the $GABA_A$ receptor to open its chloride channel to allow chloride ions into the neuron, making the cell hyperpolarized and less likely to fire. $GABA_A$ PAMs increase the effect of GABA by making the channel open more frequently or for longer periods. However, they have no effect if GABA or another agonist is not present.

Unlike $GABA_A$ receptor agonists, $GABA_A$ PAMs do not bind at the same active site as the γ-aminobutyric acid (GABA) neurotransmitter molecule. Instead, they affect the receptor by binding at a different site on the protein. This is called allosteric modulation.

Chemical agents as described herein have a unique effect on GABA potentiation and the compounds can exhibit strong activity in the 1 μM range rather than >30 μM (one order of magnitude smaller dose).

An NMDA receptor inhibiting/$GABA_A$ receptor potentiating agent can be either an NMDA receptor inhibiting agent or a $GABA_A$ receptor potentiating agent or both.

Examples of NMDA receptor inhibiting/$GABA_A$ receptor potentiating agents are described herein and include compounds of formula (I) and pharmaceutically acceptable salts thereof:

(I)

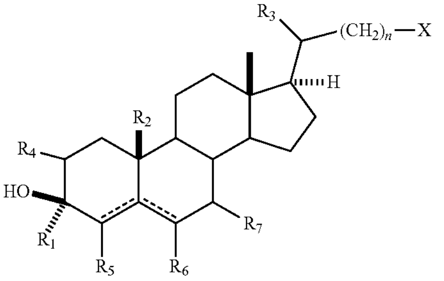

wherein:

$R_1$ is hydrogen, $C_1$ to $C_6$ alkyl, $C_1$ to $C_6$ alkenyl, $C_1$ to $C_6$ alkynyl, $C_1$ to $C_6$ alkoxy, or $C_1$ to $C_6$ haloalkyl;

$R_2$ is hydrogen, $C_1$ to $C_6$ alkyl, $C_1$ to $C_6$ alkenyl, $C_1$ to $C_6$ alkynyl, $C_1$ to $C_6$ alkoxy, $C_1$ to $C_6$ haloalkyl, $—CH_2O—R_A$, or $—CH_2O(C{=}O)—R_B$;

$R_3$ is hydrogen, $C_1$ to $C_6$ alkyl, $C_1$ to $C_6$ alkenyl, $C_1$ to $C_6$ alkynyl, $C_1$ to $C_6$ haloalkyl, $—CH_2O—R_A$, or $—CH_2O(C{=}O)—R_B$;

each $R_A$ is independently $C_1$ to $C_6$ alkyl or $C_1$ to $C_6$ haloalkyl;

each $R_B$ is independently hydrogen, $C_1$ to $C_6$ alkyl, or $C_1$ to $C_6$ haloalkyl;

$R_4$ is hydrogen, hydroxy, $C_1$ to $C_6$ alkyl, $C_1$ to $C_6$ alkenyl, $C_1$ to $C_6$ alkynyl, $C_1$ to $C_6$ alkoxy, or $C_1$ to $C_6$ haloalkyl;

$R_5$ is hydrogen, hydroxy, $C_1$ to $C_6$ alkyl, $C_1$ to $C_6$ alkenyl, $C_1$ to $C_6$ alkynyl, $C_1$ to $C_6$ alkoxy, or $C_1$ to $C_6$ haloalkyl;

$R_6$ is hydrogen, hydroxy, $C_1$ to $C_6$ alkyl, $C_1$ to $C_6$ alkenyl, $C_1$ to $C_6$ alkynyl, $C_1$ to $C_6$ alkoxy, or $C_1$ to $C_6$ haloalkyl;

$R_7$ is hydrogen, hydroxy, $C_1$ to $C_6$ alkyl, $C_1$ to $C_6$ alkenyl, $C_1$ to $C_6$ alkynyl, $C_1$ to $C_6$ alkoxy, or $C_1$ to $C_6$ haloalkyl;

X is hydroxy, $OSO_3H$, $OSO_3^-NH_4^+$, $SO_3H$, $SO_2H$, COOH, $NH(CH_2)_m—Y$, $H_2PO_4$, $HPO_3R_8$, $C(R_9)_2COOH$, $C(R_9)_2—Y$, or other negatively charged group at physiological pH;

Y is $OSO_3H$, $SO_3H$, $SO_2H$, COOH, $H_2PO_4$, $HPO_3R_8$, or other negatively charged group at physiological pH;

each $R_8$ is independently hydrogen, $C_1$ to $C_6$ alkyl or $C_1$ to $C_6$ haloalkyl;

each $R_9$ is independently hydrogen, $C_1$ to $C_6$ alkyl, $C_1$ to $C_6$ haloalkyl, or halo;

m is an integer from 1 to 6; and n is an integer from 1 to 8.

Pharmaceutically acceptable salts thereof include various salts, without limitation, as described herein. Preferred salts include amine salts, lithium salts, sodium salts, potassium salts, and mixtures thereof.

In various compounds of formula (I), the bond at the 4,5 position is a single bond. Alternatively, in some compounds, the bond at the 4,5 position is a double bond.

In various compounds of formula (I), the bond at the 5,6 position is a single bond. Alternatively, in some compounds, the bond at the 5,6 position is a double bond.

In various compounds of formula (I), $R_1$ is hydrogen, $C_1$ to $C_4$ alkyl, or $C_1$ to $C_4$ haloalkyl; $R_4$ is hydrogen, $C_1$ to $C_4$ alkyl, or $C_1$ to $C_4$ haloalkyl; $R_5$ is hydrogen, $C_1$ to $C_4$ alkyl, or $C_1$ to $C_4$ haloalkyl; $R_6$ is hydrogen, $C_1$ to $C_4$ alkyl, or $C_1$ to $C_4$ haloalkyl; and/or $R_7$ is hydrogen, $C_1$ to $C_4$ alkyl, or $C_1$ to $C_4$ haloalkyl.

In certain compounds of formula (I), $R_1$ is hydrogen, methyl, ethyl, propyl, halomethyl, haloethyl, or halopropyl; $R_4$ is hydrogen, methyl, ethyl, propyl, halomethyl, haloethyl, or halopropyl; $R_5$ is hydrogen, methyl, ethyl, propyl, halomethyl, haloethyl, or halopropyl; $R_6$ is hydrogen, methyl, ethyl, propyl, halomethyl, haloethyl, or halopropyl; and/or $R_7$ is hydrogen, methyl, ethyl, propyl, halomethyl, haloethyl, or halopropyl.

In some compounds of formula (I), at least one, at least two, at least three, at least four, or all of $R_1$, $R_4$, $R_5$, $R_6$, and $R_7$ are each hydrogen. In certain compounds of formula (I), at least of one of $R_2$, $R_4$, $R_5$, $R_6$, and $R_7$ is not hydrogen.

In various compounds of formula (I), $R_2$ is $C_1$ to $C_6$ alkyl or $C_1$ to $C_6$ haloalkyl. In some compounds of formula (I), $R_2$ is methyl, ethyl, propyl, halomethyl, haloethyl, or halopropyl. In certain compounds of formula (I), $R_2$ is methyl.

In various compounds of formula (I), $R_3$ is hydrogen, $C_1$ to $C_6$ alkyl, or $C_1$ to $C_6$ haloalkyl. In some compounds of formula (I), $R_3$ is hydrogen, methyl, ethyl, or propyl. In certain compounds of formula (I), $R_3$ is not hydrogen. In some compounds, $R_3$ is not methyl.

In various compounds of formula (I), $R_3$ is $—CH_2O(C{=}O)—R_B$ and $R_B$ is $C_1$ to $C_6$ alkyl.

In various compounds of formula (I), X is $OSO_3H$, $OSO_3^-NH_4^+$, $SO_3H$, $SO_2H$, COOH, $NH(CH_2)_m—Y$, $H_2PO_4$, $HPO_3R_8$, $C(R_9)_2COOH$, or $C(R_9)_2—Y$, and/or Y is $OSO_3H$, $OSO_3^-NH_4^+$, $SO_3H$, $SO_2H$, COOH, $H_2PO_4$, or $HPO_3R_8$. In some compounds, X is $OSO_3H$ or COOH. In certain compounds of formula (I), X is $OSO_3H$ or salt thereof (e.g., $OSO_3^-NH_4^+$).

In various compounds of formula (I), m is an integer from 1 to 5, from 1 to 4, from 1 to 3, from 1 to 2, or is 1, 2, 3, 4, 5, or 6.

In various compounds of formula (I), n is an integer from 1 to 7, from 1 to 6, from 1 to 5, from 1 to 4, from 1 to 3, from 1 to 2, or is 1, 2, 3, 4, 5, 6, 7, or 8.

Some compounds of formula (I) have a structure of formula (II), or a pharmaceutically acceptable salt thereof:

(II)

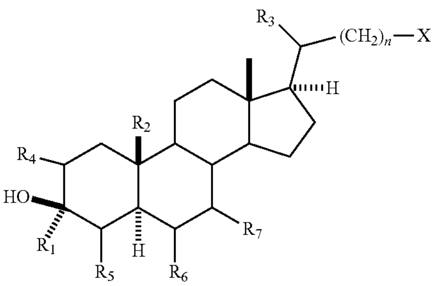

where $R_1$, $R_2$, $R_3$, $R_4$, $R_5$, $R_6$, $R_7$, and X are as defined above.

Some compounds of formula (I) have a structure of formula (III), or a pharmaceutically acceptable salt thereof:

(III)

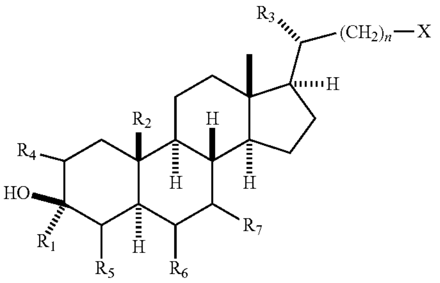

where $R_1$, $R_2$, $R_3$, $R_4$, $R_5$, $R_6$, $R_7$, and X are as defined above.

Certain compounds of formula (I) have a structure selected from the group consisting of:

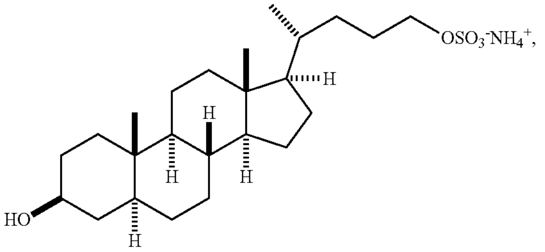

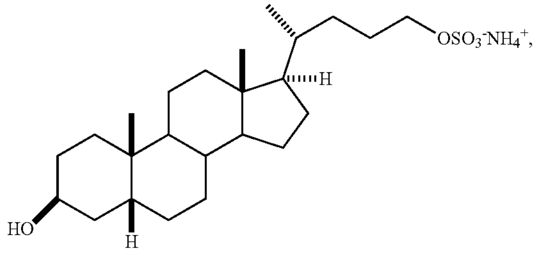

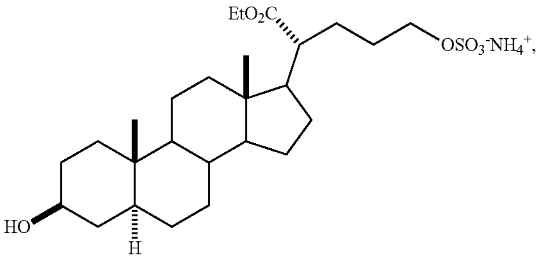

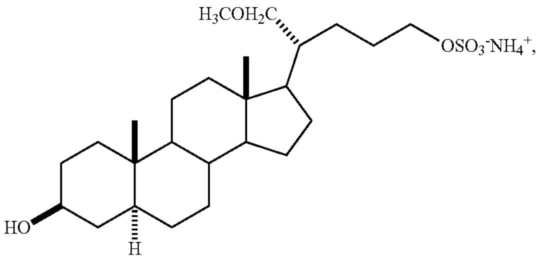

-continued

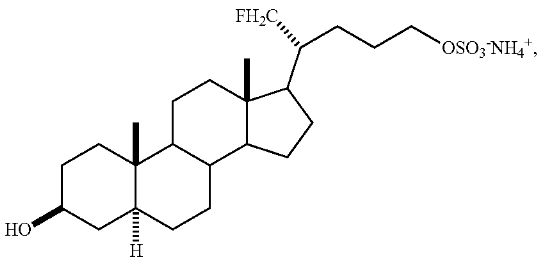

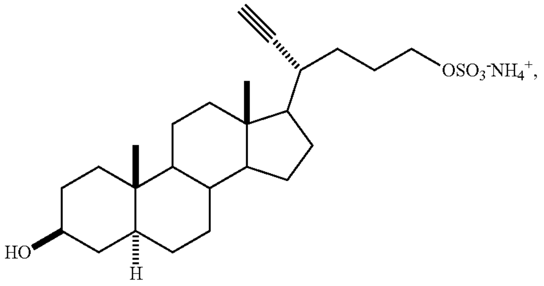

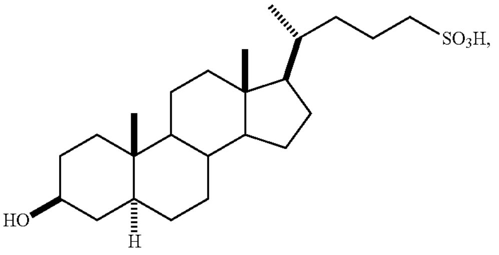

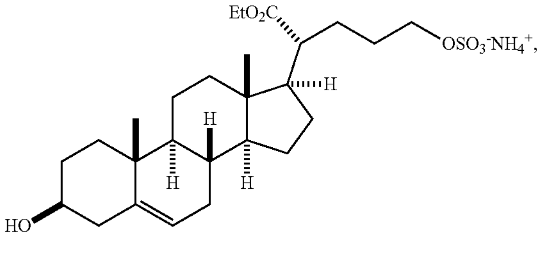

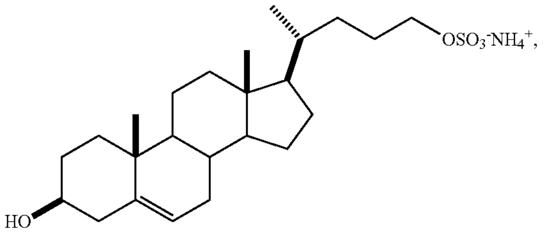

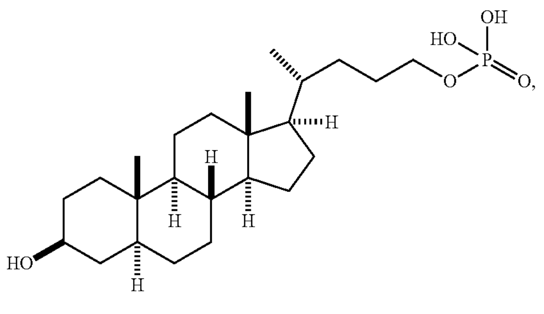

-continued

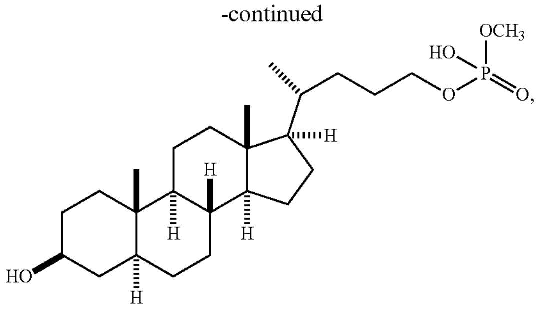

and pharmaceutically acceptable salts thereof.

Various preferred compounds of formula (I) include those of the following structure:

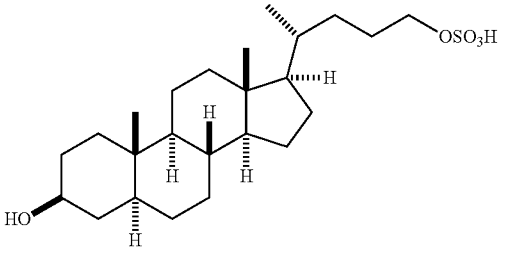

and a pharmaceutically acceptable salts thereof. For example, one preferred salt has a structure of:

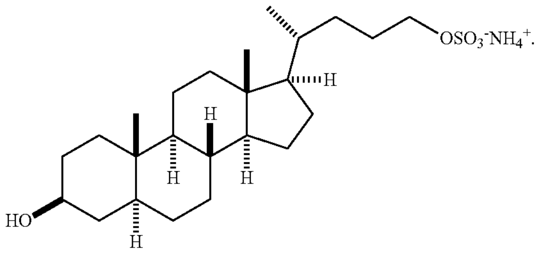

Various provisos may apply to the compounds of formulas (I)-(III) and pharmaceutically acceptable salts thereof. For example, when the bond at the 4,5 position is a single bond, the bond at the 5,6 position is a single bond, $R_2$ is methyl, $R_3$ is hydrogen, X is COOH, and n is 1, then at least of one of $R_1$, $R_4$, $R_5$, $R_6$, and $R_7$ is not hydrogen.

Additionally or alternatively, when the bond at the 4,5 position is a single bond, the bond at the 5,6 position is a single bond, $R_2$ is methyl, $R_3$ is methyl, X is COOH, and n is 1 or 2, then at least of one of $R_1$, $R_4$, $R_5$, $R_6$, and $R_7$ is not hydrogen.

Additionally or alternatively, when the bond at the 4,5 position is a single bond, the bond at the 5,6 position is a double bond, $R_2$ is methyl, $R_3$ is methyl, X is COOH, and n is 1, 2 or 3, then at least of one of $R_1$, $R_4$, $R_5$, $R_6$, and $R_7$ is not hydrogen.

Additionally or alternatively, when the bond at the 4,5 position is a single bond, the bond at the 5,6 position is a double bond, $R_2$ is methyl, $R_3$ is methyl, X is $C(R_9)_2COOH$, each $R_9$ is halo, and n is 1, 2, or 3, then at least of one of $R_1$, $R_4$, $R_5$, $R_6$, and $R_7$ is not hydrogen.

Additionally or alternatively, when the bond at the 4,5 position is a single bond, the bond at the 5,6 position is a double bond, $R_2$ is methyl, $R_3$ is methyl, X is $C(R_9)_2COOH$, each $R_9$ is fluoro, and n is 1, 2, or 3, then at least of one of $R_1$, $R_4$, $R_5$, $R_6$, and $R_7$ is not hydrogen.

Additionally or alternatively, when the bond at the 4,5 position is a single bond, the bond at the 5,6 position is a double bond, $R_2$ is methyl, $R_3$ is methyl, X is $C(R_9)_2COOH$, $R_9$ is bromo, and n is 1, 2, or 3, then at least of one of $R_1$, $R_4$, $R_5$, $R_6$, and $R_7$ is not hydrogen.

These provisos may be applied in combination. For example, when the bond at the 4,5 position is a single bond, the bond at the 5,6 position is a single bond, $R_2$ is methyl, $R_3$ is hydrogen, X is COOH, and n is 1, then at least of one of $R_1$, $R_4$, $R_5$, $R_6$, and $R_7$ is not hydrogen;

when the bond at the 4,5 position is a single bond, the bond at the 5,6 position is a single bond, $R_2$ is methyl, $R_3$ is methyl, X is COOH, and n is 1 or 2, then at least of one of $R_1$, $R_4$, $R_5$, $R_6$, and $R_7$ is not hydrogen;

when the bond at the 4,5 position is a single bond, the bond at the 5,6 position is a double bond, $R_2$ is methyl, $R_3$ is methyl, X is COOH, and n is 1, 2 or 3, then at least of one of $R_1$, $R_4$, $R_5$, $R_6$, and $R_7$ is not hydrogen; and when the bond at the 4,5 position is a single bond, the bond at the 5,6 position is a double bond, $R_2$ is methyl, $R_3$ is methyl, X is $C(R_9)_2COOH$, $R_9$ is halo, and n is 1, 2, or 3, then at least of one of $R_1$, $R_4$, $R_5$, $R_6$, and $R_7$ is not hydrogen.

In some embodiments, a NMDA receptor inhibiting/$GABA_A$ receptor potentiating agent can be, of the formula (IV):

(IV)

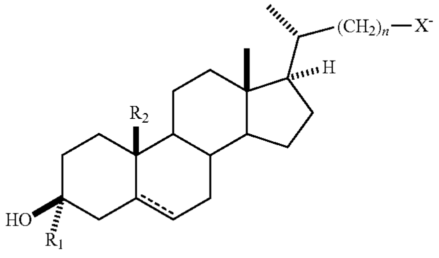

or a pharmaceutically acceptable salt thereof, including all tautomers and stereoisomers, and optionally substituted analogues thereof.

In some embodiments, $R_1$ is H or $C_{1-4}$ alkyl; $R_2$ is H or $C_{1-4}$ alkyl; n=1-8; and X is $OSO_3H$ or COOH or other negatively charged group at physiological pH or salt thereof. In some embodiments, when the $C_5$-$C_6$ double bond is not present there is an α-H at position $C_5$.

In various embodiments, the compound of formula (IV) is a compound of formula (V):

(V)

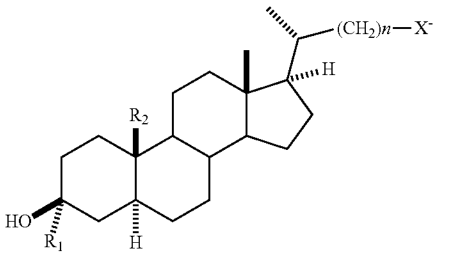

or a pharmaceutically acceptable salt thereof, wherein $R_1$ is H or $C_{1-4}$ alkyl;

$R_2$ is H or $C_{1-4}$ alkyl;

n=1-8; and

X is $OSO_3H$ or COOH or other negatively charged group at physiological pH or salt thereof.

In some embodiments, the compound of formula (IV) can be

MQ-221

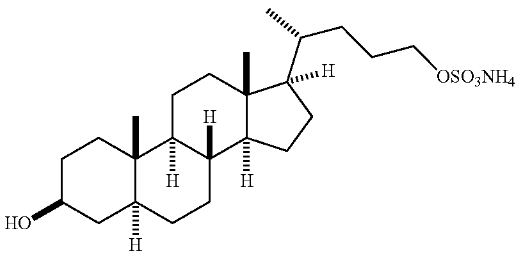

In some embodiments, the compounds of formulas (I)-(V) have NMDA receptor inhibitory activity and/or $GABA_A$ receptor potentiation activity.

Analogs of MQ-221 can include the addition or substitution with a variety of R groups which can be optionally substituted with one or more groups independently selected from the group consisting of hydroxyl; $C_{1-10}$alkyl hydroxyl; amine; $C_{1-10}$carboxylic acid; $C_{1-10}$carboxyl; straight chain or branched $C_{1-10}$alkyl, optionally containing unsaturation; a $C_{2-10}$cycloalkyl optionally containing unsaturation or one oxygen or nitrogen atom; straight chain or branched $C_{1-10}$alkyl amine; heterocyclyl; heterocyclic amine; and aryl comprising a phenyl; heteroaryl containing from 1 to 4 N, O, or S atoms; unsubstituted phenyl ring; substituted phenyl ring; unsubstituted heterocyclyl; and substituted heterocyclyl, wherein the unsubstituted phenyl ring or substituted phenyl ring can be optionally substituted with one or more groups independently selected from the group consisting of hydroxyl; $C_{1-10}$alkyl hydroxyl; amine; $C_{1-10}$carboxylic acid; $C_{1-10}$carboxyl; straight chain or branched $C_{1-10}$alkyl, optionally containing unsaturation; straight chain or branched $C_{1-10}$alkyl amine, optionally containing unsaturation; a $C_{2-10}$cycloalkyl optionally containing unsaturation or one oxygen or nitrogen atom; straight chain or branched $C_{1-10}$alkyl amine; heterocyclyl; heterocyclic amine; aryl comprising a phenyl; and heteroaryl containing from 1 to 4 N, O, or S atoms; and the unsubstituted heterocyclyl or substituted heterocyclyl can be optionally substituted with one or more groups independently selected from the group consisting of hydroxyl; $C_{1-10}$alkyl hydroxyl; amine; $C_{1-10}$carboxylic acid; $C_{1-10}$carboxyl; straight chain or branched $C_{1-10}$alkyl, optionally containing unsaturation; straight chain or branched $C_{1-10}$alkyl amine, optionally containing unsaturation; a $C_{2-10}$cycloalkyl optionally containing unsaturation or one oxygen or nitrogen atom; heterocyclyl; straight chain or branched $C_{1-10}$alkyl amine; heterocyclic amine; and aryl comprising a phenyl; and heteroaryl containing from 1 to 4 N, O, or S atoms. Any of the above can be further optionally functionalized or substituted with R groups.

The term "imine" or "imino", as used herein, unless otherwise indicated, can include a functional group or chemical compound containing a carbon-nitrogen double bond. The expression "imino compound", as used herein, unless otherwise indicated, refers to a compound that includes an "imine" or an "imino" group as defined herein. The "imine" or "imino" group can be optionally substituted.

The term "hydroxyl", as used herein, unless otherwise indicated, can include —OH. The "hydroxyl" can be optionally substituted.

The terms "halogen" and "halo", as used herein, unless otherwise indicated, include a chlorine, chloro, Cl; fluorine, fluoro, F; bromine, bromo, Br; or iodine, iodo, or I. Preferred "halo" groups include fluoro and bromo.

The term "haloalkyl" as used herein, unless otherwise indicated, includes chloroalkyl, fluoroalkyl, bromoalkyl, iodoalkyl groups and groups such as halomethyl, haloethyl, or halopropyl. The term "haloalkyl" also includes groups having multiple halo substituents, such as trifluoroalkyl (e.g., trifluoromethyl). Haloalkyls can be saturated, partially saturated, or unsaturated.

The term "acetamide", as used herein, is an organic compound with the formula $CH_3CONH_2$. The "acetamide" can be optionally substituted.

The term "aryl", as used herein, unless otherwise indicated, include a carbocyclic aromatic group. Examples of aryl groups include, but are not limited to, phenyl, benzyl, naphthyl, or anthracenyl. The "aryl" can be optionally substituted.

The terms "amine", "aminyl", and "amino", as used herein, unless otherwise indicated, include a functional group that contains a nitrogen atom with a lone pair of electrons and wherein one or more hydrogen atoms have been replaced by a substituent such as, but not limited to, an alkyl group or an aryl group. The "amine" or "amino" group can be optionally substituted.

The term "alkyl", as used herein, unless otherwise indicated, can include saturated monovalent hydrocarbon radicals having straight or branched moieties, such as but not limited to, methyl, ethyl, propyl, butyl, pentyl, hexyl, octyl groups, etc. Representative straight-chain lower alkyl groups include, but are not limited to, -methyl, -ethyl, -n-propyl, -n-butyl, -n-pentyl, -n-hexyl, -n-heptyl and -n-octyl; while branched lower alkyl groups include, but are not limited to, -isopropyl, -sec-butyl, -isobutyl, -tert-butyl, -isopentyl, 2-methylbutyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, unsaturated $C_{1-10}$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, or -3-methyl-1 butynyl. An alkyl can be saturated, partially saturated, or unsaturated. The "alkyl" can be optionally substituted.

The term "carboxyl", as used herein, unless otherwise indicated, can include a functional group consisting of a carbon atom double bonded to an oxygen atom and single bonded to a hydroxyl group (—COOH). The "carboxyl" can be optionally substituted.

The term "alkenyl", as used herein, unless otherwise indicated, can include alkyl moieties having at least one carbon-carbon double bond wherein alkyl is as defined above and including E and Z isomers of said alkenyl moiety. An alkenyl can be partially saturated or unsaturated. The "alkenyl" can be optionally substituted.

The term "alkynyl", as used herein, unless otherwise indicated, can include alkyl moieties having at least one carbon-carbon triple bond wherein alkyl is as defined above. An alkynyl can be partially saturated or unsaturated. The "alkynyl" can be optionally substituted.

The term "acyl", as used herein, unless otherwise indicated, can include a functional group derived from an aliphatic carboxylic acid, by removal of the hydroxyl (—OH) group. The "acyl" can be optionally substituted.

The term "alkoxy" or "alkoxyl", as used herein, unless otherwise indicated, can include O-alkyl groups wherein alkyl is as defined above and O represents oxygen. Representative alkoxyl groups include, but are not limited to, —O-methyl, —O-ethyl, —O-n-propyl, —O-n-butyl, —O-n-pentyl, —O-n-hexyl, —O-n-heptyl, —O-n-octyl, —O-isopropyl, —O-sec-butyl, —O-isobutyl, —O-tert-butyl, —O-isopentyl, —O-2-methylbutyl, —O-2-methylpentyl, —O-3-methylpentyl, —O-2,2-dimethylbutyl, —O-2,3-dimethylbutyl, —O-2,2-dimethylpentyl, —O-2,3-dimethylpentyl, —O-3,3-dimethylpentyl, —O-2,3,4-trimethylpentyl, —O-3-methylhexyl, —O-2,2-dimethylhexyl, —O-2,4-dimethylhexyl, —O-2,5-dimethylhexyl, —O-3,5-dimethylhexyl, —O-2,4dimethylpentyl, —O-2-methylheptyl, —O-3-methylheptyl, —O-vinyl, —O-allyl, —O-1-butenyl, —O-2-butenyl, —O-isobutylenyl, —O-1-pentenyl, —O-2-pentenyl, —O-3-methyl-1-butenyl, —O-2-methyl-2-butenyl, —O-2,3-dimethyl-2-butenyl, —O-1-hexyl, —O-2-hexyl, —O-3-hexyl, —O-acetylenyl, —O-propynyl, —O-1-butynyl, —O-2-butynyl, —O-1-pentynyl, —O-2-pentynyl and —O-3-methyl-1-butynyl, —O-cyclopropyl, —O-cyclobutyl, —O-cyclopentyl, —O-cyclohexyl, —O-cycloheptyl, —O-cyclooctyl, —O-cyclononyl and —O-cyclodecyl, —O—$CH_2$-cyclopropyl, —O—$CH_2$-cyclobutyl, —O—$CH_2$-cyclopentyl, —O—$CH_2$-cyclohexyl, —O—$CH_2$-cycloheptyl, —O—$CH_2$-cyclooctyl, —O—$CH_2$-cyclononyl, —O—$CH_2$-cyclodecyl, —O—$(CH_2)_2$-cyclopropyl, —O—$(CH_2)_2$-cyclobutyl, —O—$(CH_2)_2$-cyclopentyl, —O—$(CH_2)_2$-cyclohexyl, —O—$(CH_2)_2$-cycloheptyl, —O—$(CH_2)_2$-cyclooctyl, —O—$(CH_2)_2$-cyclononyl, or —O—$(CH_2)_2$-cyclodecyl. An alkoxy or alkoxyl can be saturated, partially saturated, or unsaturated. The "alkoxyl" can be optionally substituted.

The term "cycloalkyl", as used herein, unless otherwise indicated, can include an aromatic, a non-aromatic, saturated, partially saturated, or unsaturated, monocyclic or fused, spiro or unfused bicyclic or tricyclic hydrocarbon referred to herein containing a total of from 1 to 10 carbon atoms (e.g., 1 or 2 carbon atoms if there are other heteroatoms in the ring), preferably 3 to 8 ring carbon atoms. Examples of cycloalkyls include, but are not limited to, $C_{3-10}$ cycloalkyl groups include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. The term "cycloalkyl" also can include -lower alkyl-cycloalkyl, wherein lower alkyl and cycloalkyl are as defined herein. Examples of -lower alkyl-cycloalkyl groups include, but are not limited to, —$CH_2$-cyclopropyl, —$CH_2$-cyclobutyl, —$CH_2$-cyclopentyl, —$CH_2$-cyclopentadienyl, —$CH_2$-cyclohexyl, —$CH_2$-cycloheptyl, or —$CH_2$-cyclooctyl. The "cycloalkyl" can be optionally substituted. A "cycloheteroalkyl", as used herein, unless otherwise indicated, can include any of the above with a carbon substituted with a heteroatom (e.g., O, S, N).

The term "heterocyclic" or "heteroaryl", as used herein, unless otherwise indicated, can include an aromatic or non-aromatic cycloalkyl in which one to four of the ring carbon atoms are independently replaced with a heteroatom from the group consisting of O, S and N. Representative examples of a heterocycle include, but are not limited to, benzofuranyl, benzothiophene, indolyl, benzopyrazolyl, coumarinyl, isoquinolinyl, pyrrolyl, pyrrolidinyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl, (1,4)-dioxane, (1,3)-dioxolane, 4,5-dihydro-1H-imidazolyl, or tetrazolyl. Heterocycles can be substituted or unsubstituted. Heterocycles can also be bonded at any ring atom (i.e., at any carbon atom or heteroatom of the heterocyclic ring). A heterocyclic can be saturated, partially saturated, or unsaturated. The "heterocyclic" can be optionally substituted.

The term "indole", as used herein, is an aromatic heterocyclic organic compound with formula $C_8H_7N$. It has a bicyclic structure, consisting of a six-membered benzene ring fused to a five-membered nitrogen-containing pyrrole ring. The "indole" can be optionally substituted.

The term "cyano", as used herein, unless otherwise indicated, can include a —CN group. The "cyano" can be optionally substituted.

The term "alcohol", as used herein, unless otherwise indicated, can include a compound in which the hydroxyl functional group (—OH) is bound to a carbon atom. In particular, this carbon center should be saturated, having single bonds to three other atoms. The "alcohol" can be optionally substituted.

The term "solvate" is intended to mean a solvate form of a specified compound that retains the effectiveness of such compound. Examples of solvates include compounds of the invention in combination with, for example: water, isopropanol, ethanol, methanol, dimethylsulfoxide (DMSO), ethyl acetate, acetic acid, or ethanolamine.

The term "mmol", as used herein, is intended to mean millimole. The term "equiv", as used herein, is intended to mean equivalent. The term "mL", as used herein, is intended to mean milliliter. The term "g", as used herein, is intended to mean gram. The term "kg", as used herein, is intended to mean kilogram. The term "μg", as used herein, is intended to mean micrograms. The term "h", as used herein, is intended to mean hour. The term "min", as used herein, is intended to mean minute. The term "M", as used herein, is intended to mean molar. The term "L", as used herein, is intended to mean microliter. The term "μM", as used herein, is intended to mean micromolar. The term "nM", as used herein, is intended to mean nanomolar. The term "N", as used herein, is intended to mean normal. The term "amu", as used herein, is intended to mean atomic mass unit. The term "° C.", as used herein, is intended to mean degree Celsius. The term "wt/wt", as used herein, is intended to mean weight/weight. The term "v/v", as used herein, is intended to mean volume/volume. The term "MS", as used herein, is intended to mean mass spectroscopy. The term "HPLC", as used herein, is intended to mean high performance liquid chromatograph. The term "RT", as used herein, is intended to mean room temperature. The term "e.g.", as used herein, is intended to mean example. The term "N/A", as used herein, is intended to mean not tested.

As used herein, the expression "pharmaceutically acceptable salt" refers to pharmaceutically acceptable organic or inorganic salts of a compound of the invention. One preferred salt includes the amine salt ($NH_4^+$). Other preferred salts include, but are not limited, various metal salts, such as alkali salts (e.g., lithium, sodium, and potassium salts). Preferred salts also include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, or pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counterion. As used herein, the expression "pharmaceutically acceptable solvate" refers to an association of one or more solvent molecules and a compound of the invention. Examples of solvents that form pharmaceutically acceptable solvates include, but are not limited to, water, isopropanol, ethanol, methanol, DMSO, ethyl acetate, acetic acid, and ethanolamine. As used herein, the expression "pharmaceutically acceptable hydrate" refers to a compound of the invention, or a salt thereof, that further can include a stoichiometric or non-stoichiometric amount of water bound by non-covalent intermolecular forces.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). One preferred excipient includes cyclodextrin.

Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, oral, topical, intradermal, intranasal, intramuscular, intraperitoneal, intravenous, subcutaneous, epidural, transdermal, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating or preventing a psychiatric disease, disorder, or condition in a subject in need of administration of a therapeutically effective amount of an NMDA receptor inhibiting/$GABA_A$ receptor potentiating agent as described herein (e.g., one or more compounds of formulas (I)-(V)), so as to inhibit NMDAR and/or potentiate $GABA_AR$.

Methods described herein are generally performed on a subject in need thereof. A subject in need of the therapeutic methods described herein can be a subject having, diagnosed with, suspected of having, or at risk for developing a psychiatric disease, disorder, or condition. A determination of the need for treatment will typically be assessed by a history, physical exam, or diagnostic tests consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans or chickens. For example, the subject can be a human subject.

Generally, a safe and effective amount of an NMDA receptor inhibiting/$GABA_A$ receptor potentiating agent is, for example, that amount that would cause the desired therapeutic effect in a subject while minimizing undesired side effects. In various embodiments, an effective amount of an NMDA receptor inhibiting/$GABA_A$ receptor potentiating agent described herein can substantially inhibit NMDAR, potentiate $GABA_AR$, slow the progress of a psychiatric disease, disorder, or condition, or limit the development of a psychiatric disease, disorder, or condition.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of an NMDA receptor inhibiting/$GABA_A$ receptor potentiating agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to potentiate $GABA_AR$ or inhibit NMDR.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment. In some instances, the compound is administered in an amount of from about 0.1 mg to about 75 mg, from about 0.5 mg to about 50 mg, or from about 1 mg to about 25 mg per kg of bodyweight. Also, the composition can be administered once per day, twice per day, three times per day, or once every other day.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of an NMDA receptor inhibiting/$GABA_A$ receptor potentiating agent can occur as a single event or over a time course of treatment. For example, an NMDA receptor inhibiting/$GABA_A$ receptor potentiating agent can be administered daily, weekly, bi-weekly, or monthly. Treatment could extend from several weeks to several months or even a year or more.

Treatment in accord with the methods described herein can be performed prior to, concurrent with, or after conventional treatment modalities for a psychiatric disease, disorder, or condition.

An NMDA receptor inhibiting/GABAA receptor potentiating agent can be administered simultaneously or sequentially with another agent, such as an anti-psychotic, an anti-depressant, or anti-anxiety drug. For example, an NMDA receptor inhibiting/GABAA receptor potentiating agent can be administered simultaneously with another agent, such as an anti-psychotic, an anti-depressant, or anti-anxiety drug. Simultaneous administration can occur through administration of separate compositions, each containing one or more of an NMDA receptor inhibiting/GABAA receptor potentiating agent, an anti-psychotic, an anti-depressant, or anti-anxiety drug. Simultaneous administration can occur through administration of one composition containing two or more of an NMDA receptor inhibiting/GABAA receptor potentiating agent, an anti-psychotic, an anti-depressant, or anti-anxiety drug. An NMDA receptor inhibiting/GABAA receptor potentiating agent can be administered sequentially with an anti-psychotic, an anti-depressant, or anti-anxiety drug. For example, an NMDA receptor inhibiting/$GABA_A$ receptor potentiating agent can be administered before or after administration of an anti-psychotic, an anti-depressant, or anti-anxiety drug.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 μm), nanospheres (e.g., less than 1 μm), microspheres (e.g., 1-100 μm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Screening

Also provided are methods for screening for an NMDA receptor inhibiting/$GABA_A$ receptor potentiating agent.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 mw, or less than about 1000 mw, or less than about 800 mw) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example: ChemBridge, Princeton BioMolecular, Ambinter SARL, Enamine, ASDI, Life Chemicals etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character xlogP of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character xlogP of less than about 5) (see e.g., Lipinski (2000) J. Pharm. Tox. Methods 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical successful if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

A control sample or a reference sample as described herein can be a sample from a healthy subject. A reference value can be used in place of a control or reference sample, which was previously obtained from a healthy subject or a group of healthy subjects. A control sample or a reference sample can also be a sample with a known amount of a detectable compound or a spiked sample.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Synthesis of MQ221

The synthesis of steroid MQ221 is described and shown in the scheme below.

Scheme 1: Synthesis of MQ-221

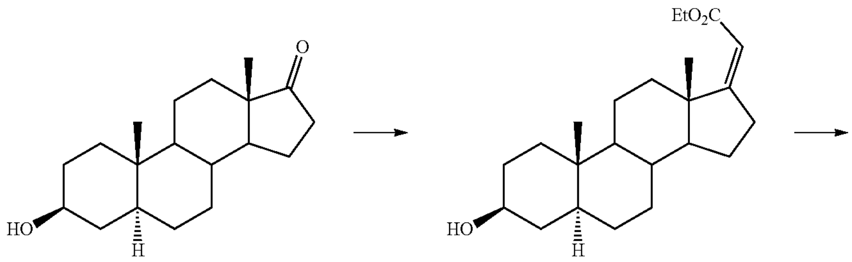

1

2

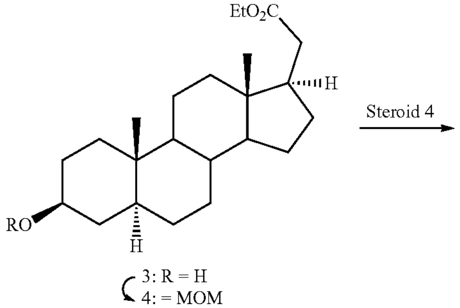

3: R = H
4: = MOM

-continued

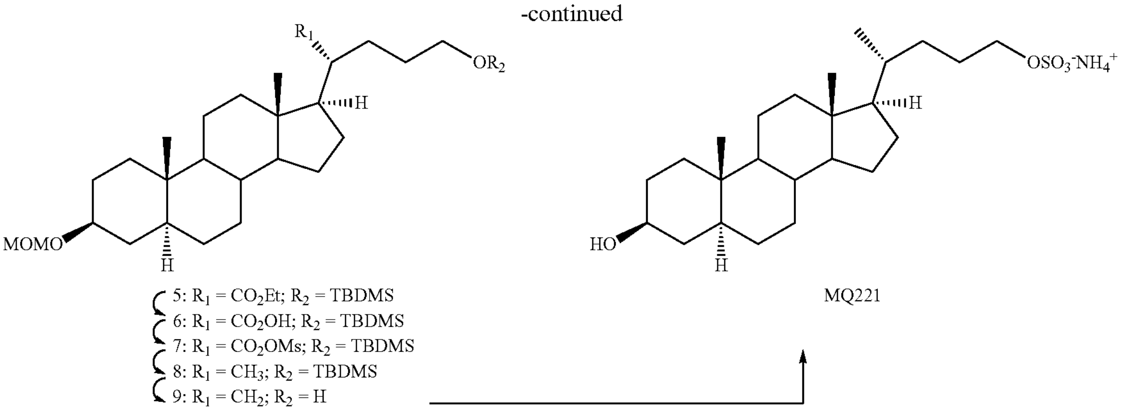

5: $R_1 = CO_2Et$; $R_2$ = TBDMS
6: $R_1 = CO_2OH$; $R_2$ = TBDMS
7: $R_1 = CO_2OMs$; $R_2$ = TBDMS
8: $R_1 = CH_3$; $R_2$ = TBDMS
9: $R_1 = CH_2$; $R_2$ = H

MQ221

Steroid 2

A solution of sodium ethoxide (26 mmol, formed in situ from 598 mg of sodium metal in 20 mL of ethanol) was added dropwise under $N_2$ at 35-40° C. to stirred epiandrosterone (1, 1.8 g, 6.2 mmol) and triethyl phosphonoacetate (5.6 ml, 28 mmol) in anhydrous ethanol (50 mL). After addition, the reaction was refluxed for 16 h. Ethanol was removed under reduced pressure on a rotary evaporator and water was added. The product was extracted into dichloromethane (150 mL×2) and washed with brine (50 mL×2). The extract was dried over anhydrous $Na_2SO_4$, filtered and the solvents removed under reduced pressure on a rotary evaporator. The residue was purified by flash column chromatography (silica gel eluted with 20% EtOAc in hexanes) to give steroid 2 (1.02 g, 46%) which had: $^1H$ NMR (400 MHz, $CDCl_3$) δ 5.48 (t, J=2.0 Hz, 1H), 4.12 (q, J=7.1 Hz, 2H), 3.57-3.49 (m, 1H), 2.79-2.75 (m, 2H), 2.18 (s, 1H), 1.79-0.60 (m, 23H), 0.78 (s, 3H), 0.77 (s, 3H); $^{13}C$ NMR (100 MHz, $CDCl_3$) δ 176.4, 167.4, 108.3, 70.9, 59.4, 54.3, 53.4, 46.2, 44.7, 37.9, 36.9, 35.5, 35.2, 35.1, 31.8, 31.3, 30.3, 28.4, 24.2, 21.0, 18.4, 14.2, 12.2.

Steroid 3

5% Pd/C (400 mg) was added at room temperature to a flask containing steroid 2 (1.02 g, 2.83 mmol) dissolved in EtOAc (60 mL). The flask was evacuated and filled with $H_2$ three times. The hydrogenation was carried out under 50 psi $H_2$ pressure. After 3 h, the mixture was filtered through Celite and washed with EtOAc (200 mL). Solvent was removed under reduced pressure on a rotary evaporator and the residue was purified by flash column chromatography (silica gel eluted with 20% EtOAc in hexanes) to give steroid 3 (1.02 g, 100%) which had: $^1H$ NMR (400 MHz, $CDCl_3$) δ 4.15 (q, J=7.0 Hz, 2H), 3.66-3.56 (m, 1H), 2.38-0.63 (m, 29H), 0.81 (s, 3H), 0.59 (s, 3H); $^{13}C$ NMR (100 MHz, $CDCl_3$) δ 174.0, 71.3, 60.1, 55.3, 54.5, 46.9, 44.9, 42.2, 38.2, 37.4, 37.0, 35.6, 35.5, 35.4, 32.1, 31.5, 28.7, 28.2, 24.5, 20.9, 14.2, 12.6, 12.3.

Steroid 4

Chloromethyl methyl ether (0.5 mL, 6.2 mmol) and $i\text{-}Pr_2NEt$ (2.0 mL, 14 mmol) were added at room temperature to a stirred solution of steroid 3 (1.02 g, 2.82 mmol) in dichloromethane. After 16 h, solvent was removed under reduced pressure on a rotary evaporator and the residue was purified by flash column chromatography (silica gel eluted with 10% EtOAc in hexanes) to give steroid 4 (1.05 g, 92%) which had: $^1H$ NMR (400 MHz, $CDCl_3$) δ 4.62 (s, 2H), 4.08 (q, J=7.1 Hz, 2H), 3.48-3.32 (m, 1H), 3.30 (s, 3H), 2.31-0.57 (m, 29H), 0.76 (s, 3H), 0.53 (s, 3H); $^{13}C$ NMR (100 MHz, $CDCl_3$) δ 137.7, 94.4, 76.1, 59.9, 55.2, 54.9, 54.4, 46.8, 44.8, 42.0, 37.3, 36.9, 35.6, 35.4, 35.2, 35.1, 32.0, 28.6, 28.6, 28.0, 24.4, 20.8, 14.1, 12.5, 12.1.

Steroid 5

Lithium diisopropylamide (4 mL, 2.0 M in THF, 8.0 mmol) and hexamethylphosphoramide (10 mmol, 1.85 mL) were added at −78° C. to a stirred solution of steroid 4 (1.11 g, 2.72 mmol) in THF (50 mL). After 45 min, tert-butyl-(3-iodopropoxy)-dimethylsilane (3.0 g, 10 mmol) in THF (5 mL) was added and the reaction was allowed to warn to room temperature and stirred for 16 h. Water was added and the product was extracted into EtOAc (250 mL×2). The combined extracts were dried over anhydrous $Na_2SO_4$, filtered and the solvents removed under reduced pressure on a rotary evaporator. The residue was purified by flash column chromatography (silica gel eluted with 10% EtOAc in hexanes) to afford steroid 5 (1.21 g, 77%) which had: $^1H$ NMR (400 MHz, $CDCl_3$) δ 4.65 (s, 2H), 4.11-4.05 (m, 2H), 3.61-3.34 (m, 6H), 2.44-0.62 (m, 31H), 0.87 (s, 9H), 0.78 (s, 3H), 0.67 (s, 3H), 0.02 (s, 6H); $^{13}C$ NMR (100 MHz, $CDCl_3$) δ 176.1, 94.4, 76.2, 62.7, 59.7, 55.7, 55.0, 54.3, 52.7, 47.1, 44.8, 42.1, 37.6, 36.9, 35.5, 35.4, 35.2, 32.0, 30.4, 28.7, 28.6, 28.2, 27.0, 25.9 (3×C), 23.7, 21.0, 18.2, 14.2, 12.2, 12.1, −5.4 (2×C).

Steroid 6

Lithium aluminum hydride (2.0 M in THF, 8 mL, 16 mmol) was added at room temperature to a stirred solution of the steroid 5 (1.1 g, 1.9 mmol) in diethyl ether (50 mL). After 2 h, water (0.64 mL), 10% aqueous NaOH (1.28 mL) and water (1.92 mL) were sequentially and slowly added. After stirring for 30 min, the mixture was filter through Celite and the Celite was washed with dichloromethane (200 mL). Solvent was removed under reduced pressure on a rotary evaporator and the residue was purified by flash column chromatography (silica gel eluted with 20% EtOAc in hexanes) to afford steroid 6 (796 mg, 78%) which had: $^1H$ NMR (400 MHz, $CDCl_3$) δ 4.67 (s, 2H), 3.81-3.38 (m, 6H), 3.36 (s, 3H), 1.89-0.59 (m, 28H), 0.90 (s, 9H), 0.80 (s, 3H), 0.67 (s, 3H), 0.05 (s, 6H); $^{13}C$ NMR (100 MHz, $CDCl_3$) δ 94.5, 76.3, 63.6, 62.8, 56.3, 55.1, 54.3, 50.5, 44.8, 42.3, 42.1, 39.4, 37.0, 35.6, 35.4, 35.2, 32.0, 28.8, 28.7, 28.6, 27.6, 25.9 (3×C), 25.1, 24.0, 21.2, 18.3, 12.3, 12.2, −5.3, −5.3.

Steroid 7

Methanesulfonyl chloride (0.23 mL, 3 mmol) and $Et_3N$ (0.56 mL, 4 mmol) were added to a stirred solution of steroid 6 (796 mg, 1.49 mmol) in dichloromethane (30 mL) at 0° C. After 1 h, aqueous $NaHCO_3$ (50 mL) was added and the product was extracted into dichloromethane (100 mL×2).

The combined extracts were dried over anhydrous $Na_2SO_4$, filtered and the solvents removed on a rotary evaporator under reduced pressure. The residue was purified by flash column chromatography (silica gel eluted with 20% EtOAc in hexanes) to give steroid 7 (775 mg, 95%) which had: 1H NMR (400 MHz, $CDCl_3$) δ 4.75 (s, 2H), 4.38-4.35 (m, 1H), 4.29-4.09 (m, 2H), 3.63-3.38 (m, 3H), 3.36 (s, 3H), 2.99 (s, 3H), 1.83-0.59 (m, 27H), 0.89 (s, 9H), 0.80 (s, 3H), 0.68 (s, 3H), 0.04 (s, 6H); $^{13}C$ NMR (100 MHz, $CDCl_3$) δ 94.5, 76.2, 70.1, 63.2, 56.1, 55.1, 54.2, 50.1, 44.8, 42.3, 39.5, 39.3, 37.2, 36.9, 35.5, 35.4, 35.2, 31.9, 28.8, 28.7, 28.6, 27.4, 25.9 (3×C), 25.5, 23.9, 21.1, 18.3, 12.4, 12.2, −5.3 (2×C).

Steroid 8

Lithium aluminum hydride (2.0 M in THF, 4 mL, 8 mmol) was added to a stirred solution of steroid 7 (775 mg, 1.26 mmol) in diethyl ether (50 mL) at room temperature. After 2 h, water (0.64 mL), 10% aqueous NaOH (1.28 mL) and water (1.92 mL) were slowly added sequentially. After stirring for 30 min, the mixture was filter through Celite and the Celite was washed with dichloromethane (150 mL). Solvent was removed under reduced pressure on a rotary evaporator and the residue was purified by flash column chromatography (silica gel eluted with 10% EtOAc in hexanes) to afford steroid 8 (532 mg, 81%) which had: $^1H$ NMR (400 MHz, $CDCl_3$) δ 4.67 (s, 2H), 3.58-3.46 (m, 3H), 3.36 (s, 3H), 1.97-0.59 (m, 31H), 0.89 (s, 9H), 0.80 (s, 3H), 0.64 (s, 3H), 0.04 (s, 6H); $^{13}C$ NMR (100 MHz, $CDCl_3$) δ 94.5, 76.3, 63.7, 56.4, 56.1, 55.0, 54.3, 44.8, 42.5, 40.0, 37.0, 35.6, 35.5, 35.4, 35.2, 32.0, 31.9, 29.4, 28.8, 28.7, 28.1, 25.9 (3×C), 24.2, 21.2, 18.6, 18.3, 12.2, 12.0, −5.28 (2×C).

Steroid 9

Tetra-n-butylammonium fluoride (3 mL, 1.0 M in THF, 3.0 mmol) was added to a stirred solution of steroid 8 (532 mg, 1.02 mmol) in THF (20 mL) at room temperature. After 4 h, the THF was removed under reduced pressure on a rotary evaporator and the residue was purified by flash column chromatography (silica gel eluted with 25% EtOAc in hexanes) to give steroid 9 (336 mg, 81%) which had: $^1H$ NMR (400 MHz, $CDCl_3$) δ 4.64 (s, 2H), 3.57-3.35 (m, 3H), 3.33 (s 3H), 2.17-0.56 (m, 32H), 0.78 (s, 3H), 0.62 (s, 3H); $^{13}C$ NMR (100 MHz, $CDCl_3$) δ 94.3, 76.2, 63.2, 56.3, 56.0, 55.0, 54.2, 44.7, 42.5, 39.9, 36.9, 35.5, 35.5, 35.3, 35.1, 31.9, 31.8, 29.3, 28.7, 28.5, 28.1, 24.1, 21.1, 18.5, 12.1, 12.0.

MQ-221

$SO_3$-$Et_3N$ (209 mg, 1.5 mmol) was added to a stirred solution of steroid 9 (122 mg, 0.3 mmol) in pyridine (5 mL) at room temperature. The reaction was stirred for 16 h. Solvent was removed under reduced pressure on a rotary evaporator and the residue was redissolved in THF (5 mL) and acidified with aqueous 6 N HCl (5 mL). After 2 h, the product was extracted into dichloromethane (50 mL×2). Solvent was removed under reduced pressure on a rotary evaporator and the residue was added to 7 N ammonia in methanol (2 mL) and stirred at 23° C. for 1 h. After solvent removal under reduced pressure on a rotary evaporator, the residue was purified by flash chromatography (silica gel, eluted with 10% MeOH in dichloromethane) to give MQ-221 (75 mg, 54%) which had: mp 176-178° C.; $[\alpha]_D^{20}$+16.7 (c=0.03, MeOH); $^1H$ NMR (400 MHz, DMSO-$d_6$) δ 3.74-3.69 (m, 2H), 3.37-3.30 (m, 1H), 1.89-0.51 (m, 36H), 0.71 (s, 3H), 0.58 (s, 3H); $^{13}C$ NMR (100 MHz, DMSO-$d_6$) δ89.4, 69.2, 66.1, 56.0, 55.8, 53.9, 44.4, 42.2, 39.6, 38.1, 36.7, 35.1, 35.1, 35.0, 31.8, 31.7, 28.5, 27.8, 25.8, 23.9, 20.9, 18.5, 12.1, 11.9.

Example 2: Alternative Synthesis of MQ221

An alternative synthesis for steroid MQ221 is described and shown in the scheme below.

Scheme 2: Alternate Synthesis of MQ-221

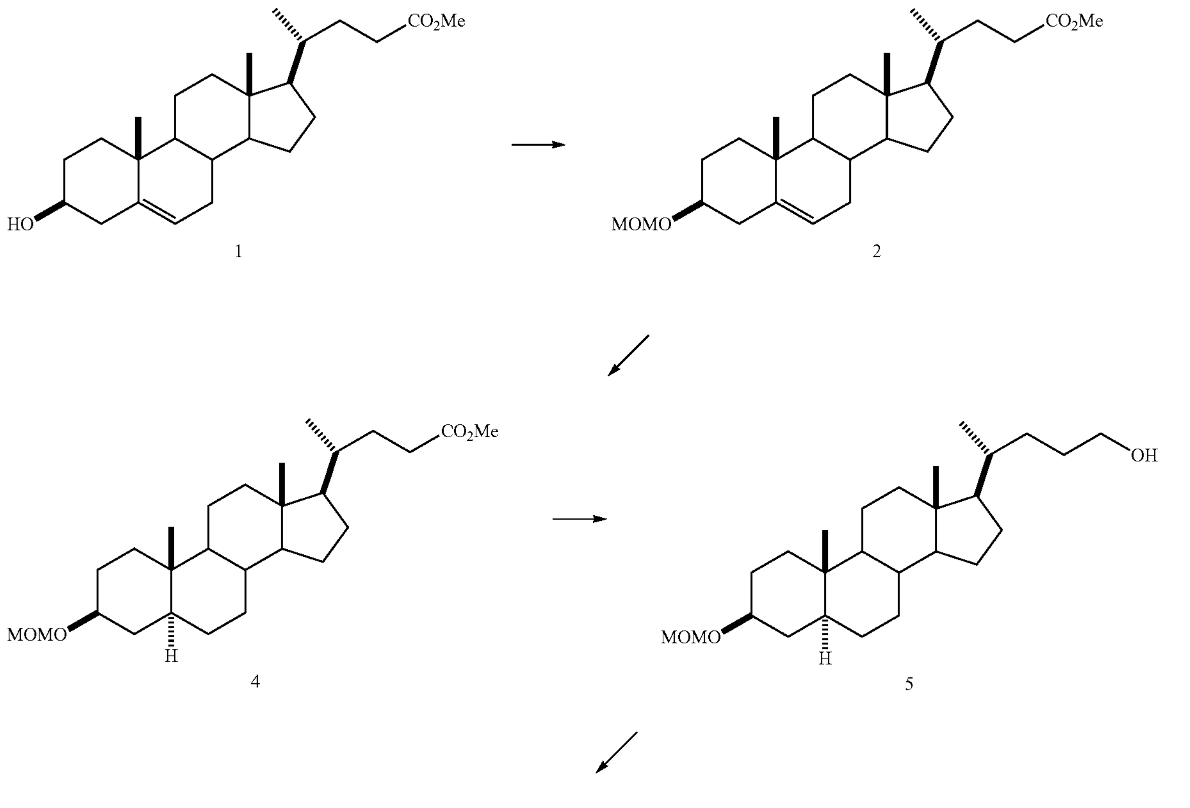

1

2

4

5

-continued

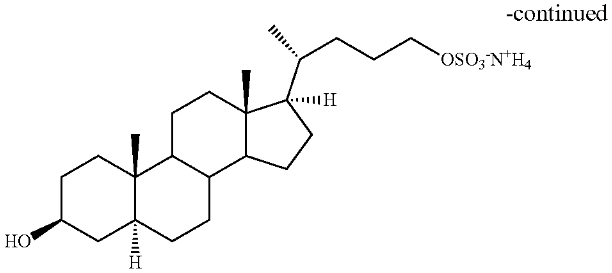

MQ221

Steroid 2

To a solution of 5-cholenic acid-3β-ol, methyl ester (1, 1.26 g, 3.25 mmol) in dichloromethane (30 mL) was added chloromethyl methyl ether (0.50 mL 6.5 mmol) and i-$Pr_2NEt$ (1.4 mL, 10 mmol) at 25° C. After 16 h, solvent was removed under reduced pressure and the residue was purified by flash column chromatography (silica gel eluted with 10% EtOAc in hexanes) to give steroid 2 (1.19 g, 85%): $^1H$ NMR (400 MHz, $CDCl_3$) δ 5.30-5.28 (m, 1H), 4.63 (s, 2H), 3.61 (s, 3H), 3.40-3.32 (m, 1H), 3.31 (s, 3H), 2.34-0.84 (m, 28H), 0.96 (s, 3H), 0.63 (s, 3H); $^{13}C$ NMR (100 MHz, $CDCl_3$) δ 174.4, 140.5, 121.5, 94.5, 76.7, 56.5, 55.6, 54.9, 51.3, 49.9, 42.2, 39.6, 39.4, 37.1, 36.5, 35.2, 31.7, 31.7, 30.8 (2×C), 28.7, 27.9, 24.1, 20.9, 19.2, 18.1, 11.7.

Steroid 4

To a solution of steroid 2 (1.19 g, 2.75 mmol) in EtOAc/MeOH (40 mL/10 mL) was added 10% Palladium on charcoal (200 mg) at 25° C. The hydrogenation flask was evacuated and refilled three times with $H_2$. The hydrogenation was carried out under 55 psi for 6 h. the reaction mixture was filtered through Celite and washed with EtOAc (150 mL). Solvent was removed under reduced pressure and the residue was purified by flash column chromatography (silica gel eluted with 10% EtOAc in hexanes) to give steroid 4 (1.19 g, 100%): $^1H$ NMR (400 MHz, $CDCl_3$) δ 4.74 (s, 2H), 3.66 9s, 3H), 3.53-3.45 (m, 1H), 3.37 (s, 3H), 2.39-0.58 (m, 31H), 0.80 (s, 3H), 0.65 (s, 3H); $^{13}C$ NMR (100 MHz, $CDCl_3$) δ 174.8, 94.5, 76.3, 56.4, 55.9, 55.1, 54.3, 51.5, 44.9, 42.6, 40.0, 37.0, 35.6, 35.5, 35.4, 35.2, 32.0, 31.0, 30.9, 28.8, 28.7, 28.1, 24.1, 21.2, 18.2, 12.2, 12.0.

Steroid 5

To a solution of steroid 4 (1.19 g, 2.74 mmol) in diethyl ether (60 mL) was added lithium aluminum hydride solution (2.0 M in THF, 5 mL, 10 mmol) at room temperature. After 2 h, 0.40 mL of water, 0.80 mL of 10% of NaOH, and 1.20 mL of water were slowly added. After stirring for 1 h, the mixture was filter through Celite and washed with dichloromethane (200 mL). Solvent was removed under reduced pressure and the residue was purified by flash column chromatography (silica gel eluted with 25% EtOAc in hexanes) to afford steroid 5 (1.11 g, 100%): $^1H$ NMR (400 MHz, $CDCl_3$) δ 5.35-5.33 (m, 1H), 4.68 (s, 2H), 3.60 (t, J=6.5 Hz, 2H), 3.58-3.80 (m, 1H), 3.36 (s, 3H), 2.33-0.87 (m, 29H), 1.00 (s, 3H), 0.68 (s, 3H); $^{13}C$ NMR (100 MHz, $CDCl_3$) δ 140.7, 121.7, 94.6, 76.9, 63.6, 56.7, 56.0, 55.1, 50.1, 42.3, 39.7, 39.5, 37.2, 36.7, 35.6, 31.8 (2×C), 29.4, 28.9, 28.2, 24.2, 21.0, 19.3, 18.7, 11.8.

MQ221

To a solution of steroid 5 (768 mg, 1.89 mmol) in pyridine (25 mL) was added $SO_3$-$Me_3N$ (1.39 g, 10 mmol) at room temperature. The mixture was stirred for 16 h. Solvent was removed under reduced pressure and the residue was redissolved in Methanol (10 mL) and then 6 N HCl (10 mL) was added. After 2 h, the product was extracted into dichloromethane (150 mL×4). Solvent was removed under reduced pressure, 7 N ammonia in methanol (6 mL) was added and the reaction was stirred at 23° C. for 1 h. After solvent removal under reduced pressure, the product was purified by flash chromatography (silica gel, eluted with 10%-25% MeOH in dichloromethane) to give MQ221 (710 mg, 82%): mp. 180-182° C.; $[\alpha]_D^{20}$+18.0 (c=0.05, MeOH); $^1H$ NMR (400 MHz, $CD_3OD$) δ 3.99-3.96 (m, 2H), 3.58-3.44 (m, 1H), 2.13-0.82 (m, 36H), 0.84 (3H), 0.71 (s, 3H); $^{13}C$ NMR (100 MHz, $CD_3OD$) δ 70.5, 68.3, 56.5, 56.2, 54.4, 44.8, 42.4, 40.0, 37.5, 36.8, 35.5, 35.4, 35.2, 31.9, 31.7, 30.7, 28.6, 27.8, 25.7, 23.8, 21.0, 17.7, 11.4, 11.1.

Example 3: Synthesis of MQ245

Synthesis for steroid MQ245 is described and shown in the scheme below.

Scheme 3: Synthesis of MQ-245

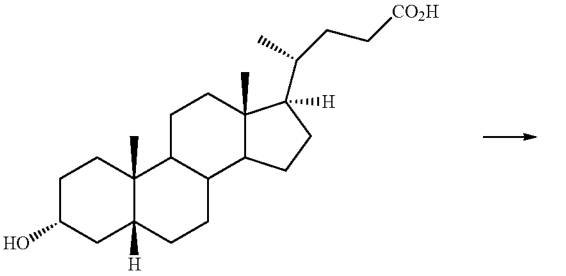

10

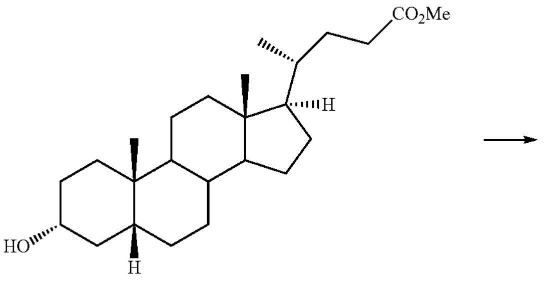

11

-continued

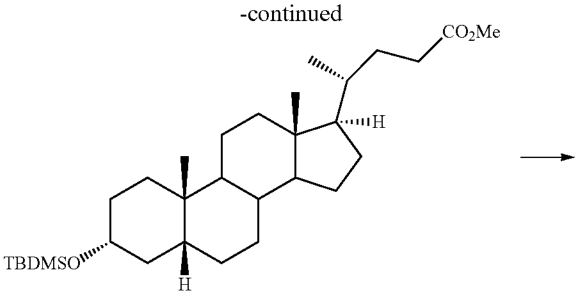

12

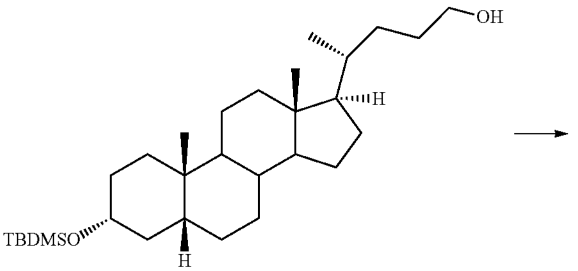

13

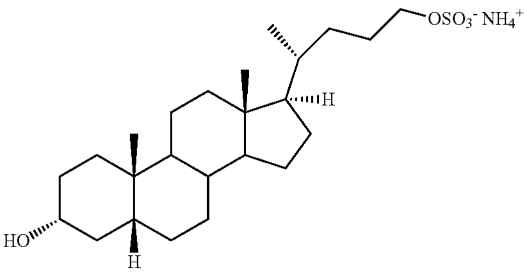

MQ245

Steroid 11

Acetyl chloride (5 mL) was added to a solution of lithocholic acid (10, 1.5 g, 4 mmol) in methanol (40 ml) at room temperature. After 2 h, water was added and the product was extracted into dichloromethane (150 mL×2). The organic layers were washed with aqueous $NaHCO_3$. Solvent was removed under reduced pressure on a rotary evaporator and the residue was purified by flash column chromatograph (25% EtOAc in hexanes) to give lithocholic acid methy ester (11, 1.48 g, 95%): $^{1}$H NMR ($CDCl_3$) 3.59 (s, 3H), 3.56-3.50 (m, 1H), 2.58 (s, 1H), 2.32-0.69 (m, 31H), 0.85 (s, 3H), 0.57 (s, 3H); $^{13}$C NMR ($CDCl_3$) δ 174.6, 71.4, 56.3, 55.8, 51.3, 42.5, 41.9, 40.2, 40.0, 36.2, 35.6, 35.2, 35.1, 34.4, 30.8, 30.8, 30.2, 28.0, 27.0, 26.3, 24.0, 23.2, 20.6, 18.1, 11.8.

Steroid 12

Chloro(dimethyl)(2-methyl-2-propanyl)silane (450 mg, 3 mmol) and imidazole (6 mmol, 408 mg) were added to a stirred solution of steroid 11 (500 mg, 1.28 mmol) in dimethylforamide at room temperature. After 16 h, water was added and the product was extracted into EtOAc (150 mL×2). The organic layers were washed with brine (50 mL×2) dried over anhydrous $Na_2SO_4$, filtered and the solvent was removed under reduced pressure on a rotary evaporator. The residue was purified by flash column chromatograph (10% EtOAc in hexanes) to give steroid 12 (646 mg, 100%): $^{1}$H NMR (400 MHz, $CDCl_3$) 3.66 (d, J=1.1 Hz, 3H), 3.62-3.54 (m, 1H), 2.39-0.73 (m, 33H), 0.89 (m, 12H), 0.63 (s, 3H), 0.06 (s, 3H) 0.06 (s, 3H); $^{13}$C NMR (100 MHz, $CDCl_3$) δ 174.7, 72.8, 56.4, 55.9, 51.4, 42.7, 42.2, 40.2, 40.1, 36.9, 35.8, 35.5, 35.3, 34.5, 31.0, 31.0, 28.2, 27.3, 26.4, 25.9 (3×C), 25.7, 24.2, 23.4, 20.8, 18.3, 18.2, 12.0, −4.6 (2×C).

Steroid 13

Lithium aluminum hydride (1.0 M in THF, 6 mL, 6 mmol) was added to a solution of steroid 12 (646 mg, 1.28 mmol) in diethyl ether (40 mL) at room temperature. After 2 h, water (0.24 mL), 10% aqueous NaOH (0.48 mL) and water (0.72 ml) were slowly added dropwise in a sequential manner. The resultant mixture was stirred at room temperature for 45 min and then filtered through Celite. The Celite was washed with dichloromethane (200 mL). The solvents were removed under reduced pressure on a rotary evaporator and the residue was purified by flash column chromatography (20% EtOAc in hexanes) to give steroid 13 (600 mg, 100%) which had: $^{1}$H NMR (400 MHz, $CDCl_3$) 3.57-3.56 (m, 3H), 2.02-0.71 (m, 32H), 0.89 (s, 3H), 0.87 (s, 9H), 0.62 (s, 3H), 0.04 (s, 6H); $^{13}$C NMR (100 MHz, $CDCl_3$) δ 72.8, 63.3, 56.3, 56.1, 42.6, 42.2, 40.2, 40.1, 36.8, 35.8, 35.5, 35.5, 34.5, 31.8, 30.9, 29.3, 28.2, 27.2, 26.3, 25.9 (3×C), 24.1, 23.3, 20.7, 18.6, 18.2, 11.9, −4.69 (2×C).

MQ-245

$SO_3$-$Me_3N$ (556 mg, 4 mmol) was added to a stirred solution of steroid 13 (300 mg, 0.637 mmol) in pyridine (15 mL) at room temperature. The reaction was stirred for 16 h. Solvent was removed under reduced pressure on a rotary evaporator and the residue was dissolved in methanol (4 mL) and then 6 N HCl (4 mL) was added. After 1 h, the product was extracted into dichloromethane (50 mL×4). Solvent was removed under reduced pressure on a rotary evaporator, 7 N ammonia in methanol (5 mL) was added and the reaction was stirred at 23° C. for 1 h. Solvent was removed under reduced pressure on a rotary evaporator and the residue was purified by flash chromatography (silica gel, eluted with 10%-25% MeOH in dichloromethane) to give MQ-245 (275 mg, 94%) which had: mp 195-197° C.; $[\alpha]_D^{20}$+8.9 (c=0.09, MeOH); $^{1}$H NMR (400 MHz, $CD_3OD$) δ 4.00 (t, J=6.3 Hz, 2H), 3.59-3.53 (m, 1H), 2.06-1.01 (m, 36H), 0.97 (s, 3H), 0.72 (s, 3H); $^{13}$C NMR (100 MHz, $CD_3OD$) δ 72.6, 69.8, 58.1, 57.7, 44.0, 43.7, 42.0, 41.7, 37.4, 37.3, 36.9, 36.6, 35.8, 33.2, 31.3, 29.4, 28.5, 27.8, 27.2, 25.4, 24.1, 22.1, 19.3, 12.7.

Example 4: Synthesis of MQ246

Synthesis for steroid MQ246 is described and shown in the scheme below.

Scheme 4: Synthesis of MQ-246

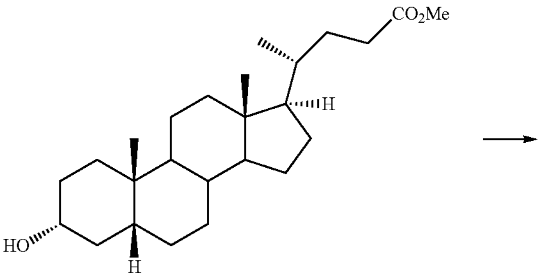

11

-continued

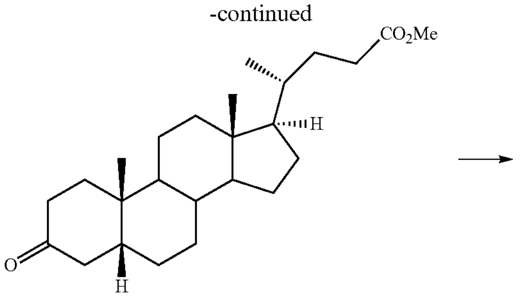

14

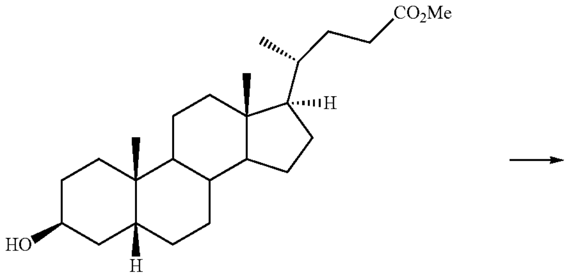

15

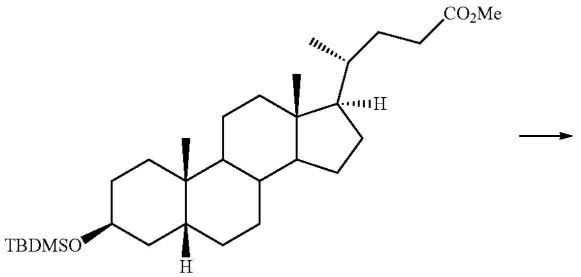

16

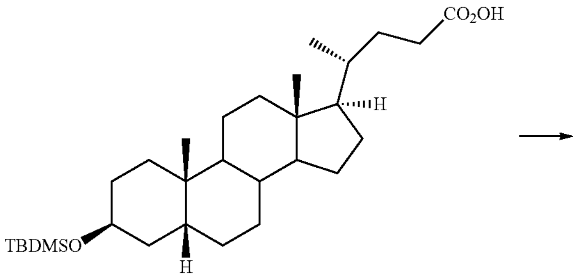

17

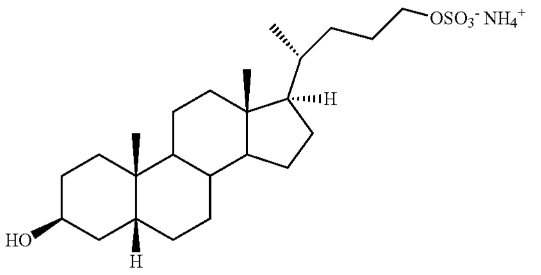

MQ246

Steroid 14

Dess-Martin periodinane (2.12 g, 5 mmol) was added to a stirred solution lithocholic acid methyl ester (11, 1.0 g, 2.56 mmol) at room temperature. After 2 h, water was added and the product was extracted into dichloromethane (150 mL×2). The combined extracts were dried over anhydrous $Na_2SO_4$, filtered and the solvent removed under reduced pressure on a rotary evaporator. The residue was purified by flash column chromatograph (15% EtOAc in hexanes) to give steroid 14 (945 mg, 94%) which had: $^1H$ NMR (400 MHz, $CDCl_3$) δ 3.63 (s, 3H), 2.69-0.72 (m, 31H), 0.99 (s, 3H), 0.65 (s, 3H); $^{13}C$ NMR (100 MHz, $CDCl_3$) δ 213.2, 174.6, 56.3, 55.8, 51.9, 44.2, 42.7, 42.4, 40.6, 39.9, 37.1, 36.9, 35.4, 35.2, 34.8, 30.9, 30.9, 28.0, 26.5, 25.7, 24.0, 22.5, 21.1, 18.2, 12.0.

Steroid 15

K-selectride (1.0 M in THF, 5 mL, 5 mmol) was added to a stirred solution of steroid 14 (945 mg, 2.44 mmol) in THF (930 mL) at −78° C. After 2 h, 3 N aqueous NaOH (10 mL) followed by $H_2O_2$ (3 mL) were added at −78° C. The reaction was then warmed to room temperature and stirring was continued for 45 min. The product was extracted into EtOAc (150 mL×2) and the combined organic layers were washed with brine (50 mL×2), dried over anhydrous $Na_2SO_4$ and filtered. Solvent was removed under reduced pressure on a rotary evaporator and the residue was purified by flash column chromatography (15% EtOAc in hexanes) to give steroid 15 (906 mg, 96%) which had: $^1H$ NMR (400 MHz, $CDCl_3$) δ 4.13-4.10 (m, 1H), 3.66 (s, 3H), 2.36-0.80 (m, 32H), 0.96 (s, 3H), 0.65 (s, 3H); $^{13}C$ NMR (100 MHz, $CDCl_3$) δ 174.7, 67.1, 56.6, 56.0, 51.4, 42.7, 40.2, 39.7, 36.5, 35.6, 35.3, 35.1, 33.5, 31.0, 31.0, 29.9, 28.2, 27.8, 26.6, 26.2, 24.1, 23.9, 21.0, 18.2, 12.0.

Steroid 16

Chloro(dimethyl)(2-methyl-2-propanyl)silane (750 mg, 5 mmol) and imidazole (10 mmol, 680 mg) were added to a stirred solution of steroid 15 (906 mg, 2.32 mmol) in dimethylformide (20 mL) at room temperature. After 16 h, water was added and the product was extracted into EtOAc (150 mL×2). The combined organic layers were washed with brine (50 mL×2), dried over anhydrous $Na_2SO_4$, filtered and solvent was removed under reduced pressure on a rotary evaporator. The residue was purified by flash column chromatography (silica gel eluted with 10% EtOAc in hexanes) to give steroid 16 (1.09 g, 93%) which had: $^1H$ NMR (400 MHz, $CDCl_3$) δ 4.03-4.02 (m, 1H), 3.66 (s, 3H), 2.37-0.92 (m, 31H), 0.88 (s, 12H), 0.54 (s, 3H), 0.01 (s, 6H); $^{13}C$ NMR (100 MHz, $CDCl_3$) δ 174.7, 67.4, 56.7, 56.0, 51.4, 42.8, 40.3, 39.9, 36.5, 35.7, 35.4, 35.0, 34.4, 31.0, 30.0, 28.6, 28.2, 26.9, 26.4, 25.8 (3×C), 25.7, 24.2, 24.0, 21.1, 18.3, 18.1, 12.0, −4.9 (2×C).

Steroid 17

Lithium aluminum hydride (1.0 M in THF, 6 mL, 6 mmol) was added to a stirred solution of steroid 16 (1.09 g, 2.16 mmol) in diethyl ether (60 mL) at room temperature. After 2 h, water (0.24 mL), 10% aqueous NaOH (0.48 mL) and water (0.72 ml) were slowly added dropwise in a sequential manner. The mixture was stirred at room temperature for 45 min then filtered through Celite. The Celite was washed with dichloromethane (200 mL) and the solvents were removed under reduced pressure on a rotary evaporator. The residue was purified by flash column chromatography (silica gel eluted with 20% EtOAc in hexanes) to give steroid 17 (915 mg, 90%) which had: $^1H$ NMR (400 MHz, $CDCl_3$) 4.04-4.03 (m, 1H), 3.65-3.58 (m, 2H), 2.06-0.95 (m, 32H), 0.90 (s, 12H), 0.67 (s, 3H), 0.30 (s, 6H); $^{13}C$ NMR (100 MHz, $CDCl_3$) δ 67.5, 63.6, 56.7, 56.2, 42.7, 40.3, 39.9, 36.5, 35.7, 35.6, 35.0, 34.4, 31.8, 30.0, 29.4, 28.6, 28.3, 26.9, 26.5, 25.8 (3×C), 24.2, 24.0, 21.1, 18.6, 18.1, 12.1, −4.8, −4.9.

MQ-246

$SO_3$-$Me_3N$ (417 mg, 3 mmol) was added to a stirred solution of steroid 17 (213 mg, 0.53 mmol) in pyridine (10 mL) at room temperature. The reaction was stirred for 16 h and the solvent was removed under reduced pressure on a rotary evaporator. The residue was dissolved in methanol (3 mL) and aqueous 6 N HCl (3 mL) was added. After 1 h, the product was extracted into dichloromethane (50 mL×4). Solvent was removed under reduced pressure on a rotary evaporator, 7 N ammonia in methanol (7 mL) was added to the residue and the reaction was stirred at 23° C. for 1 h. After solvent removal under reduced pressure on a rotary evaporator, the residue was purified by flash column chromatography (silica gel eluted with 10%-25% MeOH in dichloromethane) to give MQ-246 (196 mg, 81%) which had: mp 191-193° C.; $[\alpha]_D^{20}$+45.0 (c=0.06, MeOH); $^1$H NMR (400 MHz, $CD_3OD$) δ 4.33-4.27 (m, 1H), 3.55-3.51 (m, 2H), 2.06-0.99 (m, 36H), 0.97 (s, 3H), 0.71 (s, 3H); $^{13}$C NMR ($CD_3OD$) δ 80.5, 63.7, 58.0, 57.8, 44.0, 43.8, 42.0, 41.7, 37.4, 36.6, 35.7, 34.7, 33.3, 30.4, 29.5, 29.0, 28.4, 27.7, 25.4, 24.0, 23.9, 22.1, 19.4, 12.7.

Example 5: Synthesis of MQ254

Synthesis for steroid MQ254 is described and shown in the scheme below.

dichloromethane (50 mL) at room temperature. After 16 h, solvent was removed under reduced pressure on a rotary evaporator and the residue was purified by flash column chromatography (silica gel eluted with 10% EtOAc in hexanes) to give steroid 18 (875 mg, 95%) which had: $^1$H NMR (400 MHz, $CDCl_3$) δ 4.62 (s, 2H), 3.79 (s, 1H), 3.31 (s, 3H), 2.41-2.34 (m, 1H), 2.06-0.93 (m, 21H), 0.81 (s, 3H), 0.77 (s, 3H); $^{13}$C NMR (100 MHz, $CDCl_3$) δ 221.1, 94.5, 71.4, 55.0, 54.3, 51.4, 47.7, 39.6, 35.9, 35.7, 34.9, 33.5, 32.7, 31.5, 30.7, 28.2, 26.2, 21.6, 19.9, 13.7, 11.3.

Steroid 19

Sodium ethoxide (generated in situ from 598 mg of sodium metal, 26 mmol, in 20 mL of ethanol) was added dropwise to a stirred solution of steroid 18 (875 mg, 2.62 mmol) and triethyl phosphonoacetate (5.6 ml, 28 mmol) in anhydrous ethanol (50 mL) under $N_2$ at 35-40° C. After addition, the reaction was refluxed for 16 h. Ethanol was removed under reduced pressure on a rotary evaporator and water was added. The product was extracted into dichloromethane (150 mL×2) and washed with brine (50 mL×2).

Scheme 5: Synthesis of MQ-254

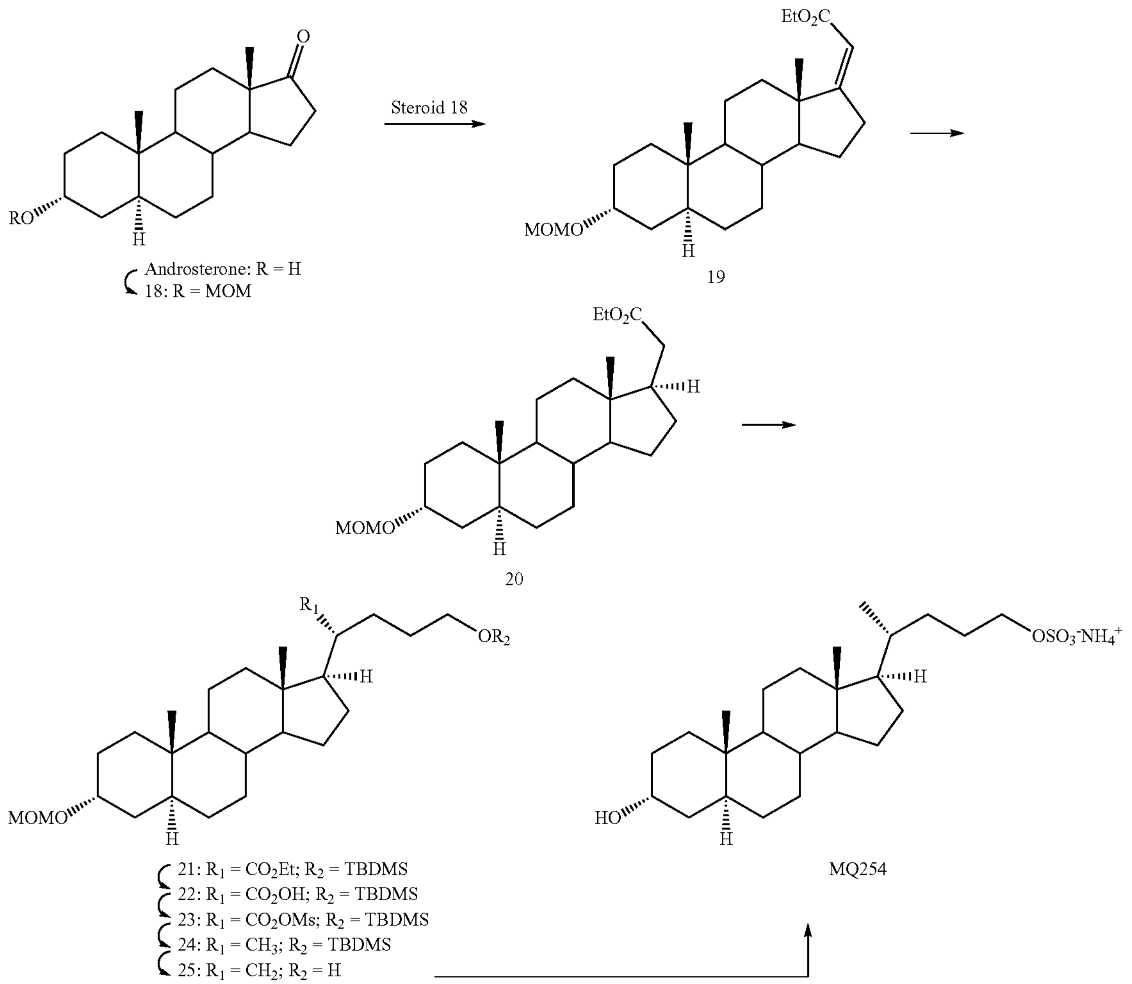

Androsterone: R = H
18: R = MOM

19

20

21: $R_1 = CO_2Et$; $R_2$ = TBDMS
22: $R_1 = CO_2OH$; $R_2$ = TBDMS
23: $R_1 = CO_2OMs$; $R_2$ = TBDMS
24: $R_1 = CH_3$; $R_2$ = TBDMS
25: $R_1 = CH_2$; $R_2$ = H

MQ254

Steroid 18

Chloro(dimethyl)(2-methyl-2-propanyl)silane (0.5 mL, 6.2 mmol) and i-$Pr_2$NEt (2.0 mL, 14 mmol) were added to a stirred solution of androsterone (800 mg, 2.76 mmol) in The extract was dried over anhydrous $Na_2SO_4$, filtered and the solvents removed under reduced pressure on a rotary evaporator. The residue was purified by flash column chromatography (silica gel eluted with 20% EtOAc in hexanes)

to give steroid 19 (805 mg, 76%) which had: $^1H$ NMR (400 MHz, $CDCl_3$) δ 5.44 (s, 1H), 4.59 (s, 2H), 4.08 (q, J=7.1 Hz, 2H), 3.75 (s, 1H), 3.28 (s, 3H), 2.76-2.74 (m, 2H), 1.76-0.74 (m, 23H), 0.74 (s, 6H); $^{13}C$ NMR (100 MHz, $CDCl_3$) δ 176.3, 167.2, 108.2, 94.3, 71.3, 59.2, 54.9, 54.2, 53.5, 46.1, 39.5, 35.8, 35.2, 35.0, 33.4, 32.7, 31.6, 30.2, 28.3, 26.2, 24.1, 20.5, 18.3, 14.2, 11.2.

Steroid 20

5% Pd/C (500 mg) was added to a solution of steroid 19 (805 mg, 2 mmol) in EtOAc (60 mL) at room temperature. The flask was evacuated and charged with $H_2$ three times. The hydrogenation was carried out under 50 psi $H_2$. After 3 h, the reaction was filtered through Celite and the Celite was washed with EtOAc (200 mL). Solvent was removed under reduced pressure on a rotary evaporator and the residue was purified by flash column chromatography (silica gel eluted with 20% EtOAc in hexanes) to give steroid 20 (800 mg, 99%) which had: $^1H$ NMR (400 MHz, $CDCl_3$) δ 4.58 (s, 2H), 4.06-4.00 (m, 2H), 3.75 (s, 1H), 3.29 (s, 3H), 2.29-0.69 (m, 28H), 0.72 (s, 3H), 0.52 (s, 3H); $^{13}C$ NMR (100 MHz, $CDCl_3$) δ 173.6, 94.3, 71.4, 59.8, 55.3, 54.9, 54.4, 46.7, 42.0, 39.6, 37.3, 35.8, 35.4, 35.2, 33.5, 32.7, 31.9, 28.4, 28.0, 26.2, 24.3, 20.3, 14.1, 12.4, 11.2.

Steroid 21

Lithium diisopropylamide (2 mL, 2.0 M in THF, 4.0 mmol) and hexamethylphoramide (6 mmol, 1.08 mL) was added to a stirred solution of steroid 20 (500 mg, 1.23 mmol) in THF (20 mL) at −78° C. After 45 min, tert-butyl-(3-iodopropoxy)-dimethylsilane (900 mg, 3 mmol) in THF (2 mL) was added and the reaction was allowed to warm to room temperature for 16 h. Water was added and the product was extracted into EtOAc (250 mL×2). The combined extracts were dried over anhydrous $Na_2SO_4$, filtered and the solvents removed under reduced pressure on a rotary evaporator. The residue was purified by flash column chromatography (silica gel eluted with 10% EtOAc in hexanes) to afford steroid 21 (635 mg, 89%) which had: $^1H$ NMR (400 MHz, $CDCl_3$) δ 4.66 (s, 2H), 4.11-4.06 (m, 2H), 3.80 (s, 1H), 3.60-3.56 (m, 2H), 3.35 (s, 3H), 2.27-0.69 (m, 31H), 0.87 (s, 9H), 0.76 (s, 3H), 0.67 (s, 3H), 0.02 (s, 6H); $^{13}C$ NMR (100 MHz, $CDCl_3$) δ 176.1, 94.4, 71.6, 62.7, 59.7, 55.8, 55.1, 54.2, 52.7, 47.1, 42.2, 39.7, 37.7, 35.8, 35.4, 33.6, 32.8, 31.9, 30.4, 28.5, 28.3, 27.0, 26.3, 25.9 (3×C), 23.7, 20.6, 18.2, 14.2, 12.2, 11.3, −5.3 (2×C).

Steroid 22

Lithium aluminum hydride (2.0 M in THF, 6 mL, 12 mmol) was added to a stirred solution of steroid 21 (635 mg, 1.1 mmol) in diethyl ether (50 mL) at room temperature. After 2 h, water (0.48 mL), 10% aqueous NaOH (0.96 mL), and water (1.44 mL) of water were slowly added dropwise in sequential order. After stirring for 30 min, the mixture was filter through Celite and the Celite was washed with dichloromethane (200 mL). Solvent was removed under reduced pressure on a rotary evaporator and the residue was purified by flash column chromatography (silica gel eluted with 20% EtOAc in hexanes) to afford steroid 22 (353 mg, 60%) which had: $^1H$ NMR (400 MHz, $CDCl_3$) δ 4.66 (s, 2H), 3.81-3.34 (m, 5H), 3.35 (s, 3H), 1.87-0.72 (m, 29H), 0.88 (s, 9H), 0.77 (s, 3H), 0.66 (s, 3H), 0.04 (s, 6H); $^{13}C$ NMR (100 MHz, $CDCl_3$) δ 94.4, 71.6, 63.6, 62.8, 56.4, 55.1, 54.2, 50.5, 42.7, 42.1, 39.6, 39.5, 37.8, 35.4, 33.6, 32.8, 31.9, 28.8, 28.6, 27.6, 26.3, 25.9 (3×C), 25.2, 24.0, 20.7, 18.3, 12.3, 11.3, −5.4 (2×C).

Steroid 23

Methanesulfonyl chloride (0.16 mL, 2 mmol) and $Et_3N$ (0.42 mL, 3 mmol) were added to a stirred solution of the steroid 22 (353 mg, 0.66 mmol) in dichloromethane (20 mL) at 0° C. After 1 h, aqueous $NaHCO_3$ (50 mL) was added and the product was extracted into dichloromethane (100 mL×2). The combined extracts were dried over anhydrous $Na_2SO_4$, filtered and the solvents removed under reduced pressure on a rotary evaporator. The residue was purified by flash column chromatography (silica gel eluted with 20% EtOAc in hexanes) to give steroid 23 (323 mg, 80%) which had: $^1H$ NMR (400 MHz, $CDCl_3$) δ 4.64 (s, 2H), 4.38-4.35 (m, 1H), 4.15-4.12 (m, 1H), 3.81 (s, 1H), 3.62-3.57 (m, 2H), 3.36 (s, 3H), 2.98 (s, 3H), 1.83-0.72 (m, 28H), 0.88 (s, 9H), 0.77 (s, 3H), 0.67 (s, 3H), 0.03 (s, 6H); $^{13}C$ NMR (100 MHz, $CDCl_3$) δ 94.5, 71.6, 70.1, 63.2, 56.2, 55.1, 54.1, 50.1, 42.3, 39.6, 39.5, 39.3, 37.2, 35.8, 35.4, 33.6, 32.7, 31.8, 28.8, 28.5, 27.4, 26.2, 25.9 (3×), 25.5, 23.9, 20.7, 18.2, 12.4, 11.3, −5.4 (2×C).

Steroid 24

Lithium aluminum hydride (2.0 M in THF, 4 mL, 8 mmol) was added to a stirred solution of steroid 23 (323 mg, 0.526 mmol) in diethyl ether (40 mL) at room temperature. After 2 h, water (0.64 mL), 10% aqueous NaOH (1.28 mL), and water (1.92 mL) were slowly added dropwise in sequential order. After stirring for 30 min, the mixture was filter through Celite and the Celite was washed with dichloromethane (150 mL). Solvent was removed under reduced pressure on a rotary evaporator and the residue was purified by flash column chromatography (silica gel eluted with 10% EtOAc in hexanes) to afford steroid 24 (207 mg, 76%) which had: $^1H$ NMR (400 MHz, $CDCl_3$) δ 4.66 (s, 2H), 3.82 (s. 1H), 3.58-3.55 (m, 2H), 3.37 (s, 3H), 1.97-0.73 (m, 31H), 0.90 (s, 9H), 0.78 (s, 3H), 0.65 (s, 3H), 0.05 (s, 6H); $^{13}C$ NMR (100 MHz, $CDCl_3$) δ 94.5, 76.3, 63.7, 56.4, 56.1, 55.0, 54.3, 44.8, 42.5, 40.0, 37.0, 35.6, 35.5, 35.4, 35.2, 32.0, 31.9, 29.4, 28.8, 28.7, 28.1, 25.9 (3×C), 24.2, 21.2, 18.6, 18.3, 12.2, 12.0, −5.28 (2×C).

Steroid 25

Tetra-n-butylammonium fluoride (1 mL, 1.0 M in THF, 1.0 mmol) was added to a stirred solution of steroid 24 (207 mg, 0.4 mmol) in THF (5 mL) at room temperature. After 16 h, the THF was removed under reduced pressure on a rotary evaporator and the residue was purified by flash column chromatography (silica gel eluted with 25% EtOAc in hexanes) to give steroid 25 (139 mg, 86%); $^1H$ NMR (400 MHz, $CDCl_3$) δ 4.64 (s, 2H), 3.81 (s, 1H), 3.60-3.58 (m, 2H), 3.36 (s 3H), 1.96-0.71 (m, 32H), 0.77 (s, 3H), 0.64 (s, 3H); $^{13}C$ NMR (100 MHz, $CDCl_3$) δ 94.4, 71.6, 63.4, 56.5, 56.0, 55.1, 54.2, 42.5, 39.9, 39.7, 35.8, 35.5, 35.4, 33.6, 32.8, 31.9, 31.8, 29.4, 28.6, 28.2, 26.3, 24.1, 20.7, 18.6, 12.0, 11.3.

MQ-254

$SO_3$-$Et_3N$ (476 mg, 3.42 mmol) was added to a stirred solution of the steroid 25 (139 mg, 0.342 mmol) in pyridine (5 mL) at room temperature. The reaction was stirred for 16 h. Solvent was removed under reduced pressure on a rotary evaporator and the residue was dissolved in THF (5 mL) and acidified with aqueous 6 N HCl (5 mL). After 2 h, the product was extracted into dichloromethane (50 mL×2). Solvent was removed under reduced pressure on a rotary evaporator 7 N ammonia in methanol (3 mL) was added to the residue at 23° C. After stirring for 1 h, solvent was removed under reduced pressure on a rotary evaporator and the residue was purified by flash column chromatography (silica gel eluted with 10% MeOH in dichloromethane) to give MQ-254 (157 mg, 99%) which had: mp 179-181° C.; $[\alpha]_D^{20}$+9.1 (c=0.11, MeOH); $^1H$ NMR (400 MHz, $CD_3OD$) δ 3.99 (s, 2H), 3.72 (s, 1H), 2.05-0.75 (m, 36H), 0.84 (s, 3H), 0.72 (s, 3H); $^{13}C$ NMR (100 MHz, $CD_3OD$) 69.8, 67.4, 58.1, 57.7, 56.0, 55.3, 43.9, 41.6, 40.4, 37.2, 37.0, 36.9, 36.8, 33.6, 33.5, 33.2, 29.9, 29.7, 27.3, 25.3, 22.0, 19.2, 12.7, 11.9.

Example 6: Synthesis of MQ260

Synthesis for steroid MQ260 is described and shown in the scheme below.

Scheme 6: Alternate Synthesis of MQ-260

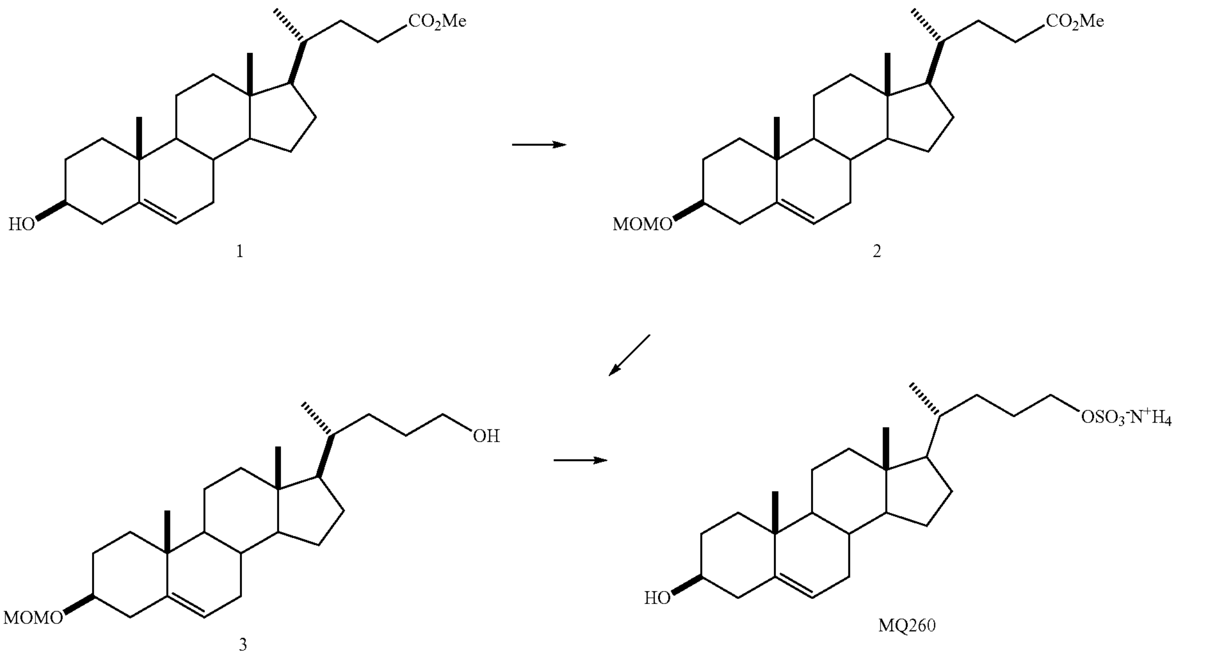

1 2 3 MQ260

Steroid 2

To a solution of 5-cholenic acid-3β-ol, methyl ester (1, 1.26 g, 3.25 mmol) in dichloromethane (30 mL) was added chloromethyl methyl ether (0.50 mL 6.5 mmol) and i-$Pr_2NEt$ (1.4 mL, 10 mmol) at 25° C. After 16 h, solvent was removed under reduced pressure and the residue was purified by flash column chromatography (silica gel eluted with 10% EtOAc in hexanes) to give steroid 2 (1.19 g, 85%): $^1H$ NMR (400 MHz, $CDCl_3$) δ 5.30-5.28 (m, 1H), 4.63 (s, 2H), 3.61 (s, 3H), 3.40-3.32 (m, 1H), 3.31 (s, 3H), 2.34-0.84 (m, 28H), 0.96 (s, 3H), 0.63 (s, 3H); $^{13}C$ NMR (100 MHz, $CDCl_3$) δ 174.4, 140.5, 121.5, 94.5, 76.7, 56.5, 55.6, 54.9, 51.3, 49.9, 42.2, 39.6, 39.4, 37.1, 36.5, 35.2, 31.7, 31.7, 30.8 (2×C), 28.7, 27.9, 24.1, 20.9, 19.2, 18.1, 11.7.

Steroid 3

To a solution of steroid 2 (180 mg, 0.42 mmol) in diethyl ether (20 mL) was added lithium aluminum hydride solution (2.0 M in THF, 2 mL, 4 mmol) at room temperature. After 2 h, 0.16 mL of water, 0.32 mL of 10% aqueous NaOH, and 0.48 mL of water were added slowly. After stirring for 1 h, the mixture was filter through Celite and washed with dichloromethane (200 mL). Solvent was removed under reduced pressure and the residue was purified by flash column chromatography (silica gel eluted with 25% EtOAc in hexanes) to afford steroid 3 (170 mg, 100%): $^1H$ NMR (400 MHz, $CDCl_3$) δ 5.35-5.33 (m, 1H), 4.68 (s, 2H), 3.60 (t, J=6.5 Hz, 2H), 3.58-3.80 (m, 1H), 3.36 (s, 3H), 2.33-0.87 (m, 29H), 1.00 (s, 3H), 0.68 (s, 3H); $^{13}C$ NMR (100 MHz, $CDCl_3$) δ 140.7, 121.7, 94.6, 76.9, 63.6, 56.7, 56.0, 55.1, 50.1, 42.3, 39.7, 39.5, 37.2, 36.7, 35.6, 31.8 (2×C), 29.4, 28.9, 28.2, 24.2, 21.0, 19.3, 18.7, 11.8.

MQ260

To a solution of steroid 3 (170 mg, 0.42 mmol) in pyridine (8 mL) was added $SO_3$-$Me_3N$ (626 mg, 4.5 mmol) at room temperature. The mixture was stirred for 16 h. Solvent was removed under reduced pressure and the residue was redissolved in Methanol (5 mL) and then 6 N HCl (5 mL) was added. After 2 h, the product was extracted into dichloromethane (50 mL×4). Solvent was removed under reduced pressure, 7 N ammonia in methanol (4 mL) was added and the reaction was stirred at 23° C. for 1 h. After solvent removal under reduced pressure, the product was purified by flash chromatography (silica gel, eluted with 10%-25% MeOH in dichloromethane) to give MQ260 (185 mg, 96%): mp 164-166° C.; $[\alpha]_D^{20}$-38.0 (c=0.05, MeOH); $^1H$ NMR (400 MHz, $CD_3OD$) δ 5.39-5.38 (m, 1H), 4.02 (t, J=6.5 Hz, 2H), 3.44-3.34 (m, 1H), 2.27-0.99 (m, 33H), 1.06 (s, 3H), 0.76 (s, 3H); $^{13}C$ NMR (100 MHz, $CD_3OD$) δ 143.2, 122.5, 72.5, 69.8, 58.3, 57.6, 51.8, 43.6, 43.1, 41.3, 38.7, 37.8, 36.9, 33.4, 33.2, 33.1, 32.4, 29.3, 27.2, 25.4, 22.3, 20.0, 19.3, 12.4.

Example 7: Synthesis of Sulfonic Acid Analogue

Synthesis for a sulfonic acid analogue steroid is described below.

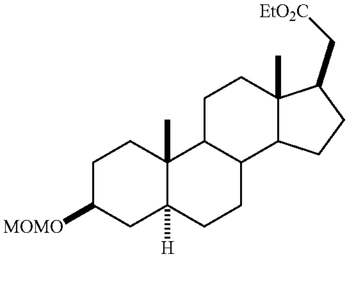

To a solution of olefin (400 mg, 1 mmol) in EtOAc (60 mL) was added 5% Pd/C (200 mg) at room temperature. The flask was evacuated and charged with $H_2$ three time. The hydrogenation was carried out under 50 psi. After 3 h, the mixture was filtered through Celite and washed with EtOAc (200 mL). Solvent was removed under reduced pressure and the residue was purified by flash column chromatography (silica gel eluted with 20% EtOAc in hexanes) to give product (400 mg, 100%): $^{1}$H NMR ($CDCl_3$) δ 4.15 (q, J=7.0, 2H), 3.66-3.56 (m, 1H), 2.38-0.63 (m, 29H), 0.81 (s, 3H), 0.59 (s, 3H); $^{13}$C NMR (100 MHz, $CDCl_3$) δ 174.0, 71.3, 60.1, 55.3, 54.5, 46.9, 44.9, 42.2, 38.2, 37.4, 37.0, 35.6, 35.5, 35.4, 32.1, 31.5, 28.7, 28.2, 24.5, 20.9, 14.2, 12.6, 12.3.

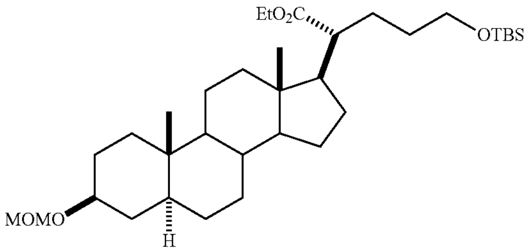

To a solution of the ester (400 mg, 1 mmol) in THF (50 mL) was added LDA (1.25 mL, 2.0 M, 2.5 mmol) and HMPA (3 mmol, 0.54 mL) was added at −78° C. After 45 min, tert-butyl(3-iodopropoxy)dimethylsilane (900 mg, 3 mmol) in THF (5 mL) was added and the mixture was warmed up to room temperature for 16 h. Water was added and extracted with EtOAc (250 mL×2). The combined extracts were dried, filtered and the solvents removed. The residue was purified by flash column chromatography (silica gel eluted with 10% EtOAc in hexanes) to afford product (510 mg, 88%): $^{1}$H NMR (400 MHz, $CDCl_3$) δ 4.65 (s, 2H), 4.11-4.05 (m, 2H), 3.61-3.34 (m, 6H), 2.44-0.62 (m, 31H), 0.87 (s, 9H), 0.78 (s, 3H), 0.67 (s, 3H), 0.02 (s, 6H); $^{13}$C NMR (100 MHz, $CDCl_3$) δ 176.1, 94.4, 76.2, 62.7, 59.7, 55.7, 55.0, 54.3, 52.7, 47.1, 44.8, 42.1, 37.6, 36.9, 35.5, 35.4, 35.2, 32.0, 30.4, 28.7, 28.6, 28.2, 27.0, 25.9 (3C), 23.7, 21.0, 18.2, 14.2, 12.2, 12.1, −5.4 (2C).

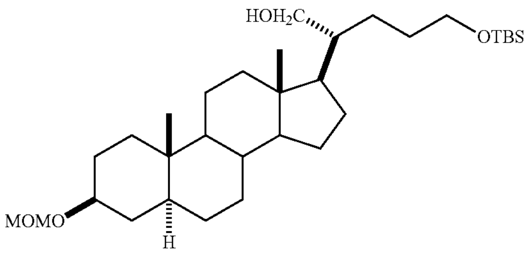

To a solution of the ester (510 mg, 0.88 mmol) in ether (40 mL) was added LAH (2.0 M in THF, 6 mL, 12 mmol) at room temperature. After 2 h, 0.48 mL of water, 0.96 mL of 10% of NaOH, and 1.44 mL of water were slowly added. After stirring for 30 min, the mixture was filter through Celite and washed with dichloromethane (200 mL). Solvent was removed under reduced pressure and the residue was purified by flash column chromatography (silica gel eluted with 20% EtOAc in hexanes) to afford product (216 mg, 46%): $^{1}$H NMR (400 MHz, $CDCl_3$) δ 4.67 (s, 2H), 3.81-3.38 (m, 6H), 3.36 (s, 3H), 1.89-0.59 (m, 28H), 0.90 (s, 9H), 0.80 (s, 3H), 0.67 (s, 3H), 0.05 (s, 6H); $^{13}$C NMR (100 MHz, $CDCl_3$) δ 94.5, 76.3, 63.6, 62.8, 56.3, 55.1, 54.3, 50.5, 44.8, 42.3, 42.1, 39.4, 37.0, 35.6, 35.4, 35.2, 32.0, 28.8, 28.7, 28.6, 27.6, 25.9 (3C), 25.1, 24.0, 21.2, 18.3, 12.3, 12.2, −5.3, −5.3.

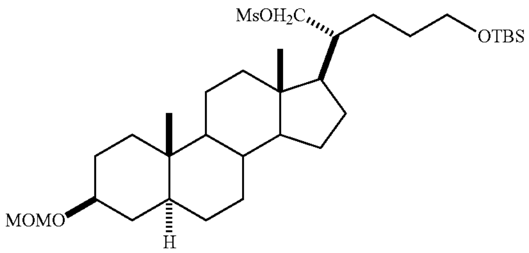

To a solution of the alcohol (216 mg, 0.4 mmol) in dichloromethane (10 mL) was added MsCl (0.08 mL, 1 mmol) and $Et_3N$ (0.28 mL, 2 mmol) at 0° C. After 1 h, aqueous $NaHCO_3$ (50 mL) was added and extracted with dichloromethane (100 mL×2). The combined extracts were dried, filtered and the solvents removed. The residue was purified by flash column chromatography (silica gel eluted with 20% EtOAc in hexanes) to give product (241 mg, 98%): $^{1}$H NMR (400 MHz, $CDCl_3$) δ 4.75 (s, 2H), 4.38-4.35 (m, 1H), 4.29-4.09 (m, 2H), 3.63-3.38 (m, 3H), 3.36 (s, 3H), 2.99 (s, 3H), 1.83-0.59 (m, 27H), 0.89 (s, 9H), 0.80 (s, 3H), 0.68 (s, 3H), 0.04 (s, 6H); $^{13}$C NMR (100 MHz, $CDCl_3$) δ 94.5, 76.2, 70.1, 63.2, 56.1, 55.1, 54.2, 50.1, 44.8, 42.3, 39.5, 39.3, 37.2, 36.9, 35.5, 35.4, 35.2, 31.9, 28.8, 28.7, 28.6, 27.4, 25.9 (3), 25.5, 23.9, 21.1, 18.3, 12.4, 12.2, −5.3 (2C).

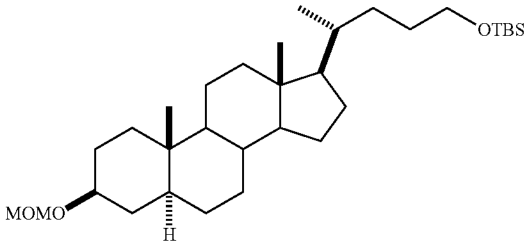

To a solution of the mesylate (241 mg, 0.39 mmol) in ether (40 mL) was added LAH (2.0 M in THF, 4 mL, 8 mmol) at room temperature. After 2 h, 0.64 mL of water, 1.28 mL of 10% of NaOH, and 1.92 mL of water were slowly added. After stirring for 30 min, the mixture was filter through Celite and washed with dichloromethane (150 mL). Solvent was removed under reduced pressure and the residue was purified by flash column chromatography (silica gel eluted with 10% EtOAc in hexanes) to afford product (175 mg, 86%): $^{1}$H NMR (400 MHz, $CDCl_3$) δ 4.67 (s, 2H), 3.58-3.46 (m, 3H), 3.36 (s, 3H), 1.97-0.59 (m, 31H), 0.89 (s, 9H), 0.80 (s, 3H), 0.64 (s, 3H), 0.04 (s, 6H); $^{13}$C NMR (100 MHz, $CDCl_3$) δ 94.5, 76.3, 63.7, 56.4, 56.1, 55.0, 54.3, 44.8, 42.5, 40.0, 37.0, 35.6, 35.5, 35.4, 35.2, 32.0, 31.9, 29.4, 28.8, 28.7, 28.1, 25.9 (3C), 24.2, 21.2, 18.6, 18.3, 12.2, 12.0, −5.28 (2C).

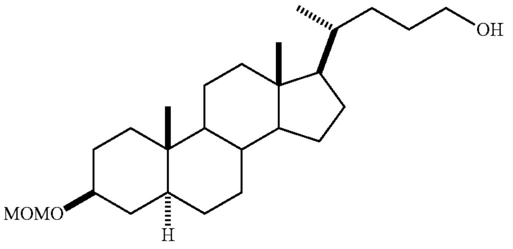

To a solution of TBS ether (175 mg, 0.34 mmol) in THF (5 mL) was added TBAF (1 mL, 1.0 M in THF, 1.0 mmol) at room temperature. After 16 h, THF was removed under reduced pressure and the residue was purified by flash column chromatography (silica gel eluted with 25% EtOAc in hexanes) to give product (133 mg, 95%); $^{1}H$ NMR (400 MHz, $CDCl_3$) δ $^{1}H$ NMR (400 MHz, $CDCl_3$) δ 4.64 (s, 2H), 3.57-3.35 (m, 3H), 3.33 (s 3H), 2.17-0.56 (m, 32H), 0.78 (s, 3H), 0.62 (s, 3H); $^{13}C$ NMR (100 MHz, $CDCl_3$) δ 94.3, 76.2, 63.2, 56.3, 56.0, 55.0, 54.2, 44.7, 42.5, 39.9, 36.9, 35.5, 35.5, 35.3, 35.1, 31.9, 31.8, 29.3, 28.7, 28.5, 28.1, 24.1, 21.1, 18.5, 12.1, 12.0.

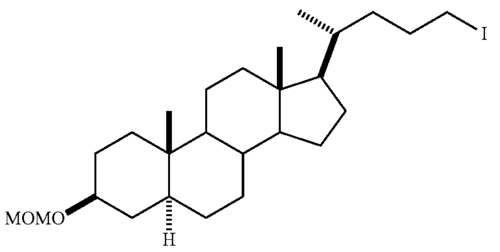

To a solution of the alcohol (133 mg, 0.328 mmol) in benzene (8 mL) and dichloromethane (3 mL) was added $PPh_3$ (524 mg, 2 mmol), imidazole (272 mg, 4 mmol), and $I_2$ (508 mg, 2 mmol) at room temperature. After 3 h, aqueous $NaHCO_3$ (20 mL) and aqueous $Na_2S_2O_3$ (10 mL) were added and the product was extracted into diethyl ether (100 mL×2). Solvent was removed under reduced pressure on a rotary evaporator and the residue was purified by flash column chromatography (silica gel eluted with 4% EtOAc in hexanes) to give the iodo product (165 mg, 98%); $^{1}H$ NMR (400 MHz, $CDCl_3$) δ 4.62 (s, 2H), 3.46-3.40 (m, 1H), 3.30 (s, 3H), 3.13-3.05 (m, 2H), 1.89-0.52 (m, 31H), 0.74 (s, 3H), 0.58 (s, 3H); $^{13}C$ NMR (100 MHz, $CDCl_3$) δ 94.5, 76.3, 56.4, 56.0, 55.1, 54.3, 44.9, 40.0, 37.0, 36.8, 35.5, 35.3, 35.1, 32.1, 30.3, 28.8, 28.7, 28.2, 24.2, 21.2, 18.7, 12.2, 12.1, 2.9.

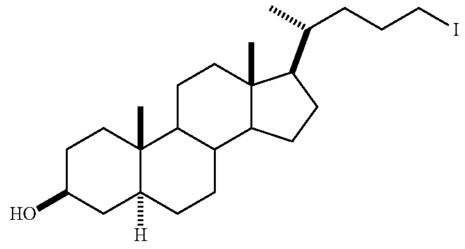 [SMILES: C[C@H](CCCI)[C@H]1CCC2C3CC[C@H]4C[C@@H](O)CC[C@]4(C)C3CC[C@@]21C]

To a solution of the iodo product (165 mg, 0.32 mmol) in methanol (8 mL) was added AcCl (2 mL) at room temperature. After 2 h, water (10 mL) was added and the product was extracted into dichloromethane (100 ml×3), the organic layers were washed with aqueous $NaHCO_3$ (20 mL). Solvent was removed under reduced pressure on a rotary evaporator and the residue was purified by flash column chromatography (silica gel eluted with 25% EtOAc in hexanes) to give the iodo alcohol product (141 mg, 93%); $^{1}H$ NMR (400 MHz, $CDCl_3$) δ 3.60-3.54 (m, 1H), 3.21-3.08 (m, 2H), 1.96-0.58 (m, 32H), 0.79 (s, 3H), 0.64 (s, 3H).

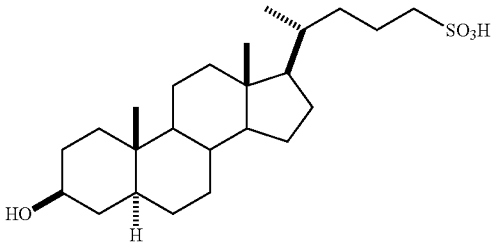 [SMILES: C[C@H](CCCS(=O)(=O)O)[C@H]1CCC2C3CC[C@H]4C[C@@H](O)CC[C@]4(C)C3CC[C@@]21C]

To a solution of the iodo alcohol (141 mg, 0.3 mmol) in ethanol (25 mL) was added sodium sulfite (1.2 g, 9.44 mmol) at room temperature. The mixture was refluxed 48 h. Ethanol was removed and the aqueous layer was acidified with concentrated HCl to pH=1 and the product was extracted into EtOAc (150 mL×3). The organic layers were washed with water (50 mL). Solvent was removed under reduced pressure and the residue was purified by flash column chromatography (silica gel eluted with 10% MeOH in $CH_2Cl_2$) to give product (20 mg, 15%); $^{1}H$ NMR (400 MHz, $CD_3OD$) δ 3.72-3.66 (m, 1H), 2.83-2.80 (m, 2H), 1.91-0.70 (m, 33H), 1.02 (s, 3H), 0.87 (s, 3H).

Example 8: Syntheses of Additional Steroids

Syntheses for various steroids are shown in the schemes below.

Scheme 7

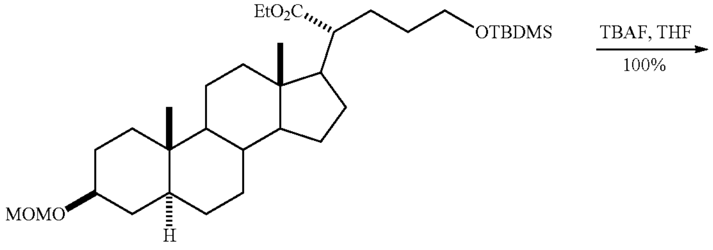

-continued
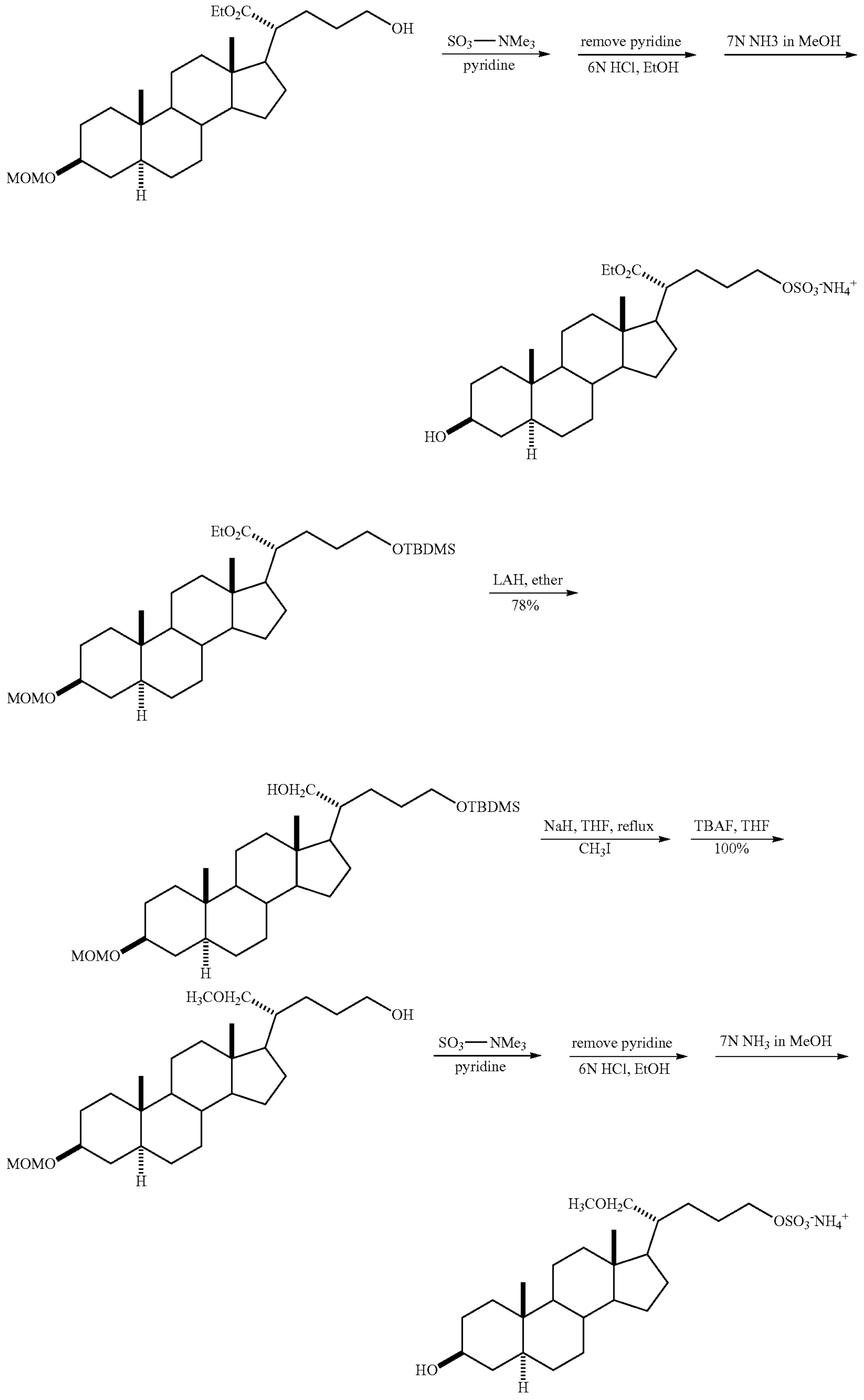

Scheme 8
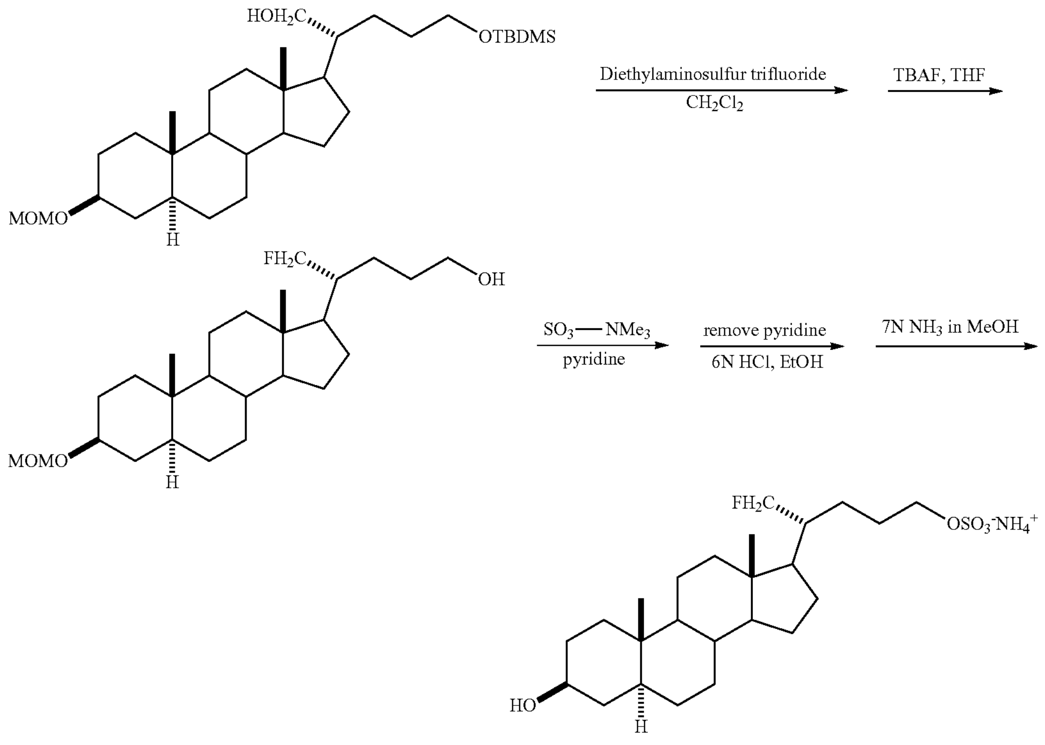
Scheme 9
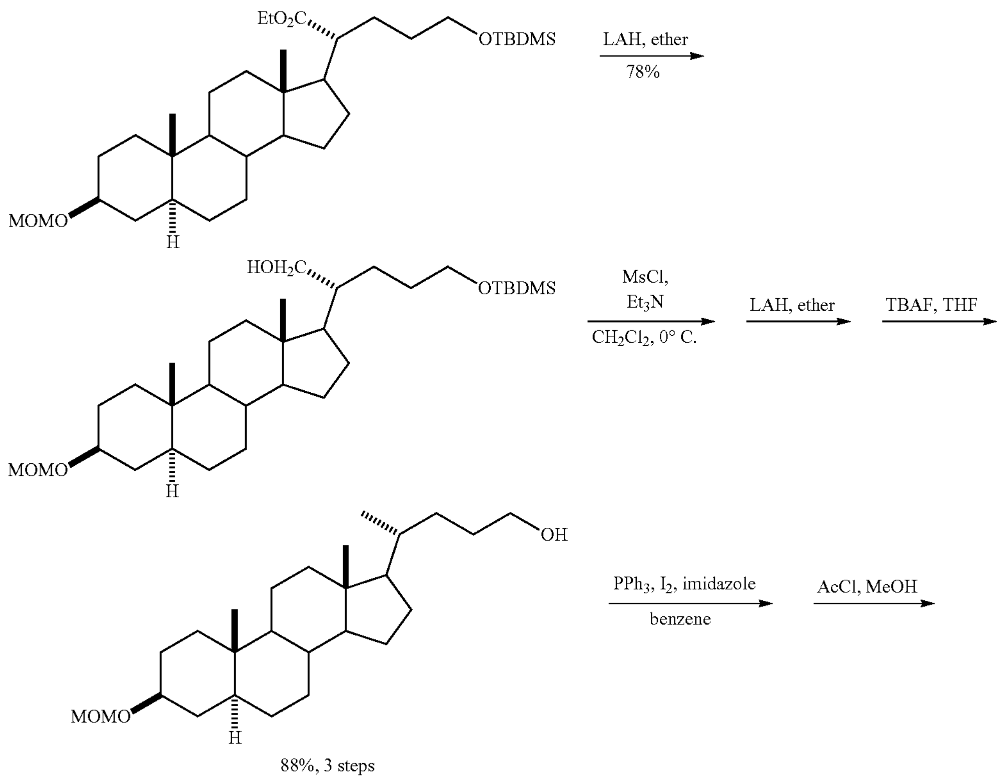

-continued
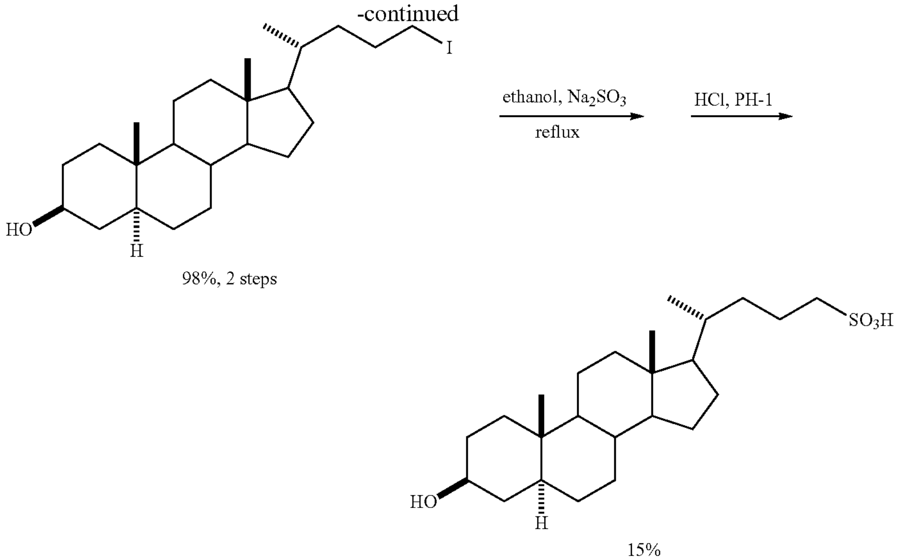
Scheme 10
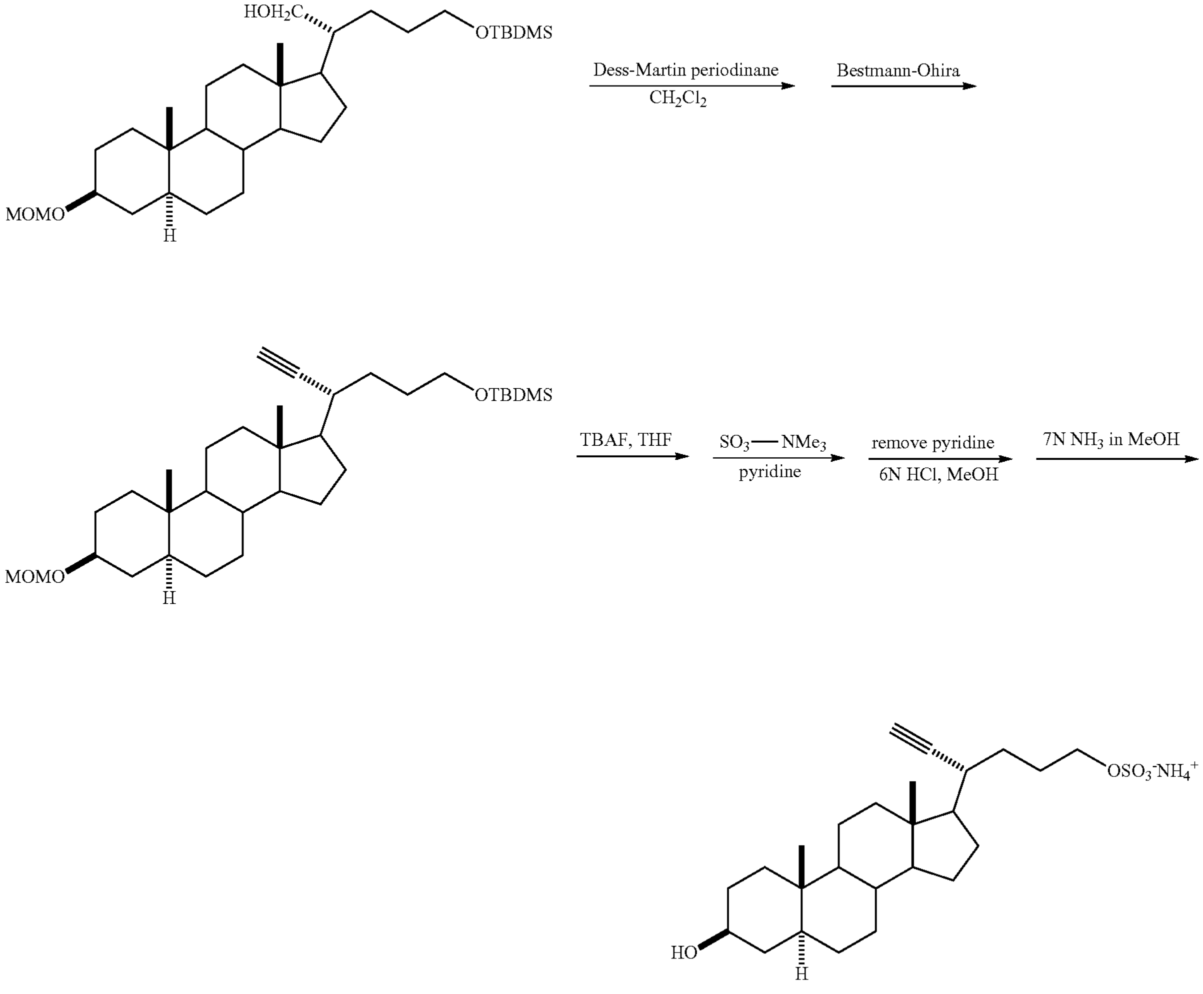

Example 9: A Neurosteroid Analogue with Therapeutically Attractive Features at Ionotropic Neurotransmitter Receptors The pharmacological actions of MQ-221 at NMDA (negative allosteric modulator) and $GABA_A$ (positive allosteric modulator) receptors are shown in FIG. 10. This is an unusual combination of pharmacological actions which raises the possibility that the compound, or analogues of it, can be an effective drug for the treatment of major depressive disorders.

Example 10: A Neurosteroid with Actions at $GABA_A$ and NMDA Receptors

Material and Methods

Hippocampal Cultures.

Hippocampal cultures were maintained as described previously (Mennerick et al., 1995). Hippocampal tissue was harvested from postnatal 1-3 days old male and female Sprague-Dawley rats. A single-cell hippocampal suspension was plated on collagen-coated tissue culture plates and maintained in serum-containing medium on an astrocyte monolayer until use for recording. Recordings were performed 4-7 days after plating for exogenous agonist application and after 9 days for synaptic recordings in order to allow synaptic networks to mature.

N2a Cell Cultures and Transfection.

Murine neuro-2a (N2a; ATCC #CCL-131) cells were plated in Dulbecco's Modified Eagle's medium (DMEM) containing 10% fetal bovine serum, 2 mM glutamine, 100 U/ml penicillin, and 0.1 mg/ml streptomycin and maintained in a 5% $CO_2$ humidified incubator. Cells were transfected with rat GluN1a and GluN2A or GluN2B subunit plasmids (pCDNA3), along with fluorescent protein plasmid to aid identification of transfected neurons, using Lipofectamine 2000 (ThermoFisher) as previously described (Warikoo et al., 2018).

Electrophysiology.

Hippocampal neurons were visualized with phase-contrast optics using an Eclipse TE2000-S inverted microscope. Voltage-clamp data were collected using a Multiclamp 700B amplifier, Digidata 1440 data acquisition board (Molecular Devices), and pClamp 10 software.

For study of exogenous agonist-induced currents, whole-cell pipette solution contained the following (in mM): 130 CsCl, 4 NaCl, 10 HEPES, 5 EGTA, and 0.5 $CaCl_2$). The pH was adjusted to 7.25 with NaOH. Bath perfusion solution for study of NMDA current contained 138 mM NaCl, 4 mM KCl, 10 mM HEPES, 10 mM glucose, 0.2 mM $CaCl_2$), 0 mM $MgCl_2$, 1 μM NBQX, 10 μM glycine or 10 μM D-serine, and 10 μM gabazine. To isolate $GABA_A$R currents and PSCs, 25 μM D-APV was used in place of 10 μM gabazine, and 1 mM $MgCl_2$ was included in the bath. To isolate AMPAR PSCs, 25 μM D-APV was used instead of 1 μM NBQX. For synaptic studies, $Ca^{2+}$ was increased to 2 mM. Whole-cell recording pipettes were pulled from borosilicate capillary glass (World Precision Instruments) and had final open-tip resistances of 3-6 MΩ. Neuron membrane potential was clamped at −70 mV unless otherwise stated. Cells were constantly perfused with bath solution using a gravity-fed local perfusion stream, and drugs were applied by micromanifold with an exchange time of ~100 ms. Transfected N2a cells expressing recombinant NMDAR subunits were recorded as with neurons, except receptor antagonists were omitted.

Data were analyzed using Clampfit 10 (MolecularDevices), processed in Excel spreadsheets (Microsoft), and plotted in Prism 8 (GraphPad). Concentration-response relationships were fit with inhibition or stimulation versions of the Hill equation using GraphPad Prism. Summary data in figures and text are given as mean±SEM. Statistical tests for comparison of means are described in the figure legends and were performed using Graphpad Prism. Comparisons were corrected where relevant for multiple comparisons as described in the legends. Statistical significance was defined as a corrected p-value<0.05. The reported n refers to the number of neurons recorded.

Compounds.

The synthesis of MQ-221, its stereoisomers MQ-245, MQ-246 and MQ-254, along with spectroscopic characterization data are reported above. The compounds were chromatographly pure as determined by thin layer chromatography on silica gel thin layer plates. KK-169 was synthesized as previously described (Chisari et al., 2019). 3α5βPS was obtained from Steraloids. Other salts and drugs were obtained from SigmaMillipore.

Results

Pharmacological Effects on NMDARs and $GABA_A$Rs.

Figure 1:
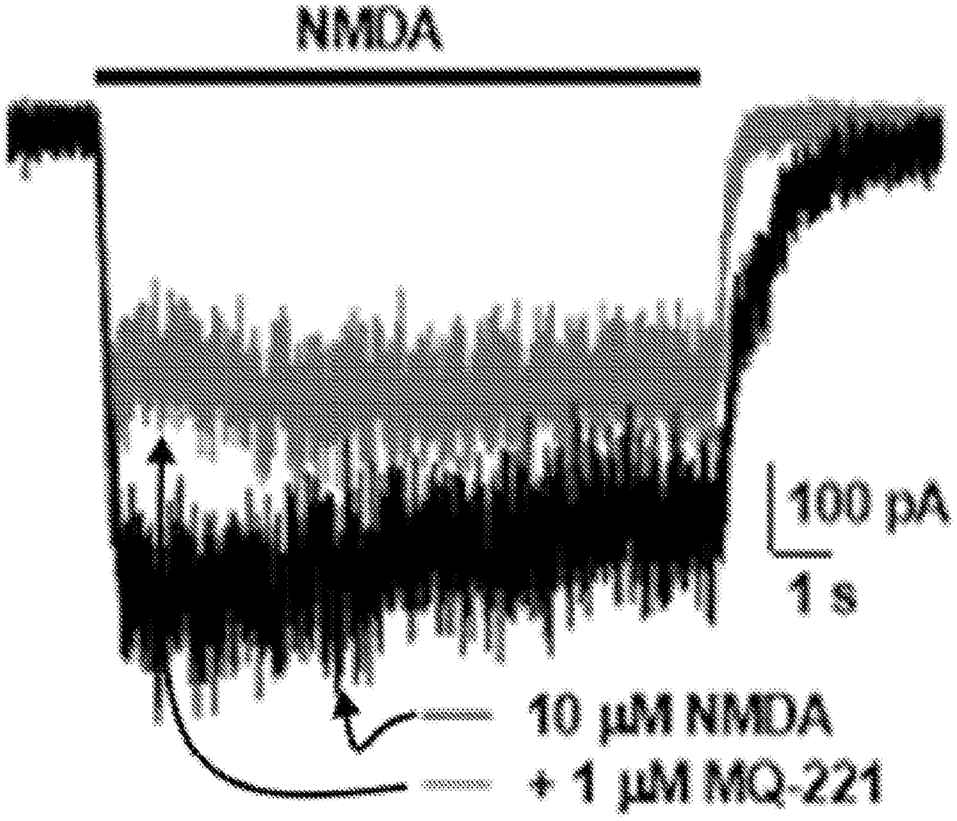
FIG. 1. MQ-221 inhibits NMDAR currents and potentiates initial $GABA_AR$ responses in hippocampal neurons. A-B. Example traces of 10 μM NMDA response with and without 1 μM (A) and 10 μM (B) MQ-221. C. Inhibition of 10 μM NMDA current by 1 μM MQ-221 ($t=11.9$, $p<1\times10^{-4}$, one sample t test) and 10 μM MQ-221 ($t=23.5$, $p<1\times10^{-4}$, one sample t test). The inset shows MQ-221 structure. D-E. Representative neuronal responses to 2 μM GABA with and without 1 μM MQ-221 (D) and 10 μM MQ-221(E). F. Potentiation of peak 2 μM GABA current by 1 μM MQ-221 ($t=4.0$, $p=0.007$, one sample t test) and 10 μM MQ-221 ($t=3.7$, $p=0.021$, one sample t test) is contrasted with lack of effect of 1 μM MQ-221 on steady-state current ($t=1.8$, $p=0.121$, one sample t test) but inhibition by 10 μM MQ-221 ($t=7.8$, $p=0.002$, one sample t test).
Figure 1:
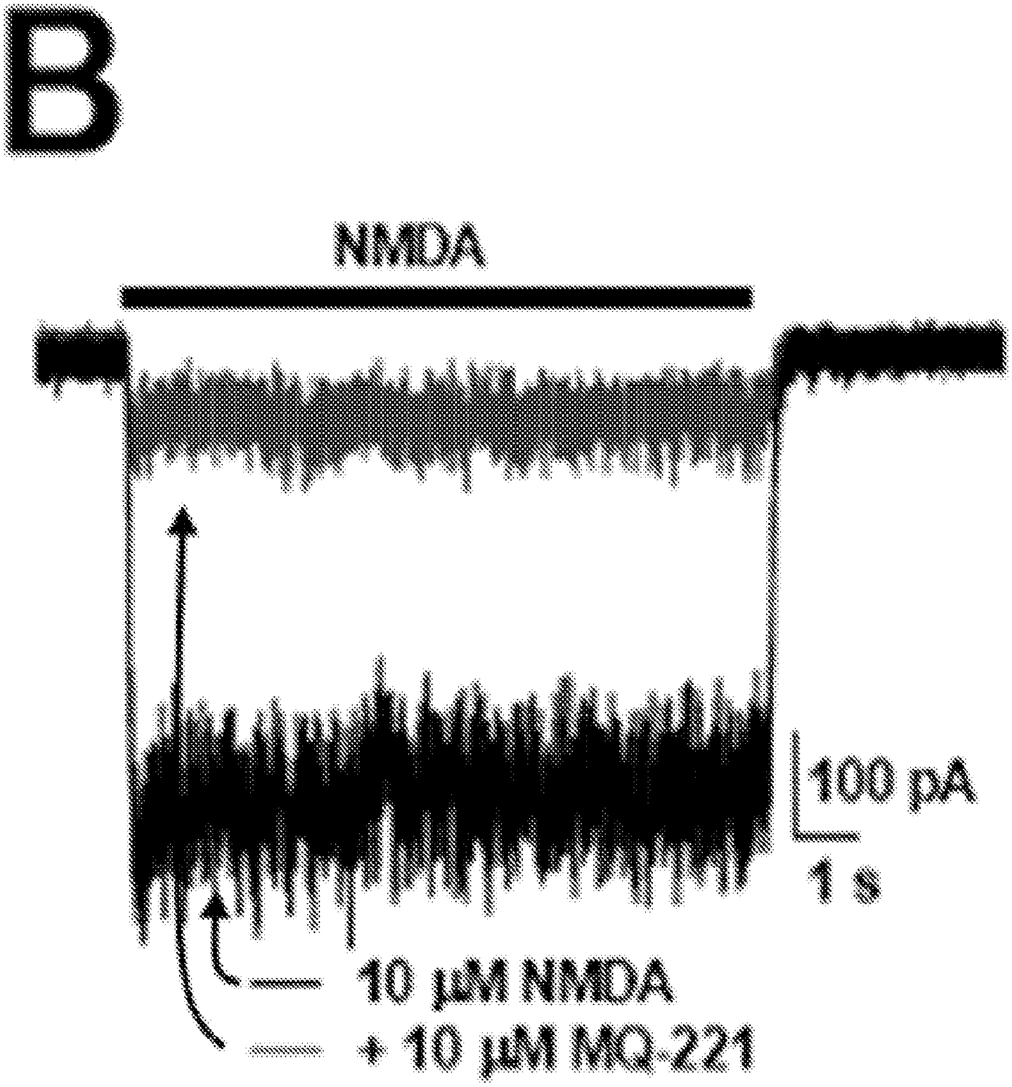
Figure 1:
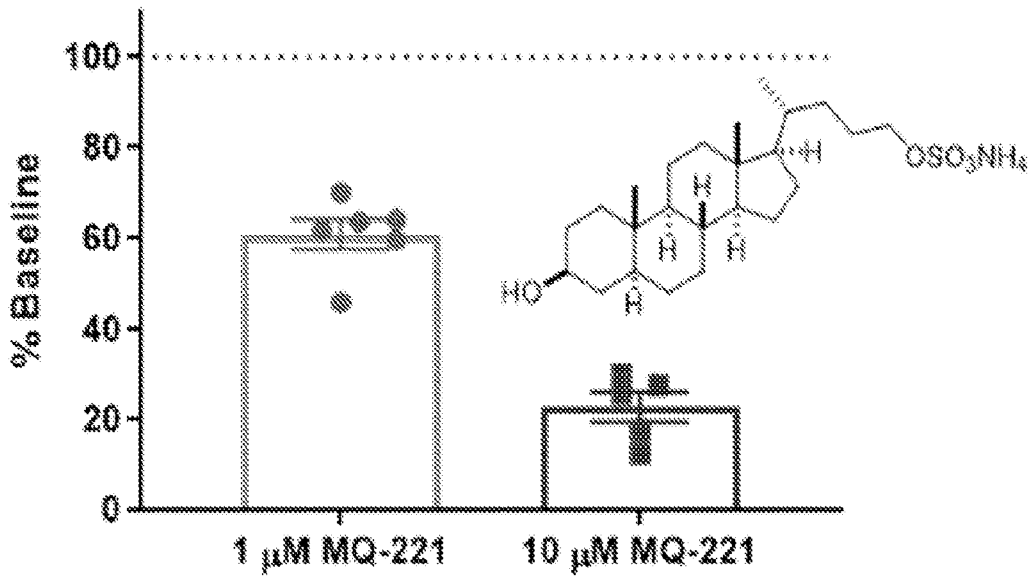
Figure 1:
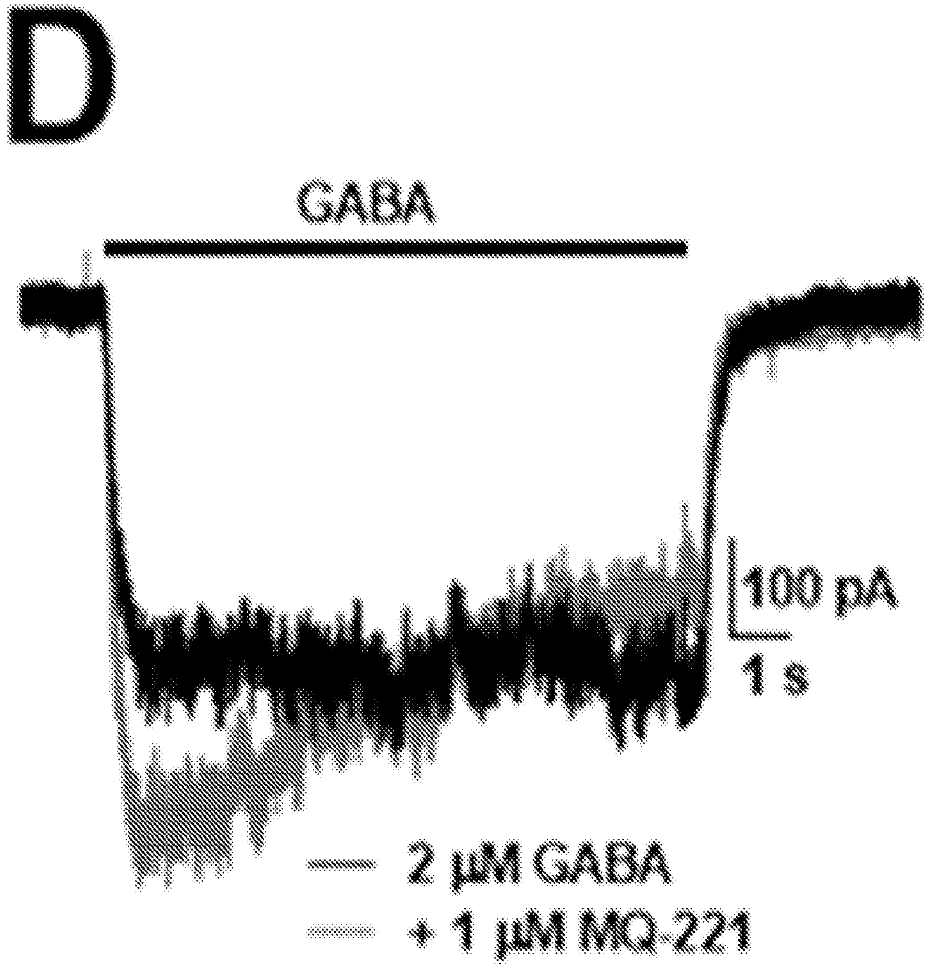
Figure 1:
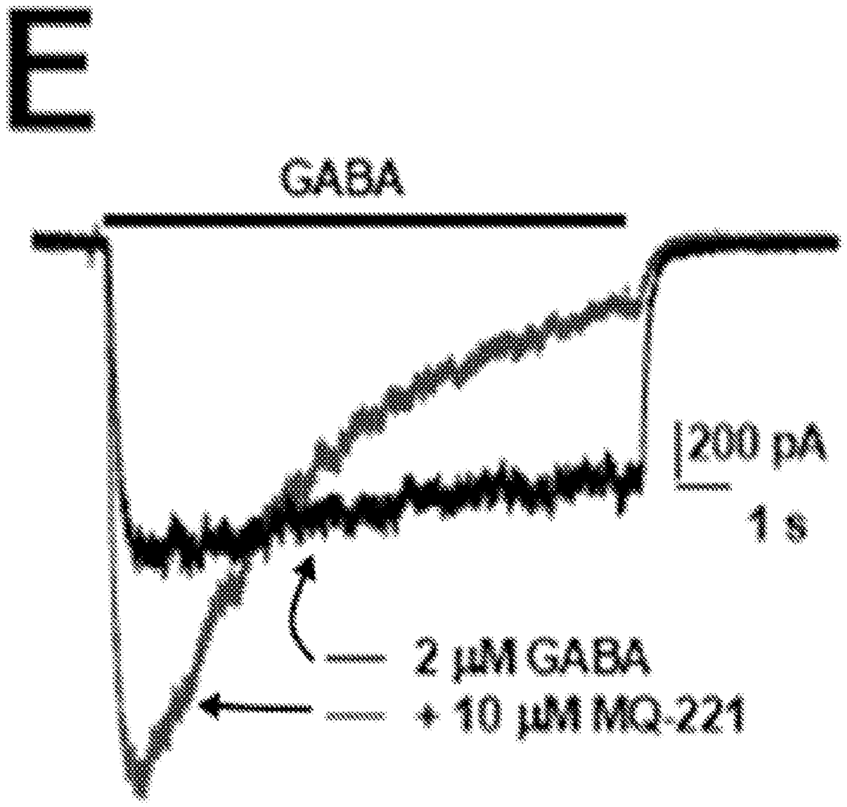
Figure 1:
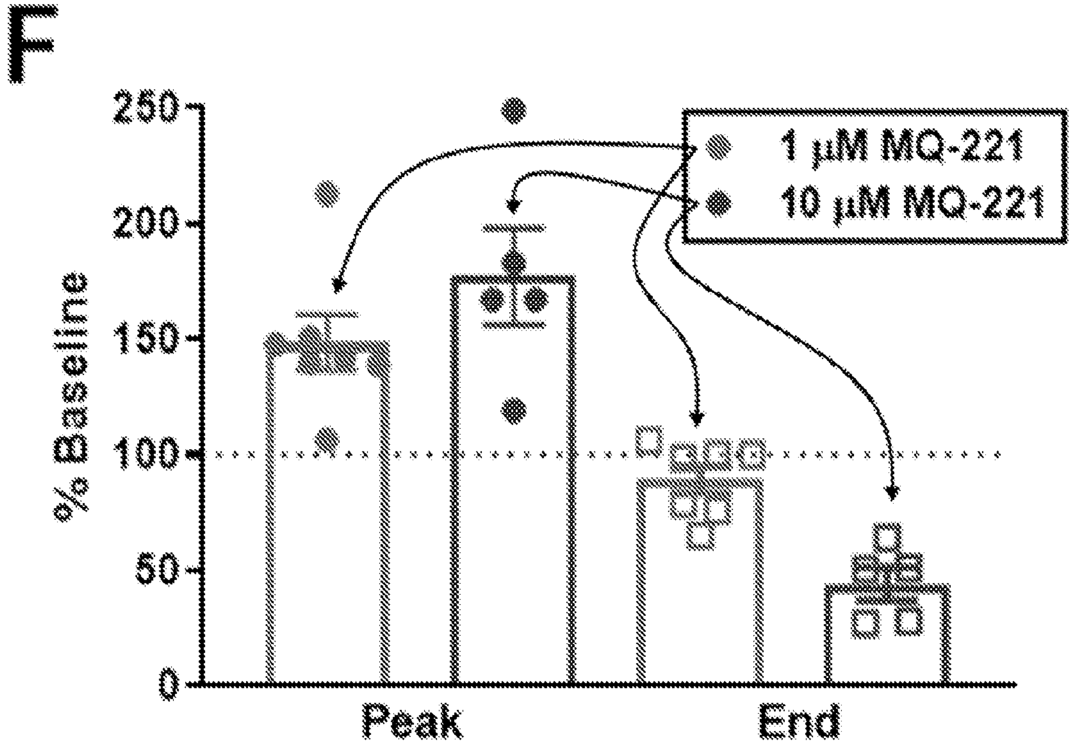

FIG. 1, panels A-C show effects of two concentrations of MQ-221 on NMDAR currents in cultured hippocampal neurons, using 20 s pre-equilibration of MQ-221 prior to co-application with agonist. For NMDAR mediated current, MQ-221 exhibited concentration-dependent inhibition between 1 and 10 μM. This range of effective concentrations places MQ-221 as one of the most potent sulfated steroid analogues at NMDARs, as typically inhibition and potentiation of NMDAR function requires tens of micromolar concentrations for effective modulation (Horak et al., 2004; Park-Chung et al., 1997; Petrovic et al., 2005).

The same concentrations of MQ-221 also potentiated responses of neurons to 2 μM GABA (FIG. 1, panels D-F). At the high concentration there was also evidence of inhibition of GABA current, which we interpret to be similar to the inhibition by negatively charged steroids that we and others have characterized previously, as it primarily affected the late response to GABA (Eisenman et al., 2003) at the higher MQ-221 concentration (FIG. 1, panels D-F).

To ascertain whether MQ-221 is likely to have other targets, we screened for interaction with a subset of other transmitter and hormone receptors present in the Psychoactive Drug Screening Program at the University of North Carolina. The screen, performed at 3 μM MQ-221, failed to clearly identify other targets of MQ-221 (see Table 1).

TABLE 1

| DNA | #1 | I | II | III | IV | AVG | CV |
|---|---|---|---|---|---|---|---|
| 0 | D2 | 193.1 | 165.4 | 164.6 | 176.5 | 174.9 | 0.065804 |
| 0 | D2 | 167.9 | 158.1 | 152.7 | 179.4 | 164.5 | 0.061723 |
| 0 | D2 | 156.2 | 143.1 | 157.8 | 186.1 | 160.8 | 0.097606 |
| 0 | D2 | 181.1 | 154.2 | 151.9 | 151.9 | 159.8 | |
| 0 | D2 | 181.7 | 144.0 | 142.0 | 165.9 | 158.4 | 0.103567 |
| 0 | D2 | 146.0 | 150.2 | 159.0 | 170.6 | 156.4 | 0.0603 |
| 0 | D2 | 165.4 | 142.9 | 139.2 | 169.8 | 154.3 | 0.086956 |
| 0 | D2 | 139.4 | 142.0 | 129.2 | 168.3 | 144.7 | 0.099858 |
| GPR135 | 35 | 0.8 | 10.9 | 1.4 | 0.7 | 3.5 | 1.24455 |
| GPR150 | 116 | 2.0 | 3.7 | 2.6 | 2.3 | 2.6 | |
| GPR32 | 52 | 2.3 | 2.2 | 3.0 | 2.6 | 2.5 | 0.126122 |
| LTB4R | 198 | 1.7 | 1.1 | 1.9 | 4.0 | 2.2 | 0.502143 |
| OPRD1 | 119 | 1.9 | 1.8 | 2.1 | 2.1 | 2.0 | 0.075209 |
| 0 | 256 | 2.6 | 1.3 | 1.3 | 2.5 | 1.9 | 0.318731 |

TABLE 1-continued

| DNA | #1 | I | II | III | IV | AVG | CV |
|---|---|---|---|---|---|---|---|
| GPR151 | 67 | 2.2 | 1.9 | 1.6 | 1.7 | 1.9 | 0.114338 |
| GHRHR | 234 | 3.2 | 0.6 | 2.7 | 0.8 | 1.8 | 0.618834 |
| GPR176 | 12 | 0.9 | 2.7 | 1.1 | 2.6 | 1.8 | 0.466938 |
| GPR62 | 76 | 5.9 | 0.5 | 0.4 | 0.3 | 1.8 | 1.338331 |
| ADRB3 | 33 | 2.8 | 1.0 | 0.7 | 2.3 | 1.7 | 0.522545 |
| FFA2 | 202 | 1.5 | 0.5 | 1.8 | 2.8 | 1.6 | 0.508714 |
| GPR34 | 188 | 0.9 | 1.6 | 1.7 | 2.3 | 1.6 | 0.289315 |
| SSTR3 | 24 | 0.8 | 0.7 | 1.7 | 3.3 | 1.6 | 0.632202 |
| CALCRL | 73 | 2.0 | 0.8 | 1.0 | 2.6 | 1.6 | 0.468484 |
| P2RY14 | 319 | 2.1 | 1.5 | 1.8 | 1.0 | 1.6 | 0.237229 |
| ADRA2B | 113 | 1.8 | 0.9 | 1.7 | 1.8 | 1.6 | 0.236506 |
| MCHR1R | 30 | 1.4 | 2.0 | 1.1 | 1.7 | 1.5 | 0.21355 |
| GPR50 | 68 | 2.7 | 0.8 | 1.3 | 1.2 | 1.5 | 0.480173 |
| ADORA2B | 9 | 1.1 | 2.0 | 1.3 | 1.6 | 1.5 | 0.225832 |
| GPR119 | 3 | 0.8 | 2.2 | 0.8 | 2.1 | 1.5 | 0.434655 |
| TAAR5 | 48 | 2.8 | 0.9 | 0.9 | 1.4 | 1.5 | |
| GRPR | 117 | 0.9 | 1.5 | 2.4 | 1.1 | 1.5 | 0.403958 |
| OXER1 | 215 | 1.9 | 1.4 | 1.3 | 1.2 | 1.5 | 0.201569 |
| GPR61 | 220 | 1.3 | 0.8 | 2.1 | 1.6 | 1.5 | 0.307307 |
| GPR124 | 11 | 0.7 | 1.2 | 2.9 | 0.9 | 1.4 | 0.600923 |
| GPR77 | 277 | 1.8 | 1.4 | 1.0 | 1.6 | 1.4 | 0.205326 |
| PTGDR | 151 | 1.9 | 1.2 | 1.1 | 1.5 | 1.4 | 0.209136 |
| CCR7 | 82 | 1.4 | 1.1 | 2.2 | 1.0 | 1.4 | 0.324403 |
| GPR31 | 180 | 2.3 | 1.3 | 1.1 | 0.9 | 1.4 | 0.374206 |
| P2RY10 | 135 | 1.4 | 1.4 | 1.3 | 1.5 | 1.4 | 0.038742 |
| ADORA1 | 241 | 1.9 | 1.0 | 1.5 | 1.3 | 1.4 | 0.227039 |
| GPR97 | 189 | 1.6 | 1.0 | 0.9 | 2.1 | 1.4 | 0.362727 |
| GNRHR | 66 | 1.5 | 1.0 | 1.8 | 1.1 | 1.4 | 0.250784 |
| HTR4 | 182 | 1.0 | 1.3 | 1.2 | 2.0 | 1.4 | 0.267525 |
| LPAR2 | 6 | 1.1 | 1.3 | 2.0 | 1.1 | 1.4 | 0.273368 |
| CCR6 | 153 | 0.5 | 1.9 | 0.9 | 2.1 | 1.4 | 0.502745 |
| SCTR | 144 | 1.5 | 1.4 | 0.8 | 1.7 | 1.4 | 0.261821 |
| MC5R | 222 | 0.7 | 0.7 | 0.8 | 3.2 | 1.3 | 0.807842 |
| SSTR4 | 152 | 0.7 | 1.5 | 1.7 | 1.4 | 1.3 | 0.275777 |
| P2RY2 | 231 | 1.3 | 1.2 | 1.3 | 1.4 | 1.3 | 0.051169 |
| MRGPRX1 | 142 | 1.1 | 1.0 | 1.6 | 1.7 | 1.3 | 0.227788 |
| DRD1 | 146 | 1.6 | 1.0 | 1.2 | 1.4 | 1.3 | 0.185084 |
| GPR44 | 212 | 1.3 | 1.1 | 1.2 | 1.6 | 1.3 | 0.129535 |
| S1PR4 | 296 | 1.4 | 1.5 | 1.3 | 1.0 | 1.3 | 0.150525 |
| QRFP | 79 | 1.3 | 1.9 | 1.0 | 0.9 | 1.3 | 0.300423 |
| CMKLR1 | 106 | 1.1 | 0.8 | 1.7 | 1.6 | 1.3 | 0.291934 |
| HTR2C VSV | 94 | 1.0 | 1.1 | 2.1 | 0.9 | 1.3 | 0.375405 |
| NPBW1 | 95 | 1.0 | 1.2 | 1.4 | 1.4 | 1.3 | 0.140279 |
| GPR116 | 195 | 1.9 | 1.2 | 0.8 | 1.2 | 1.3 | 0.324674 |
| MCHR2R | 134 | 1.1 | 1.3 | 1.1 | 1.5 | 1.3 | 0.11582 |
| GRM8 | 237 | 1.2 | 1.1 | 1.6 | 1.2 | 1.3 | 0.141962 |
| CALCRb | 65 | 1.0 | 0.9 | 1.7 | 1.5 | 1.3 | 0.266974 |
| ADRB1 | 169 | 1.4 | 1.0 | 1.7 | 0.9 | 1.3 | 0.250578 |
| CCRL2 | 90 | 1.4 | 1.5 | 0.9 | 1.3 | 1.3 | 0.191032 |
| CCR8 | 10 | 0.7 | 1.5 | 1.3 | 1.5 | 1.2 | 0.244505 |
| CHRM1 | 98 | 0.8 | 1.2 | 0.5 | 2.4 | 1.2 | 0.568002 |
| GPR56 | 253 | 0.9 | 1.0 | 1.5 | 1.6 | 1.2 | 0.231642 |
| 0 | 248 | 1.6 | 1.3 | 1.1 | 0.9 | 1.2 | 0.210728 |
| GPR141 | 315 | 1.2 | 1.0 | 1.3 | 1.5 | 1.2 | 0.149612 |
| CHRM2 | 313 | 1.1 | 1.0 | 1.5 | 1.3 | 1.2 | 0.158398 |
| GPR152 | 124 | 1.0 | 1.0 | 1.2 | 1.7 | 1.2 | 0.210287 |
| GRM4 | 301 | 1.6 | 2.0 | 0.7 | 0.7 | 1.2 | 0.452666 |
| SSTR1 | 200 | 0.9 | 1.2 | 1.5 | 1.3 | 1.2 | 0.178122 |
| PTGER2 | 88 | 1.0 | 1.1 | 1.1 | 1.7 | 1.2 | 0.207687 |
| HTR1D | 254 | 1.2 | 1.6 | 1.1 | 1.0 | 1.2 | 0.182465 |
| HTR1F | 270 | 2.2 | 0.5 | 0.8 | 1.4 | 1.2 | 0.534308 |
| NPS | 103 | 0.8 | 1.7 | 1.4 | 0.9 | 1.2 | 0.282619 |
| GPR182 | 276 | 1.1 | 1.0 | 1.2 | 1.5 | 1.2 | 0.13987 |
| FPR1 | 50 | 1.0 | 1.0 | 1.7 | 1.2 | 1.2 | 0.246018 |
| ADRA2A | 161 | 1.4 | 1.2 | 1.4 | 0.8 | 1.2 | 0.197796 |
| GMR2 | 171 | 1.5 | 0.9 | 1.1 | 1.4 | 1.2 | 0.207216 |
| MC3Rb | 22 | 0.9 | 1.1 | 1.4 | 1.4 | 1.2 | 0.175501 |
| AVPR1A | 49 | 1.1 | 1.5 | 0.7 | 1.4 | 1.2 | 0.272814 |
| CHRM3 | 242 | 1.1 | 1.0 | 1.4 | 1.2 | 1.2 | 0.132133 |
| P2RY6 | 239 | 1.2 | 1.1 | 1.3 | 1.1 | 1.2 | 0.072532 |
| AVPR1B | 57 | 2.9 | 0.8 | 0.8 | 0.2 | 1.2 | 0.86314 |
| GRM5 | 221 | 1.1 | 1.3 | 1.0 | 1.4 | 1.2 | 0.13781 |
| GPR171 | 4 | 1.3 | 1.1 | 1.1 | 1.2 | 1.2 | 0.0775 |
| CCKBR | 297 | 1.3 | 1.1 | 1.2 | 1.1 | 1.2 | 0.071123 |
| DRD2 | 154 | 0.8 | 0.9 | 1.9 | 1.1 | 1.2 | 0.381195 |
| EDNRA | 178 | 1.1 | 1.1 | 1.2 | 1.2 | 1.2 | 0.045132 |
| CCR5 | 145 | 1.6 | 1.0 | 1.0 | 1.1 | 1.2 | 0.217414 |
| NMUR2 | 87 | 0.8 | 0.9 | 1.1 | 1.9 | 1.2 | 0.347465 |

TABLE 1-continued

| DNA | #1 | I | II | III | IV | AVG | CV |
|---|---|---|---|---|---|---|---|
| GPR161 | 260 | 1.2 | 1.1 | 1.1 | 1.3 | 1.2 | 0.054633 |
| GPR26 | 172 | 0.9 | 1.4 | 1.2 | 1.1 | 1.2 | 0.168241 |
| GPR83 | 93 | 1.4 | 1.1 | 0.9 | 1.2 | 1.2 | 0.145304 |
| GPR120 | 155 | 0.9 | 2.3 | 0.5 | 0.9 | 1.2 | 0.58295 |
| BDKBR1 | 121 | 1.0 | 1.1 | 1.1 | 1.4 | 1.2 | 0.118673 |
| KISSPEPTIN | 69 | 1.3 | 0.7 | 0.7 | 1.8 | 1.2 | 0.413931 |
| CASR | 137 | 1.3 | 0.8 | 1.3 | 1.1 | 1.1 | 0.172092 |
| AVPR2 | 273 | 0.9 | 1.3 | 1.3 | 1.0 | 1.1 | 0.156273 |
| S1PR1 | 192 | 0.8 | 1.1 | 1.2 | 1.5 | 1.1 | 0.210744 |
| GPR39 | 85 | 0.9 | 1.0 | 1.2 | 1.4 | 1.1 | 0.189065 |
| MC1R | 126 | 0.8 | 1.1 | 1.6 | 1.0 | 1.1 | 0.254228 |
| CXCR6 | 18 | 1.8 | 1.3 | 0.6 | 0.9 | 1.1 | 0.395889 |
| P2RY11 | 31 | 1.5 | 1.3 | 0.9 | 0.8 | 1.1 | 0.231375 |
| GPR153 | 244 | 1.1 | 1.1 | 1.2 | 1.2 | 1.1 | 0.037216 |
| GPR78 | 21 | 1.1 | 1.1 | 1.3 | 1.0 | 1.1 | 0.121123 |
| GPR132 | 84 | 1.1 | 1.2 | 0.8 | 1.3 | 1.1 | 0.164627 |
| P2RY4 | 264 | 1.4 | 0.9 | 1.3 | 0.9 | 1.1 | 0.210044 |
| MRGPRF | 263 | 1.1 | 1.4 | 0.9 | 1.0 | 1.1 | 0.153724 |
| GPR160 | 75 | 1.1 | 1.2 | 1.2 | 1.0 | 1.1 | 0.065318 |
| GPR84 | 165 | 1.3 | 1.2 | 1.0 | 1.0 | 1.1 | 0.123395 |
| PTGIR | 63 | 1.5 | 0.7 | 0.9 | 1.3 | 1.1 | 0.284362 |
| LPAR1 | 310 | 1.0 | 0.8 | 1.1 | 1.5 | 1.1 | 0.238599 |
| SUCNR1 | 40 | 1.2 | 1.1 | 1.1 | 1.0 | 1.1 | 0.078356 |
| LPA4 | 302 | 2.6 | 0.5 | 0.5 | 0.7 | 1.1 | 0.807352 |
| GPR37 | 300 | 1.1 | 1.2 | 1.2 | 1.0 | 1.1 | 0.065198 |
| GPR133 | 27 | 0.8 | 1.0 | 1.0 | 1.6 | 1.1 | 0.261772 |
| CXCR2 | 258 | 1.2 | 1.1 | 1.0 | 1.1 | 1.1 | 0.052589 |
| GABBR1 | 107 | 0.9 | 1.4 | 1.0 | 1.0 | 1.1 | 0.164224 |
| MRGPRE | 230 | 1.0 | 2.0 | 0.9 | 0.5 | 1.1 | 0.52613 |
| NPBW2 | 279 | 0.8 | 1.2 | 1.4 | 1.0 | 1.1 | 0.199996 |
| GPR113 | 187 | 1.1 | 0.9 | 1.1 | 1.3 | 1.1 | 0.119534 |
| GPR4 | 308 | 1.0 | 1.0 | 1.4 | 0.9 | 1.1 | 0.192705 |
| NTSR2 | 111 | 1.8 | 0.8 | 0.9 | 0.9 | 1.1 | 0.374031 |
| CXCR4 | 266 | 0.9 | 1.1 | 1.4 | 1.0 | 1.1 | 0.174742 |
| GPR65 | 269 | 1.1 | 1.2 | 1.1 | 0.9 | 1.1 | 0.079561 |
| TAAR8 | 56 | 0.9 | 1.2 | 1.2 | 1.1 | 1.1 | 0.107981 |
| HRH1 | 317 | 1.3 | 0.9 | 1.1 | 1.0 | 1.1 | 0.115745 |
| GPR110 | 283 | 1.4 | 1.3 | 0.8 | 0.9 | 1.1 | 0.225667 |
| GPRC5D | 205 | 1.1 | 1.1 | 1.1 | 1.0 | 1.1 | 0.034702 |
| FSHR | 218 | 1.1 | 1.1 | 1.0 | 1.0 | 1.1 | 0.036122 |
| FPR3 | 243 | 1.1 | 1.2 | 1.0 | 1.1 | 1.1 | 0.067824 |
| GPR19 | 284 | 1.0 | 1.0 | 1.1 | 1.2 | 1.1 | 0.079245 |
| ADORA3 | 249 | 1.3 | 1.1 | 1.0 | 0.9 | 1.1 | 0.109466 |
| CNR1 | 225 | 1.0 | 1.1 | 1.0 | 1.2 | 1.1 | 0.074615 |
| CXCR5 | 274 | 1.0 | 1.4 | 0.8 | 1.1 | 1.1 | 0.206363 |
| MRGPRG | 238 | 1.0 | 0.8 | 1.4 | 1.0 | 1.1 | 0.188951 |
| F2R | 298 | 1.0 | 1.1 | 1.0 | 1.2 | 1.1 | 0.075955 |
| DRD4 | 83 | 0.5 | 0.6 | 1.8 | 1.4 | 1.1 | 0.492377 |
| PTH1R | 71 | 0.9 | 1.3 | 1.2 | 0.8 | 1.1 | 0.174845 |
| HTR7 | 294 | 1.0 | 1.0 | 1.1 | 1.2 | 1.1 | 0.059651 |
| LTB4R2B | 318 | 1.1 | 1.1 | 1.1 | 1.0 | 1.1 | 0.026709 |
| ADRA1A | 89 | 0.7 | 1.4 | 1.0 | 1.0 | 1.1 | 0.222773 |
| PTAFR | 272 | 1.3 | 1.3 | 1.0 | 0.7 | 1.1 | 0.242225 |
| MRGPRX3 | 46 | 1.1 | 0.5 | 1.7 | 0.9 | 1.1 | 0.396906 |
| CCR2 | 2 | 0.4 | 1.1 | 1.4 | 1.2 | 1.1 | 0.353473 |
| GPR22 | 28 | 1.2 | 1.1 | 0.8 | 1.1 | 1.1 | 0.134955 |
| CCR3 | 305 | 1.1 | 1.1 | 1.0 | 1.0 | 1.1 | 0.047282 |
| ADRA1B | 97 | 1.0 | 1.1 | 0.9 | 1.2 | 1.0 | 0.107087 |
| GPR111 | 74 | 0.3 | 0.6 | 0.9 | 2.3 | 1.0 | 0.742581 |
| GPR1 | 267 | 1.3 | 1.0 | 1.1 | 0.8 | 1.0 | 0.15398 |
| MRGPRX2 | 271 | 1.2 | 1.1 | 1.0 | 0.9 | 1.0 | 0.09595 |
| TACR1 | 312 | 1.0 | 1.0 | 1.0 | 1.1 | 1.0 | 0.051604 |
| GPR18 | 227 | 1.1 | 0.9 | 1.0 | 1.1 | 1.0 | 0.082281 |
| P2RY8 | 168 | 1.0 | 1.1 | 1.1 | 1.0 | 1.0 | 0.02341 |
| ADRA1D | 105 | 0.8 | 1.3 | 1.1 | 1.0 | 1.0 | 0.177833 |
| CHRM4 | 217 | 0.7 | 0.8 | 0.9 | 1.7 | 1.0 | 0.353922 |
| GLP1R | 163 | 1.1 | 1.2 | 0.9 | 1.0 | 1.0 | 0.128792 |
| GPR148 | 59 | 1.1 | 1.4 | 0.9 | 0.8 | 1.0 | 0.22457 |
| GPR35 | 196 | 1.0 | 1.1 | 0.9 | 1.1 | 1.0 | 0.065713 |
| MRGPRX4 | 150 | 1.4 | 0.8 | 0.9 | 1.0 | 1.0 | 0.215114 |
| FFA3 | 210 | 1.1 | 1.0 | 1.0 | 1.0 | 1.0 | 0.043118 |
| PK1 | 39 | 0.7 | 1.3 | 1.1 | 1.1 | 1.0 | 0.182837 |
| VIPR2 | 80 | 1.0 | 1.1 | 0.7 | 1.3 | 1.0 | 0.195342 |
| CYSLTR1 | 26 | 0.8 | 0.9 | 1.1 | 1.3 | 1.0 | 0.177026 |
| TAAR6 | 304 | 1.0 | 1.0 | 1.1 | 1.1 | 1.0 | 0.070777 |
| CYSLTR2 | 170 | 0.9 | 1.6 | 1.0 | 0.6 | 1.0 | 0.369071 |
| GLP2R | 259 | 1.1 | 1.4 | 0.8 | 0.8 | 1.0 | 0.25714 |
| CRHR2 | 122 | 1.5 | 0.7 | 0.9 | 1.0 | 1.0 | 0.280868 |

TABLE 1-continued

| DNA | #1 | I | II | III | IV | AVG | CV |
|---|---|---|---|---|---|---|---|
| HTR2B | 278 | 0.9 | 1.1 | 1.0 | 1.1 | 1.0 | 0.075657 |
| GPR144 | 43 | 1.5 | 0.7 | 0.9 | 1.1 | 1.0 | 0.308044 |
| GPRC5A | 29 | 1.0 | 0.9 | 1.2 | 1.0 | 1.0 | 0.094862 |
| GPRC5B | 197 | 2.4 | 0.6 | 0.4 | 0.7 | 1.0 | 0.791451 |
| NMBR | 54 | 0.4 | 0.6 | 1.6 | 1.5 | 1.0 | 0.510351 |
| GPR63 | 228 | 1.1 | 0.9 | 1.1 | 1.0 | 1.0 | 0.080309 |
| GPR88 | 181 | 1.4 | 0.9 | 1.1 | 0.7 | 1.0 | 0.243516 |
| GPR115 | 291 | 1.0 | 1.0 | 1.0 | 1.1 | 1.0 | 0.038223 |
| F2R-L1 | 186 | 1.1 | 0.7 | 0.9 | 1.3 | 1.0 | 0.227209 |
| GPR17 | 268 | 0.9 | 0.9 | 1.1 | 1.3 | 1.0 | 0.161256 |
| GPR173 | 156 | 0.6 | 1.0 | 1.1 | 1.4 | 1.0 | 0.267707 |
| MLNR | 38 | 0.7 | 1.6 | 0.7 | 1.1 | 1.0 | 0.349875 |
| F2RL3 | 194 | 0.8 | 0.8 | 1.1 | 1.2 | 1.0 | 0.161785 |
| GPR101 | 275 | 1.2 | 1.2 | 0.6 | 1.0 | 1.0 | |
| P2RY1 | 223 | 0.8 | 1.0 | 1.1 | 1.1 | 1.0 | 0.104642 |
| OXTR | 23 | 0.6 | 1.4 | 1.4 | 0.6 | 1.0 | 0.383038 |
| NPY2R | 191 | 1.1 | 1.0 | 0.9 | 1.1 | 1.0 | 0.086489 |
| GPR87 | 293 | 1.1 | 1.1 | 1.0 | 0.8 | 1.0 | 0.128936 |
| C3AR1 | 129 | 0.7 | 1.2 | 0.6 | 1.4 | 1.0 | 0.337176 |
| GPR123 | 307 | 0.9 | 1.2 | 0.9 | 1.0 | 1.0 | 0.114586 |
| NTSR1 | 287 | 1.0 | 1.0 | 1.0 | 1.0 | 1.0 | 0.014823 |
| HTR1E | 262 | 0.9 | 1.0 | 1.0 | 1.1 | 1.0 | 0.061991 |
| TACR2 | 224 | 0.7 | 0.4 | 1.0 | 1.8 | 1.0 | 0.517104 |
| GPR158 | 140 | 1.0 | 1.0 | 1.2 | 0.8 | 1.0 | 0.128268 |
| NPY4R | 78 | 2.5 | 0.3 | 0.5 | 0.7 | 1.0 | 0.881896 |
| GPR183 | 235 | 1.3 | 0.4 | 0.8 | 1.4 | 1.0 | 0.387574 |
| AGTR2 | 257 | 1.1 | 1.0 | 0.9 | 1.0 | 1.0 | 0.072912 |
| GPR3 | 292 | 1.1 | 0.8 | 1.0 | 1.1 | 1.0 | |
| HCA2 | 309 | 0.8 | 0.9 | 1.0 | 1.1 | 1.0 | 0.121476 |
| GRM7 | 229 | 1.0 | 1.4 | 0.9 | 0.7 | 1.0 | 0.249065 |
| CCKAR | 289 | 0.9 | 1.0 | 1.1 | 0.9 | 1.0 | 0.075527 |
| UTS2R | 72 | 0.8 | 1.0 | 0.9 | 1.2 | 1.0 | 0.132537 |
| PTGER3 | 176 | 1.1 | 0.8 | 1.0 | 0.9 | 1.0 | 0.102191 |
| HTR2A | 174 | 0.9 | 1.0 | 1.1 | 0.9 | 1.0 | 0.090936 |
| TA1 | 208 | 0.9 | 1.0 | 1.1 | 1.0 | 1.0 | 0.052531 |
| GPR82 | 285 | 1.2 | 1.0 | 0.9 | 0.8 | 1.0 | 0.172106 |
| PTGER4 | 280 | 0.8 | 1.3 | 1.2 | 0.6 | 1.0 | 0.286847 |
| GPRC6A | 101 | 1.1 | 0.9 | 0.9 | 0.9 | 1.0 | 0.092107 |
| CD97 | 209 | 1.0 | 1.0 | 1.0 | 0.8 | 1.0 | 0.082986 |
| TAAR9 | 160 | 0.9 | 1.1 | 1.0 | 0.9 | 1.0 | 0.070721 |
| SSTR2 | 16 | 0.8 | 1.5 | 0.6 | 0.9 | 1.0 | 0.324644 |
| HTR1B | 246 | 1.0 | 1.0 | 0.8 | 1.1 | 1.0 | 0.117216 |
| GPR64 | 5 | 1.1 | 1.0 | 1.0 | 0.8 | 1.0 | 0.142582 |
| CHRM5 | 250 | 1.1 | 1.0 | 0.9 | 0.9 | 1.0 | 0.088827 |
| F2RL2 | 306 | 0.9 | 1.0 | 1.0 | 0.9 | 1.0 | 0.048437 |
| PTGFR | 96 | 0.7 | 0.8 | 1.5 | 0.8 | 1.0 | 0.331442 |
| HCA3 | 133 | 0.3 | 1.1 | 0.9 | 1.5 | 1.0 | 0.445169 |
| GPR156 | 252 | 0.4 | 1.2 | 0.6 | 1.6 | 0.9 | 0.485539 |
| MAS1L | 206 | 1.2 | 0.6 | 0.8 | 1.2 | 0.9 | 0.259695 |
| LHCGR | 77 | 1.4 | 0.8 | 0.7 | 1.0 | 0.9 | 0.285837 |
| GPR126 | 19 | 1.0 | 0.9 | 1.2 | 0.8 | 0.9 | 0.14734 |
| ELTD1 | 290 | 1.2 | 0.7 | 0.9 | 0.9 | 0.9 | 0.191207 |
| APJ | 265 | 1.1 | 0.9 | 0.8 | 0.9 | 0.9 | 0.110379 |
| S1PR5 | 136 | 0.8 | 1.1 | 0.9 | 1.0 | 0.9 | 0.127454 |
| NPFF2 | 70 | 1.2 | 0.7 | 1.2 | 0.7 | 0.9 | 0.273443 |
| MTNR1A | 167 | 0.7 | 1.4 | 0.8 | 0.8 | 0.9 | 0.277311 |
| GPR143 | 211 | 0.9 | 0.9 | 1.0 | 1.0 | 0.9 | 0.047067 |
| FPR2 | 99 | 0.9 | 0.9 | 0.7 | 1.3 | 0.9 | 0.252093 |
| RXFP1 | 104 | 1.1 | 0.9 | 0.8 | 0.9 | 0.9 | 0.094169 |
| BDKBR2 | 177 | 1.0 | 1.2 | 0.8 | 0.8 | 0.9 | 0.184391 |
| PTGER1 | 159 | 0.7 | 1.0 | 0.9 | 1.0 | 0.9 | 0.113973 |
| HCTR2 | 53 | 1.6 | 1.1 | 0.3 | 0.5 | 0.9 | 0.559201 |
| GPR68 | 236 | 0.9 | 1.0 | 1.1 | 0.7 | 0.9 | 0.152451 |
| NPY5R | 199 | 0.9 | 0.7 | 1.0 | 0.9 | 0.9 | 0.115451 |
| OPRM1 | 127 | 0.9 | 0.8 | 1.3 | 0.6 | 0.9 | 0.26195 |
| P2RY13 | 311 | 0.9 | 0.7 | 0.7 | 1.3 | 0.9 | 0.248726 |
| GPR125 | 203 | 0.8 | 1.1 | 0.8 | 0.9 | 0.9 | 0.136205 |
| OPRL1 | 15 | 0.7 | 0.9 | 0.8 | 1.2 | 0.9 | 0.237512 |
| GPR37L1 | 204 | 0.9 | 1.0 | 0.9 | 0.9 | 0.9 | 0.044954 |
| GPR21 | 164 | 1.2 | 1.0 | 0.9 | 0.5 | 0.9 | 0.283422 |
| TSHR | 232 | 1.1 | 0.7 | 1.2 | 0.6 | 0.9 | 0.244707 |
| OPN5 | 295 | 0.9 | 0.9 | 0.9 | 0.8 | 0.9 | 0.050365 |
| OPRK1 | 207 | 1.2 | 0.8 | 0.8 | 0.8 | 0.9 | 0.184722 |
| GHSR | 251 | 0.8 | 0.8 | 1.1 | 0.9 | 0.9 | 0.131788 |
| HRH4 | 166 | 0.8 | 0.7 | 0.8 | 1.2 | 0.9 | 0.182247 |
| CNR2 | 233 | 0.3 | 0.7 | 1.6 | 0.9 | 0.9 | 0.513181 |
| CCR4 | 201 | 0.9 | 1.0 | 0.9 | 0.8 | 0.9 | 0.093319 |
| GCGR | 123 | 0.7 | 1.0 | 0.7 | 1.2 | 0.9 | 0.257352 |

TABLE 1-continued

| DNA | #1 | I | II | III | IV | AVG | CV |
|---|---|---|---|---|---|---|---|
| AGTR1 | 41 | 0.6 | 0.7 | 0.7 | 1.6 | 0.9 | 0.478135 |
| RXFP2 | 288 | 0.9 | 0.7 | 1.1 | 0.8 | 0.9 | 0.163413 |
| GPR12 | 299 | 0.8 | 0.9 | 0.8 | 1.0 | 0.9 | 0.088899 |
| GPR55 | 245 | 0.9 | 0.9 | 0.8 | 0.9 | 0.9 | 0.034241 |
| NPY1R | 183 | 0.8 | 0.9 | 1.0 | 0.8 | 0.9 | 0.108672 |
| GPR174 | 219 | 0.8 | 1.1 | 0.9 | 0.7 | 0.9 | 0.162247 |
| GPRC5C | 37 | 0.4 | 0.6 | 0.8 | 1.7 | 0.9 | 0.573607 |
| GPR52 | 316 | 1.0 | 0.7 | 0.8 | 1.0 | 0.9 | 0.167925 |
| LPAR5 | 118 | 0.8 | 1.3 | 0.6 | 0.7 | 0.9 | 0.301845 |
| LPAR6 | 190 | 0.6 | 1.1 | 0.9 | 0.9 | 0.9 | 0.216683 |
| MRGPRD | 255 | 0.8 | 1.0 | 0.9 | 0.8 | 0.9 | 0.08955 |
| GPBA | 179 | 0.9 | 1.0 | 0.7 | 0.8 | 0.9 | 0.10381 |
| GIPR | 131 | 0.7 | 0.8 | 1.0 | 0.9 | 0.8 | 0.154769 |
| NMUR1 | 158 | 0.3 | 0.8 | 0.5 | 1.8 | 0.8 | 0.679201 |
| CXCR1 | 138 | 0.8 | 0.8 | 0.8 | 1.0 | 0.8 | 0.079673 |
| GPR162 | 148 | 1.6 | 0.7 | 0.5 | 0.6 | 0.8 | 0.529064 |
| HTR1A | 149 | 0.5 | 0.9 | 1.3 | 0.7 | 0.8 | 0.327798 |
| CX3CR1 | 130 | 0.8 | 0.8 | 0.9 | 0.8 | 0.8 | 0.064166 |
| GPR27 | 44 | 0.8 | 0.8 | 0.8 | 0.9 | 0.8 | 0.037781 |
| GPR146 | 51 | 0.6 | 1.1 | 0.7 | 0.9 | 0.8 | 0.219755 |
| SSTR5 | 32 | 0.8 | 0.7 | 1.1 | 0.7 | 0.8 | 0.174645 |
| GAL2 | 58 | 0.5 | 0.9 | 0.7 | 1.1 | 0.8 | 0.294932 |
| ADRA2C | 17 | 1.0 | 1.1 | 0.7 | 0.5 | 0.8 | 0.306529 |
| ADCYAP1R1 | 1 | 0.5 | 0.7 | 0.7 | 1.4 | 0.8 | 0.402641 |
| RXFP4 | 8 | 0.8 | 0.8 | 0.7 | 0.9 | 0.8 | 0.09744 |
| GPR6 | 261 | 1.0 | 0.6 | 0.7 | 1.0 | 0.8 | 0.205366 |
| MC4R | 214 | 0.8 | 0.6 | 1.1 | 0.7 | 0.8 | 0.238346 |
| DRD5 | 91 | 0.7 | 0.9 | 0.7 | 0.9 | 0.8 | 0.147659 |
| PRRP | 55 | 0.6 | 0.5 | 1.0 | 1.1 | 0.8 | 0.281916 |
| CRHR1 | 114 | 1.0 | 0.9 | 0.7 | 0.6 | 0.8 | 0.198577 |
| GAL3 | 115 | 0.7 | 0.9 | 0.7 | 0.8 | 0.8 | 0.105755 |
| EDNRB | 42 | 0.5 | 1.0 | 0.7 | 0.9 | 0.8 | 0.269574 |
| CCR10 | 193 | 1.0 | 1.2 | 0.5 | 0.5 | 0.8 | 0.388268 |
| OXGR1 | 303 | 1.1 | 0.9 | 0.5 | 0.7 | 0.8 | 0.295728 |
| HTR2C INI | 157 | 0.8 | 0.6 | 0.9 | 0.9 | 0.8 | 0.163541 |
| C5A | 185 | 0.6 | 0.8 | 0.8 | 0.8 | 0.8 | 0.104819 |
| ADRB2 | 25 | 0.8 | 0.8 | 0.7 | 0.8 | 0.8 | |
| GAL1 | 226 | 0.7 | 0.8 | 0.8 | 0.8 | 0.8 | 0.085654 |
| HCA1 | 125 | 0.8 | 0.8 | 0.7 | 0.7 | 0.8 | 0.088934 |
| OPN3 | 7 | 0.6 | 1.1 | 0.6 | 0.8 | 0.8 | 0.237756 |
| HRH3 | 61 | 0.5 | 0.4 | 1.6 | 0.5 | 0.8 | 0.65861 |
| HTR2C VNV | 86 | 0.7 | 1.1 | 0.8 | 0.4 | 0.8 | 0.339023 |
| GPER | 139 | 0.8 | 0.7 | 0.6 | 0.9 | 0.7 | 0.131826 |
| CXCR7 | 282 | 0.6 | 0.6 | 1.0 | 0.6 | 0.7 | 0.24167 |
| FFA1 | 314 | 0.6 | 0.8 | 0.7 | 0.8 | 0.7 | 0.096597 |
| HRH2 | 141 | 0.8 | 0.7 | 0.5 | 1.0 | 0.7 | 0.238584 |
| HCTR1 | 45 | 1.1 | 0.4 | 0.5 | 0.9 | 0.7 | 0.361983 |
| MAS1 | 247 | 0.6 | 0.7 | 0.8 | 0.7 | 0.7 | 0.096346 |
| MTNR1B | 175 | 0.5 | 0.8 | 0.5 | 0.9 | 0.7 | 0.248458 |
| P2RY12 | 143 | 0.5 | 0.7 | 0.8 | 0.8 | 0.7 | 0.150152 |
| GPR85 | 173 | 0.8 | 0.6 | 0.8 | 0.7 | 0.7 | 0.112671 |
| GPR45 | 60 | 0.7 | 0.7 | 0.9 | 0.6 | 0.7 | 0.164796 |
| PK2 | 47 | 0.6 | 0.5 | 0.6 | 1.1 | 0.7 | 0.374488 |
| GPR142 | 92 | 0.8 | 0.6 | 0.7 | 0.7 | 0.7 | 0.132169 |
| TACR3 | 320 | 0.8 | 0.8 | 0.6 | 0.6 | 0.7 | 0.120293 |
| GRM1 | 213 | 1.0 | 0.4 | 0.6 | 0.7 | 0.7 | 0.319909 |
| TBXA2R | 64 | 0.6 | 1.0 | 0.8 | 0.3 | 0.7 | 0.350972 |
| S1PR2 | 120 | 0.9 | 0.5 | 0.6 | 0.7 | 0.7 | 0.211167 |
| HTR2CVGV | 102 | 1.4 | 0.5 | 0.5 | 0.2 | 0.7 | 0.663904 |
| PTH2R | 184 | 0.6 | 0.5 | 0.6 | 0.9 | 0.7 | 0.183049 |
| HTR5 | 286 | 0.8 | 0.5 | 0.5 | 0.9 | 0.7 | 0.281163 |
| GPR15 | 108 | 0.6 | 0.8 | 0.5 | 0.6 | 0.6 | 0.181382 |
| S1PR3 | 128 | 0.4 | 0.8 | 0.5 | 0.9 | 0.6 | 0.318966 |
| NPFF1 | 62 | 0.5 | 0.6 | 0.9 | 0.5 | 0.6 | 0.293851 |
| GPR149 | 100 | 0.5 | 0.9 | 0.4 | 0.6 | 0.6 | 0.263301 |
| HTR6 | 110 | 0.5 | 0.7 | 0.6 | 0.6 | 0.6 | 0.130486 |
| CXCR3 | 162 | 0.5 | 0.5 | 0.6 | 0.9 | 0.6 | 0.301079 |
| GPR114 | 147 | 0.5 | 0.5 | 0.7 | 0.7 | 0.6 | 0.182666 |
| VIPR1 | 240 | 0.8 | 0.6 | 0.6 | 0.3 | 0.6 | 0.303804 |
| GPR25 | 36 | 0.6 | 0.8 | 0.3 | 0.7 | 0.6 | 0.292075 |
| GPR75 | 13 | 0.6 | 0.4 | 0.8 | 0.5 | 0.6 | 0.286333 |
| GPR20 | 20 | 0.4 | 0.6 | 0.6 | 0.5 | 0.5 | 0.15321 |
| DRD3 | 34 | 0.4 | 0.3 | 0.8 | 0.5 | 0.5 | 0.374166 |
| RXFP3 | 112 | 0.4 | 0.4 | 0.4 | 0.7 | 0.5 | 0.245883 |
| MC2R | 14 | 0.4 | 0.5 | 0.6 | 0.4 | 0.5 | 0.183613 |
| ADORA2A | 81 | 0.4 | 0.3 | 0.7 | 0.4 | 0.5 | 0.273364 |
| TAAR2 | 216 | 0.5 | 0.5 | 0.4 | 0.4 | 0.4 | 0.100295 |
| BB3 | 281 | 0.4 | 0.6 | 0.4 | 0.3 | 0.4 | 0.228779 |

TABLE 1-continued

| DNA | #1 | I | II | III | IV | AVG | CV |
|---|---|---|---|---|---|---|---|
| GRM6 | 109 | 0.4 | 0.3 | 0.4 | 0.3 | 0.4 | 0.166321 |
| GPR157 | 132 | 0.2 | 0.2 | 0.2 | 0.2 | 0.2 | 0.089045 |

Figure 2:
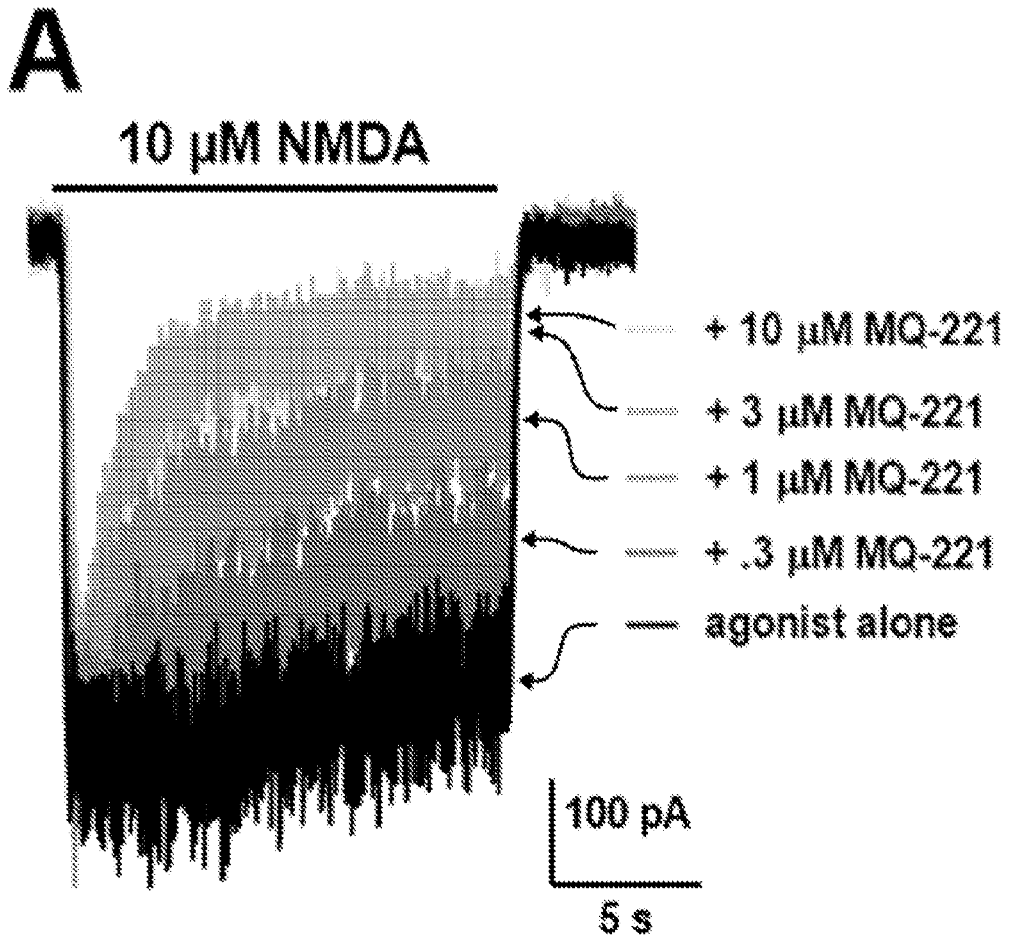
FIG. 2. MQ-221 has high potency for both NMDAR and $GABA_AR$ effects. A. Example responses of 10 μM NMDA inhibited by the indicated escalating concentrations of MQ-221. B. Inhibition-response curve of MQ-221 on 10 μM NMDA current. The solid line shows a least-squares fit to the Hill equation yielding an $IC_{50}$ value of 0.6 μM and Hill slope of −1.0. C. Example responses of 0.5 μM GABA potentiated by the same indicated concentrations of MQ-221 D. Concentration-response relationship of MQ-221 on 0.5 μM GABA current. The solid line shows a fit to the Hill equation yielding an $EC_{50}$ of 2.6 μM and a Hill slope of 1.6.
Figure 2:
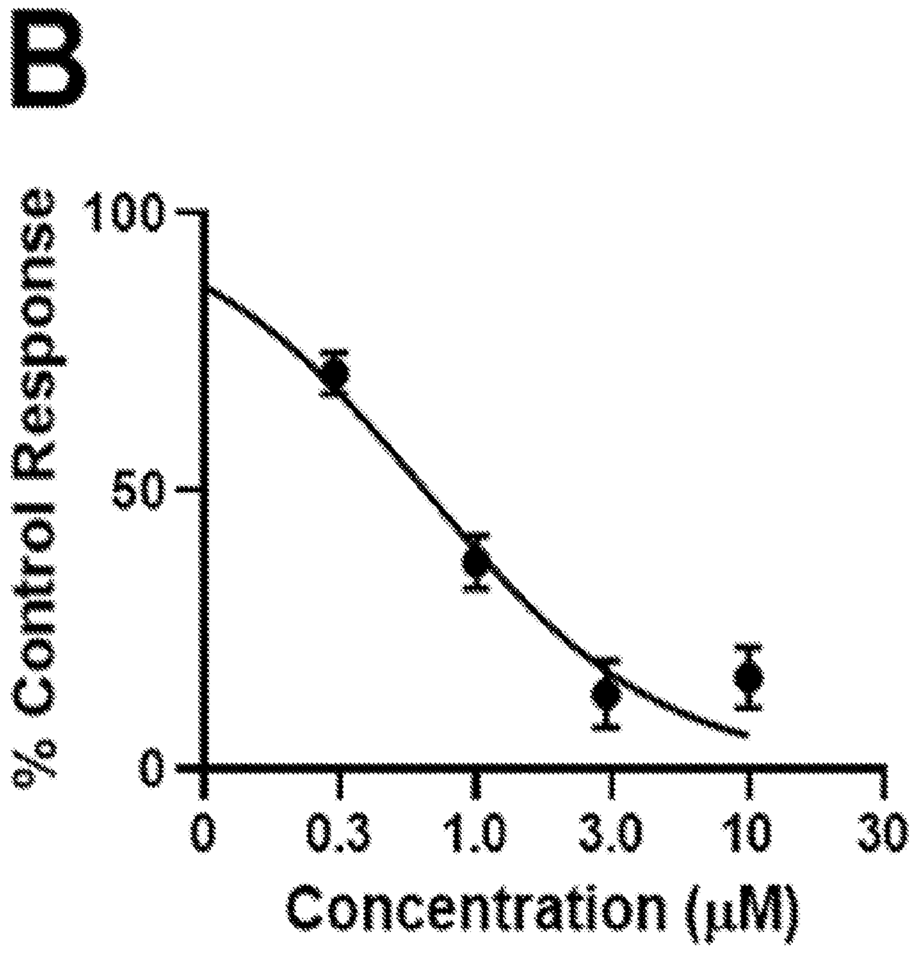
Figure 2:
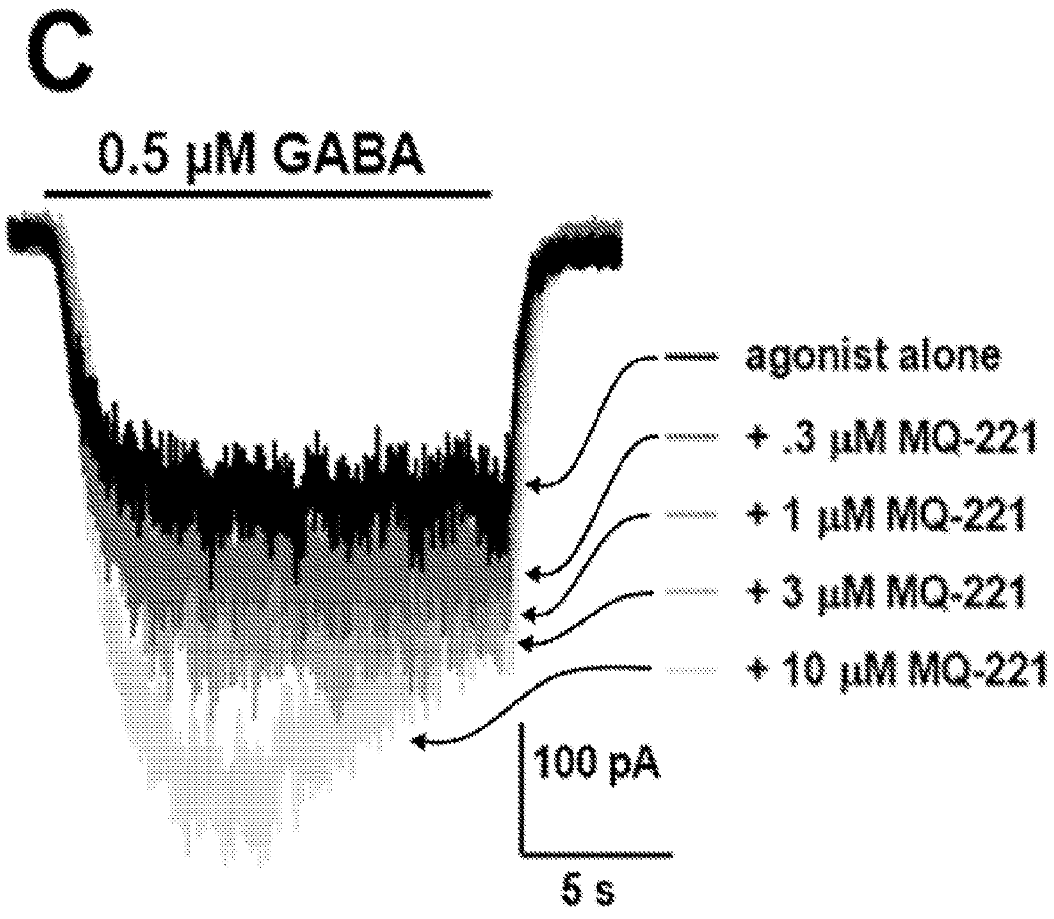
Figure 2:
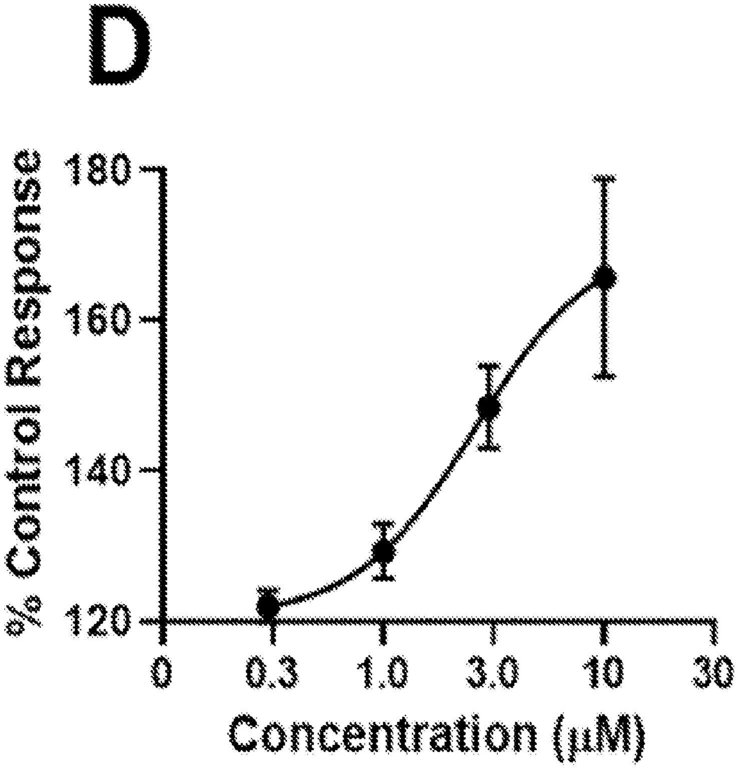

To gain a more detailed characterization of NMDAR inhibition and $GABA_AR$ potentiation, we examined the impact of systematically varied MQ-221 concentration on neuronal responses to 10 μM NMDA and 0.5 μM GABA (FIG. 2). A low concentration of GABA was employed to emphasize potentiation while minimizing GABA-concentration dependent inhibition (Eisenman et al., 2003). Fits of potentiation to the Hill equation yielded an $IC_{50}$ for NMDA currents of 0.7 μM and an EC50 of 2.6 μM for $GABA_AR$ (FIG. 2, panels B and D). The results confirm that modulation of the two receptor classes occurs in an overlapping concentration range, which would be advantageous for therapeutic applications.

Effects on Synaptic Function.

Figure 3:
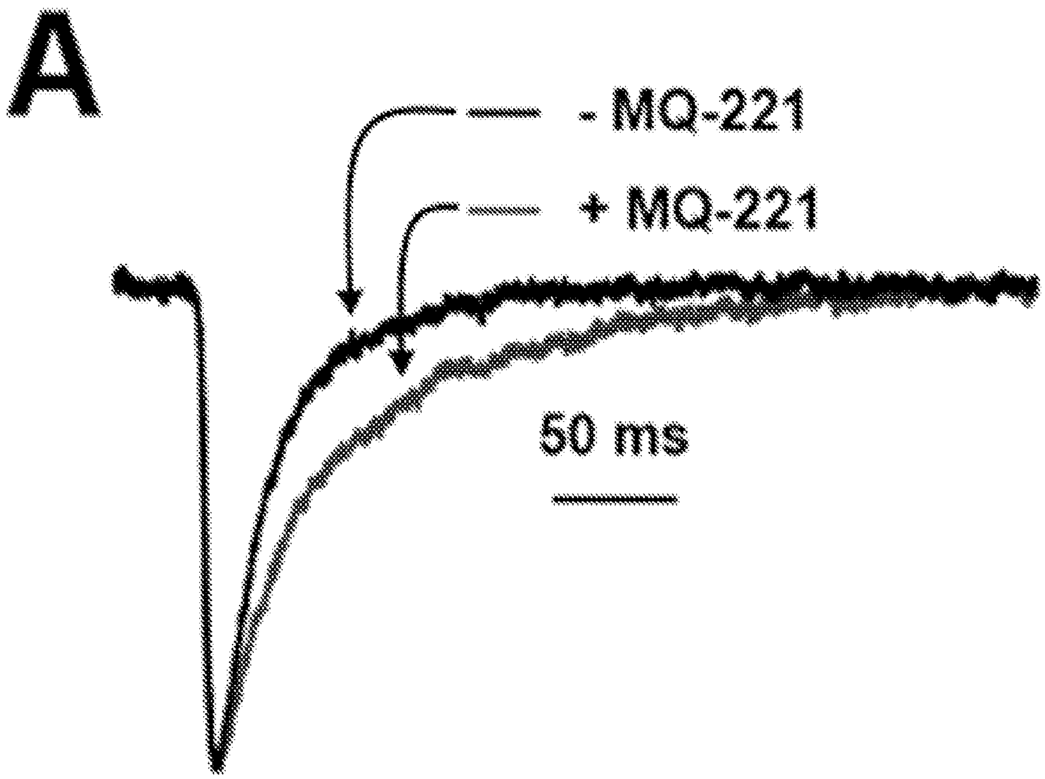
FIG. 3. Effects of MQ-221 on EPSCs and IPSCs. A. Sample normalized and averaged $GABA_A$ IPSCs with and without application of 1 μM MQ-221. B. Left: Decay time constants of average $GABA_A$ IPSCs in the absence and presence of MQ-221 ($t=3.7$, $p=0.014$, paired t test). Right: Peak amplitude of average $GABA_A$ IPSCs±MQ-221 ($t=1.2$, $p=0.275$, paired t test). C. Sample average NMDA EPSCs±1 μM MQ-221. D. Left: Decays of averaged NMDA EPSCs with and without 1 μM MQ-221 ($t=0.7$, $p=0.525$, paired t test). Right: Peak amplitude of average NMDA EPSCs±1 μM MQ-221 ($t=3.8$, $p=0.013$, paired t test). E. Example averaged AMPA EPSCs±1 μM MQ-221. F. Decay time constants of average AMPA EPSCs±MQ-221 ($t=1.1$, $p=0.339$, paired t test). Peak amplitude of averaged AMPA EPSCs MQ-221 ($t=0.394$, $p=0.710$, paired t test).
Figure 3:
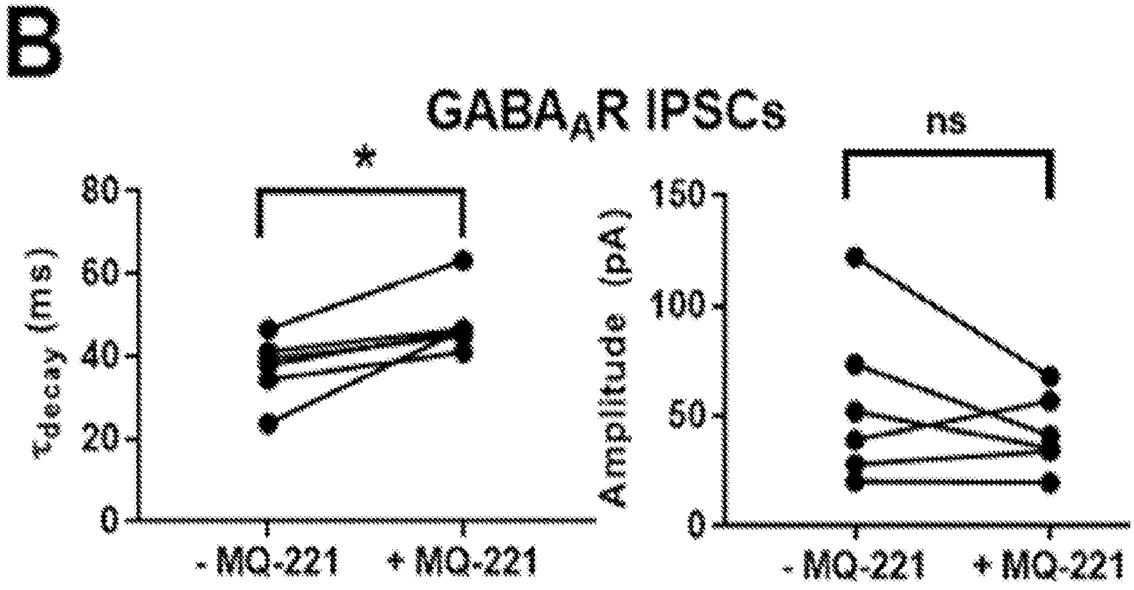
Figure 3:
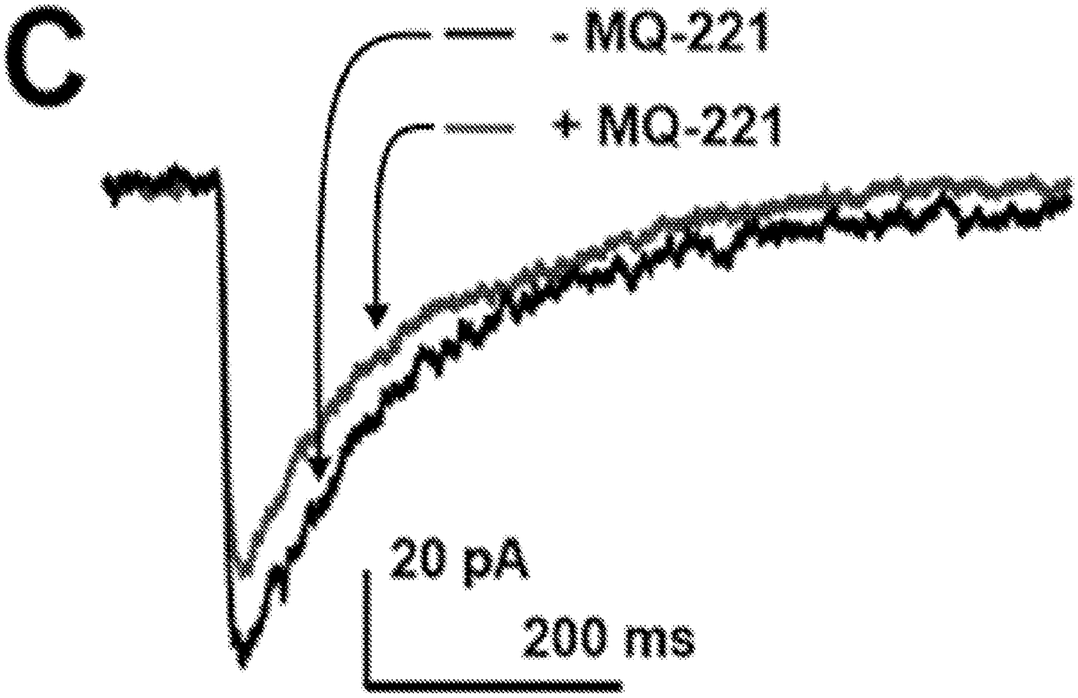
Figure 3:
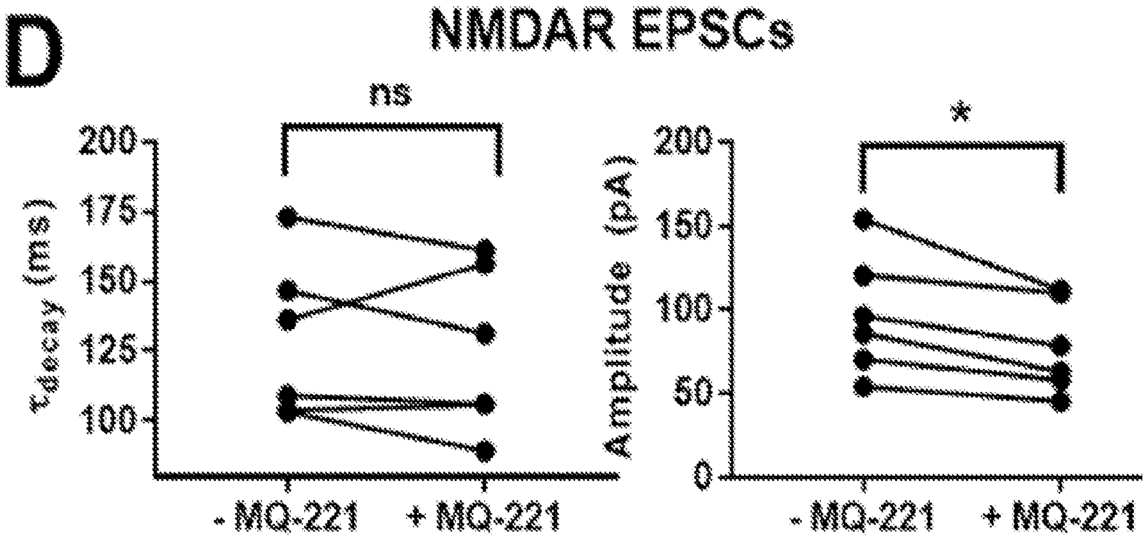
Figure 3:
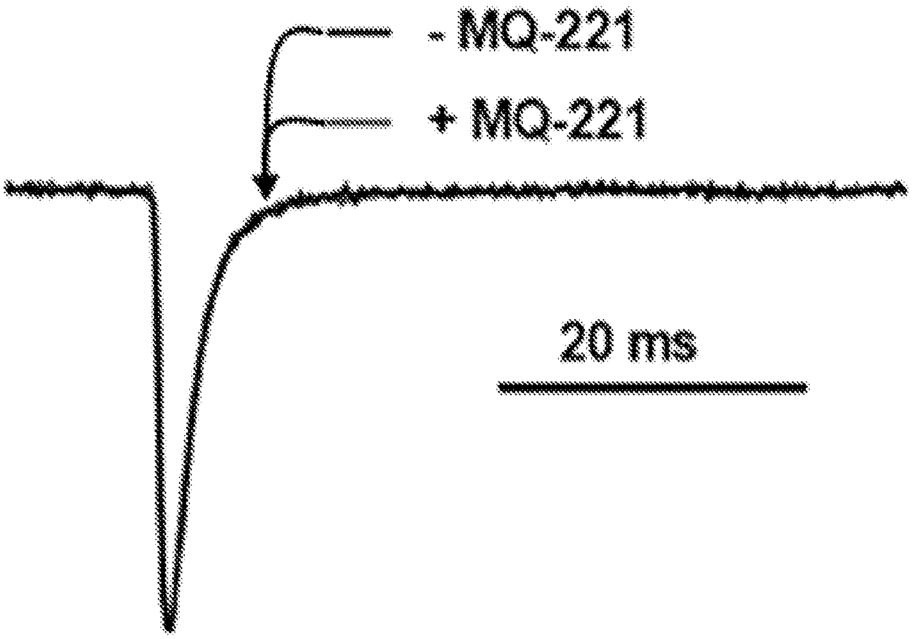
Figure 3:
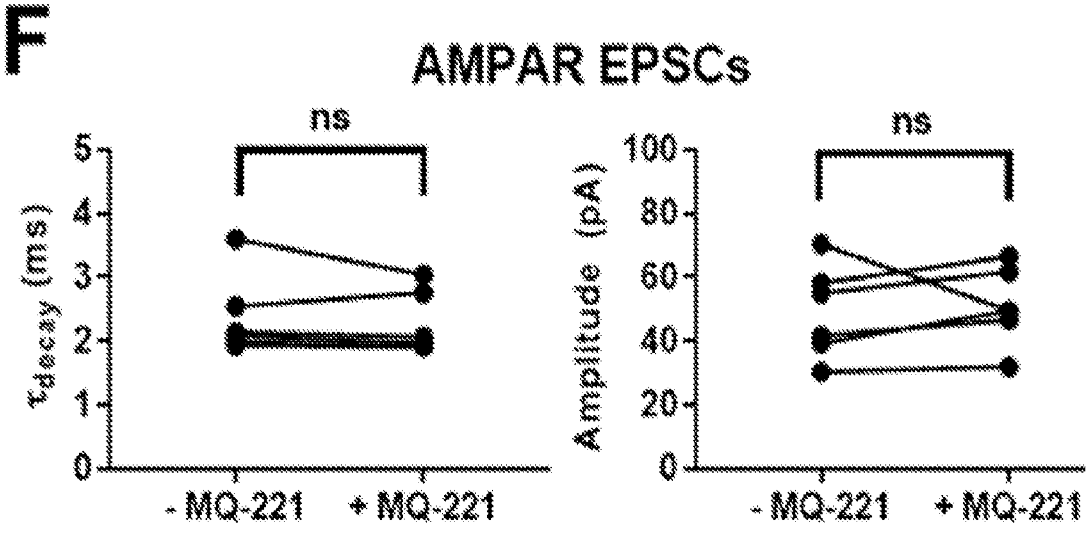

We addressed the impact of MQ-221 on physiological functioning by examining sEPSCs and sIPSCs in cultures of hippocampal neurons (FIG. 3). MQ-221 (1 μM) prolonged $GABA_AR$ IPSCs, similar to the effect of anesthetic neurosteroids (Harrison et al., 1987) (FIG. 3, panels A and B). By contrast, MQ-221 primarily reduced the peak amplitude of NMDAR EPSCs and had no effect on AMPAR EPSCs, confirming specificity of the neurosteroid effect on NMDAR function (FIG. 3, panels C-F). We found that at concentrations up to 2.5 μM MQ-221 had variable effects on frequency of EPSCs and IPSCs (2±7% increase, n=6, p=0.8 and 142±47%, n=7, p=0.15 respectively). Further, at 2.5 μM MQ-221 continued to prolong IPSC decays (42±11% increase decay time constant, p=0.007).

Comparison with Other Neuroactive Steroids.

Figure 4:
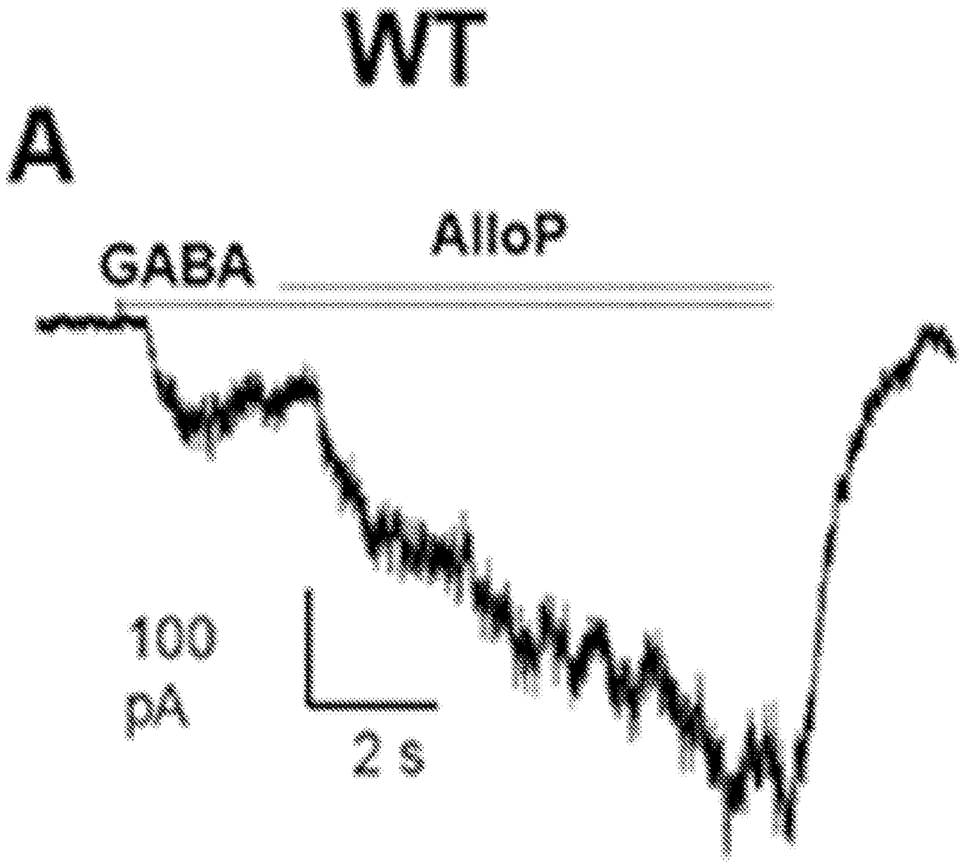
FIG. 4. GABA potentiation is through a mechanism distinct from anesthetic neurosteroids. A, B, Examples of the effect of allopregnanolone (AlloP; 50 nM) on response to 10 μM GABA in wild-type $GABA_ARs$ (A) and α1Q241L mutated $GABA_ARs$, as indicated. C. Summary of allopregnanolone effects with 10 s application time. D, E. In contrast to potentiation by allopregnanolone, potentiation by 10 μM MQ-221 remained with the Q241L mutation. F. Summary of peak potentiation relative to current just prior to co-application by MQ-221 in the protocol shown in D, E.
Figure 4:
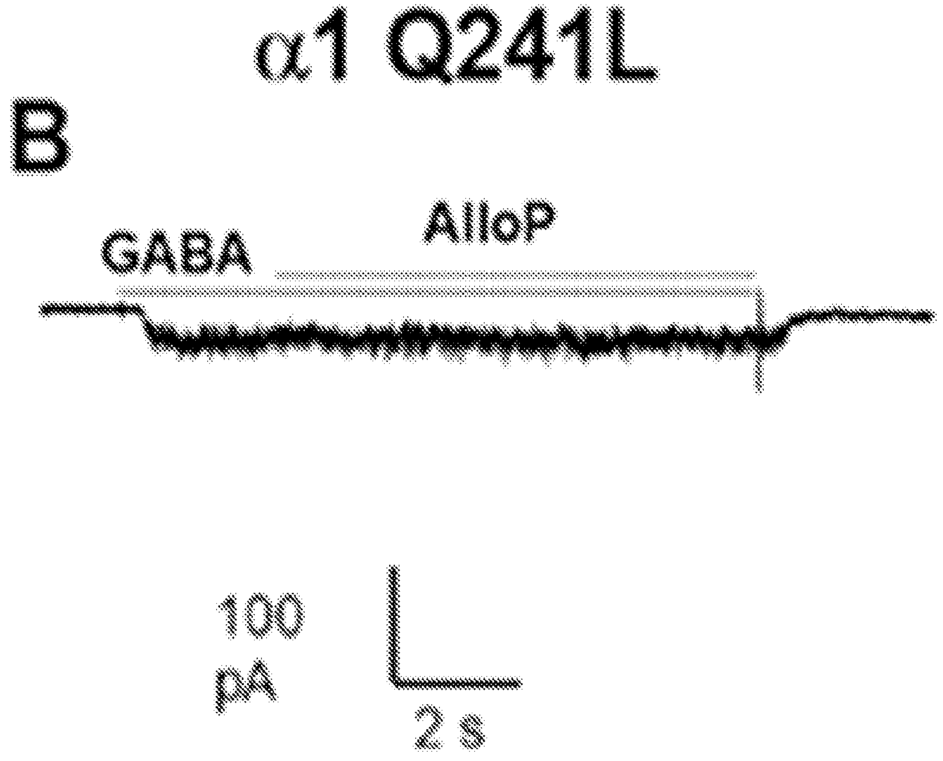
Figure 4:
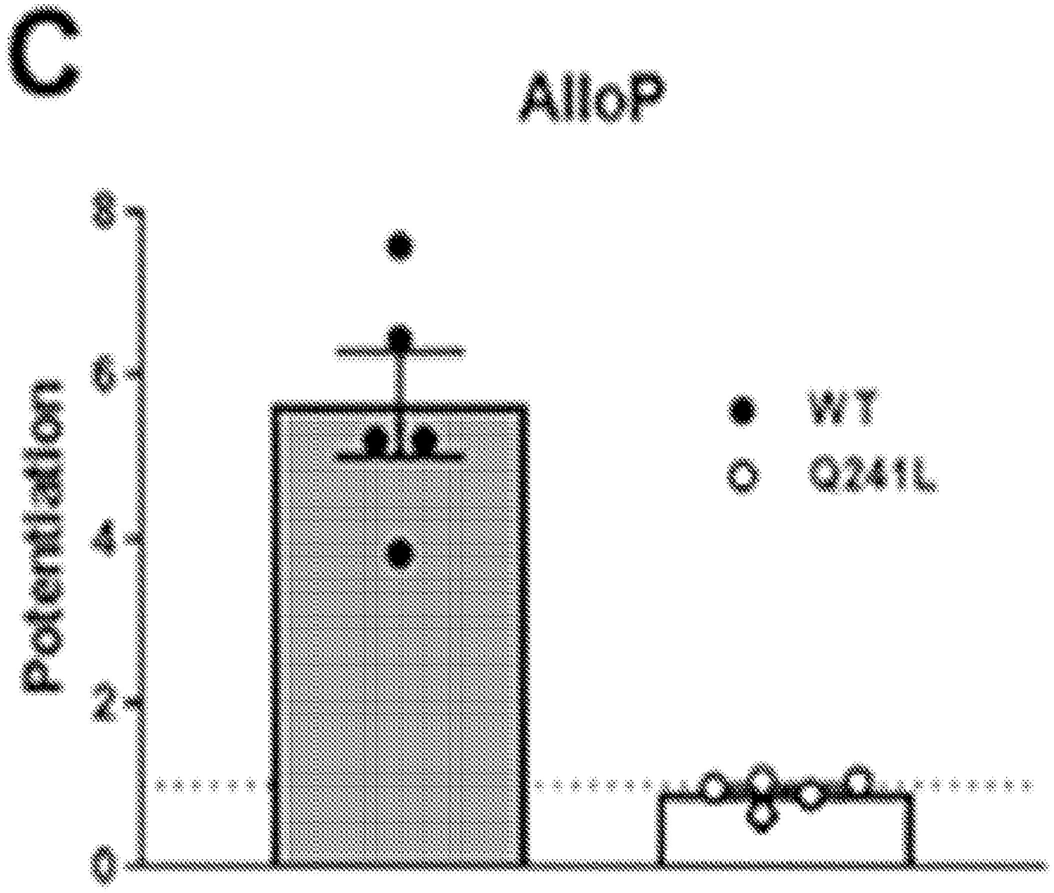
Figure 4:
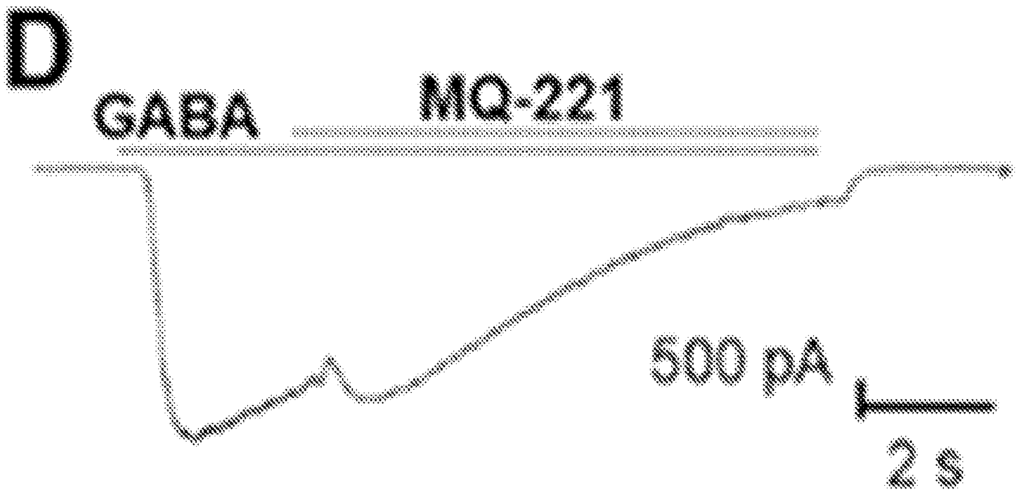
Figure 4:
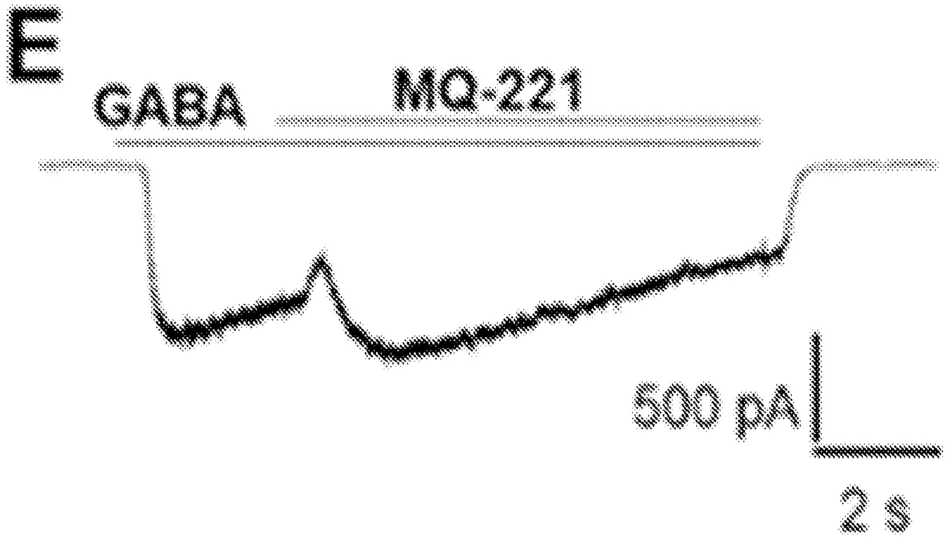
Figure 4:
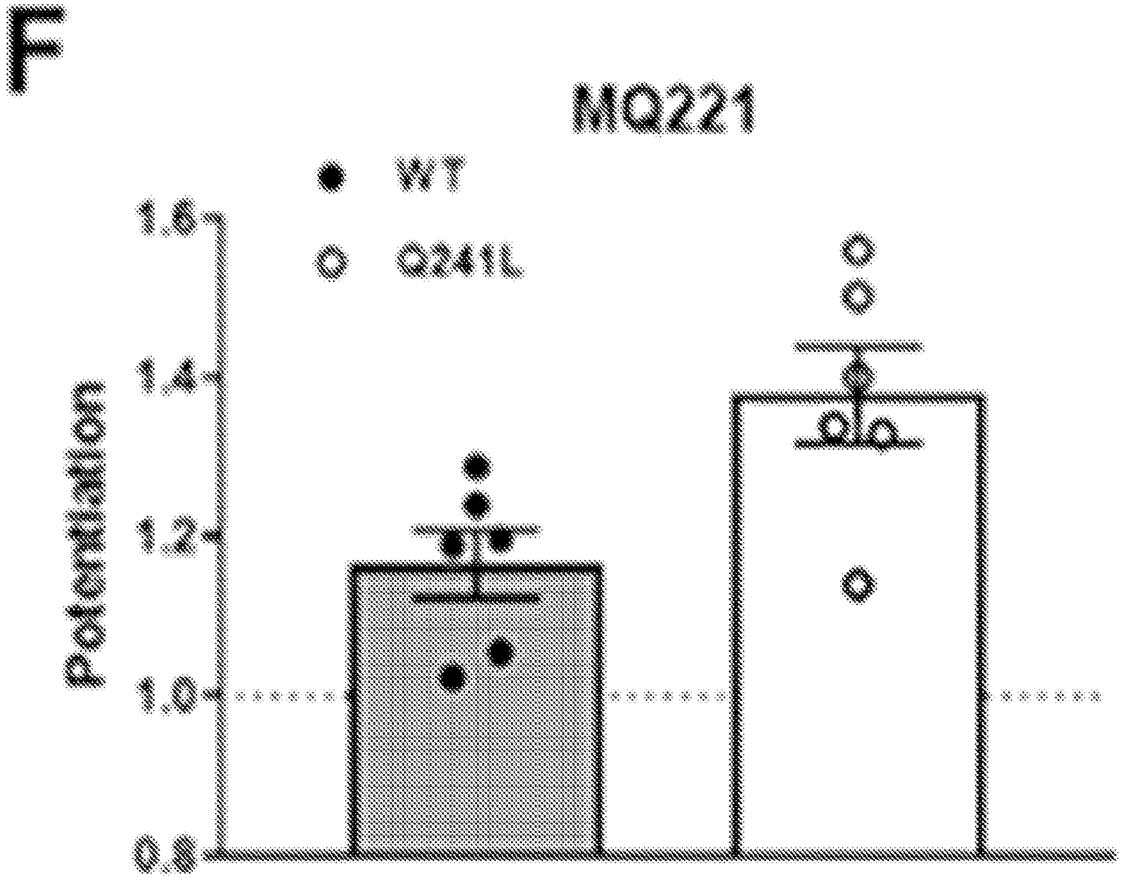

The potentiation of $GABA_AR$ current by a sulfated steroid is the most surprising effect of MQ-221, because MQ-221 does not have structural attributes that characterize neurosteroid potentiation (Covey et al., 2001). To test whether MQ-221 shares a mechanism with conventional $GABA_AR$-potentiating neurosteroids, we examined the effect of the al Q241L mutation, which eliminates potentiation by anesthetic neurosteroids (Hosie et al., 2006). Despite elimination of allopregnanolone (AlloP) potentiation of GABA current in N2a cells transfected with al (WT or Q241 mutant), β2, and γ2 subunits (FIG. 4, panels A-C), the Q241L mutation failed to eliminate MQ-221 potentiation of GABA current (FIG. 4, panels D-F). In fact, MQ-221 slightly enhanced potentiation in the α1Q241L-containing receptors when compared with GABA current immediately prior to co-application (FIG. 4, panel F). This effect may result from a higher GABA $EC_{50}$ imparted by the mutation (Hosie et al., 2006), but we cannot exclude the possibility that the Q241L mutation induces a genuine increase in sensitivity to MQ-221. Regardless, the result clearly distinguishes the actions of MQ-221 from those of the endogenous neurosteroid allopregnanolone.

Characteristics of NMDAR Inhibition.

Figure 5:
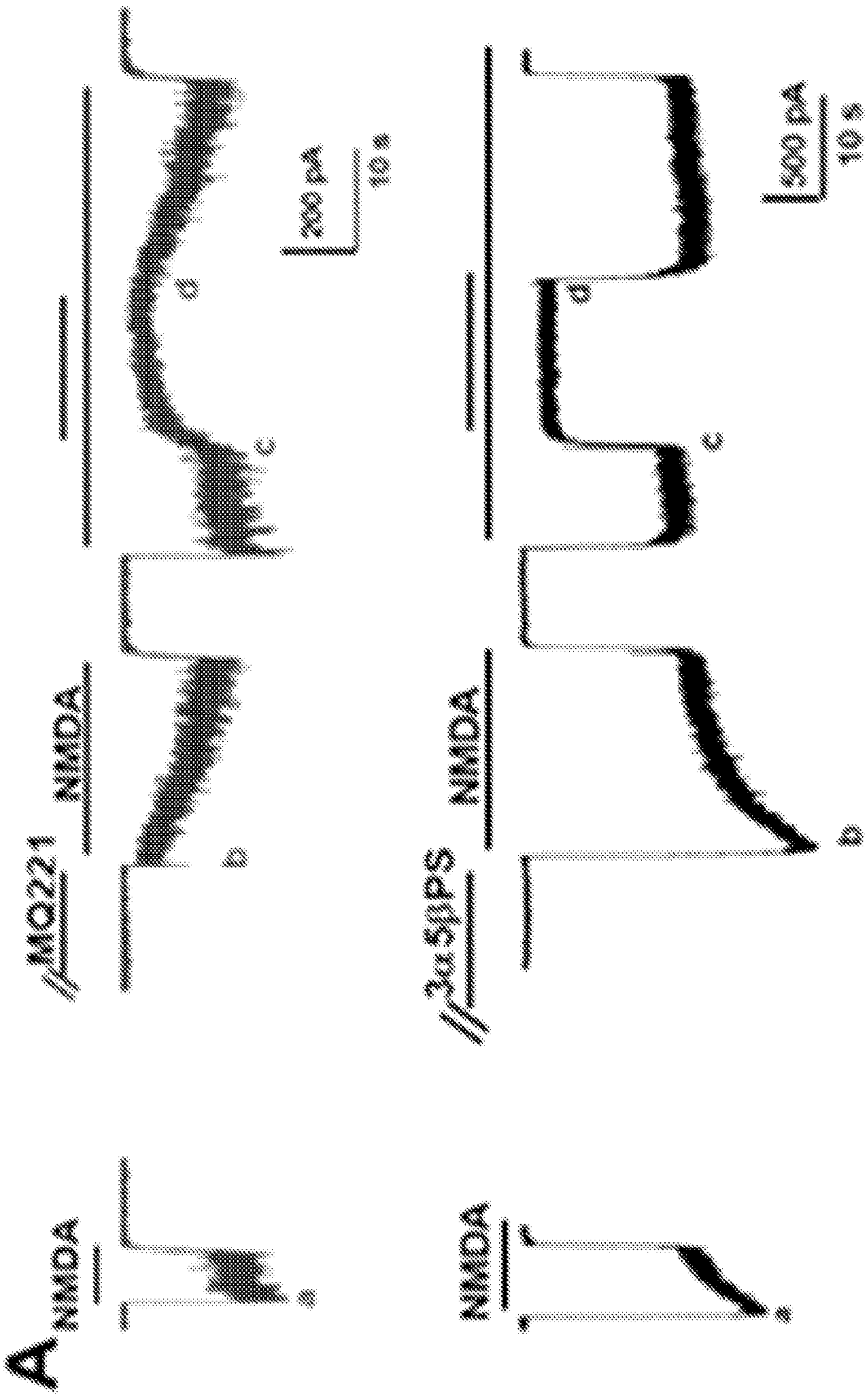
FIG. 5. MQ-221 exhibits weaker use dependence than pregnanolone sulfate (3α5βPS). A, Example responses of neurons to 10 μM NMDA with 2.5 μM MQ-221 and 300 μM 3α5βPS using pre-application and co-applications denoted by horizontal bars. Small letters indicate points of current measurement used in the summary (panel B). A two-way repeated measures ANOVA revealed a significant interaction between drug and channel state (dotted arrows; $F(1,14)=435.7$, $p<1\times10^{-4}$) Brackets indicate post-hoc testing with Sidak's multiple comparison test ($p<1\times10^{-4}$).
Figure 5:
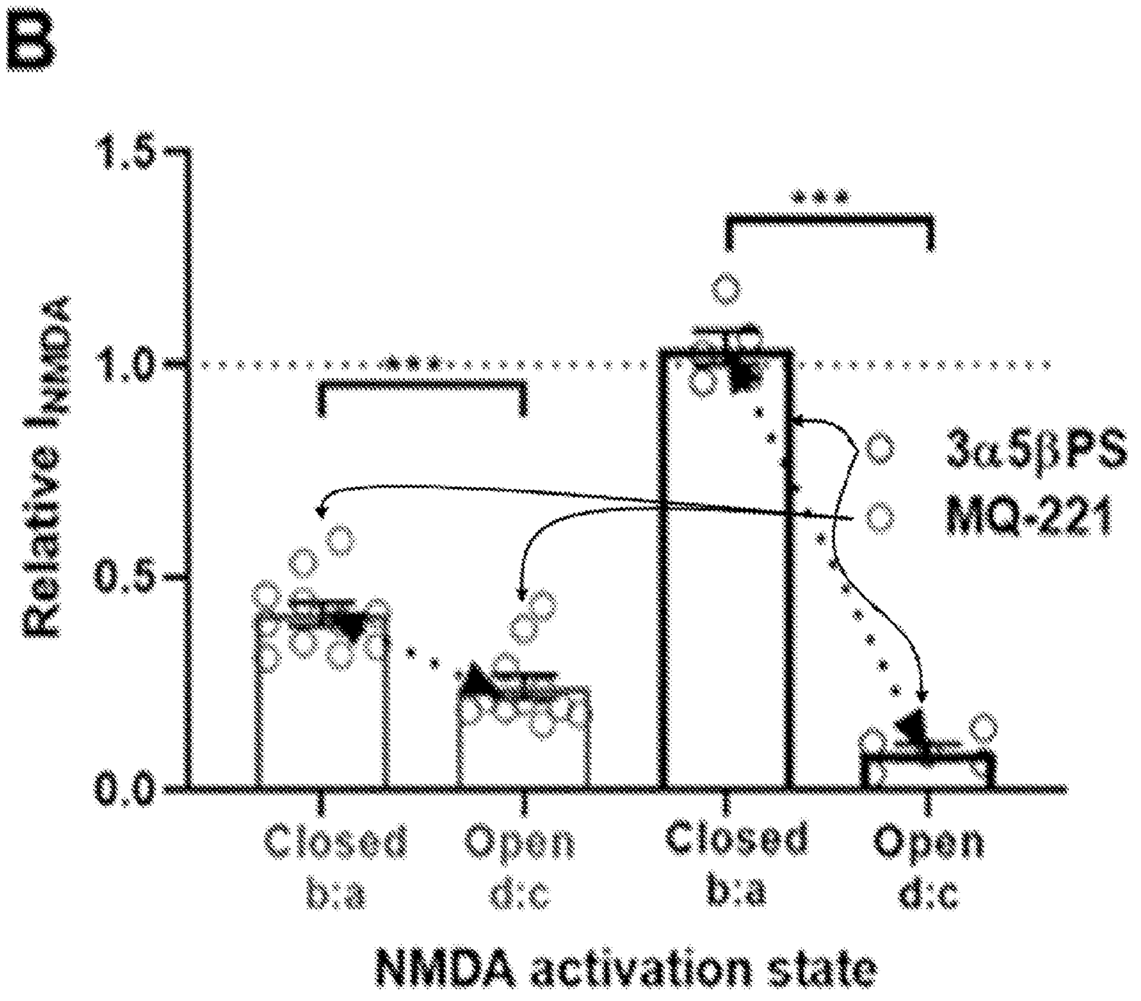

We next examined pharmacodynamic features of MQ-221 at NMDARs. Ketamine is an uncompetitive antagonist at NMDARs, requiring channel opening for entry and exit from the channel binding site (Johnson et al., 2014; MacDonald et al., 1987; Parsons et al., 1993). Although not likely a channel blocker, the sulfated neurosteroid pregnanolone sulfate, like ketamine, shows strong activation dependence (Petrovic et al., 2005). We queried the activation dependence of MQ-221 by comparing the impact of MQ-221 pre-application (in the absence of agonist), with the effect of MQ-221 co-applied during agonist presentation. Results demonstrated that MQ-221 interacted strongly with closed NMDAR channels (FIG. 5, panel A, top; FIG. 5, panel B). By contrast, as previously documented (Petrovic et al., 2005), pregnanolone sulfate had little effect on closed channels but instead strongly inhibited NMDAR function in the presence of agonist (FIG. 5, panel A, bottom; FIG. 5, panel B). The results demonstrate that sulfated neurosteroids can exhibit varied dependence on channel activation at NMDARs.

Figure 6:
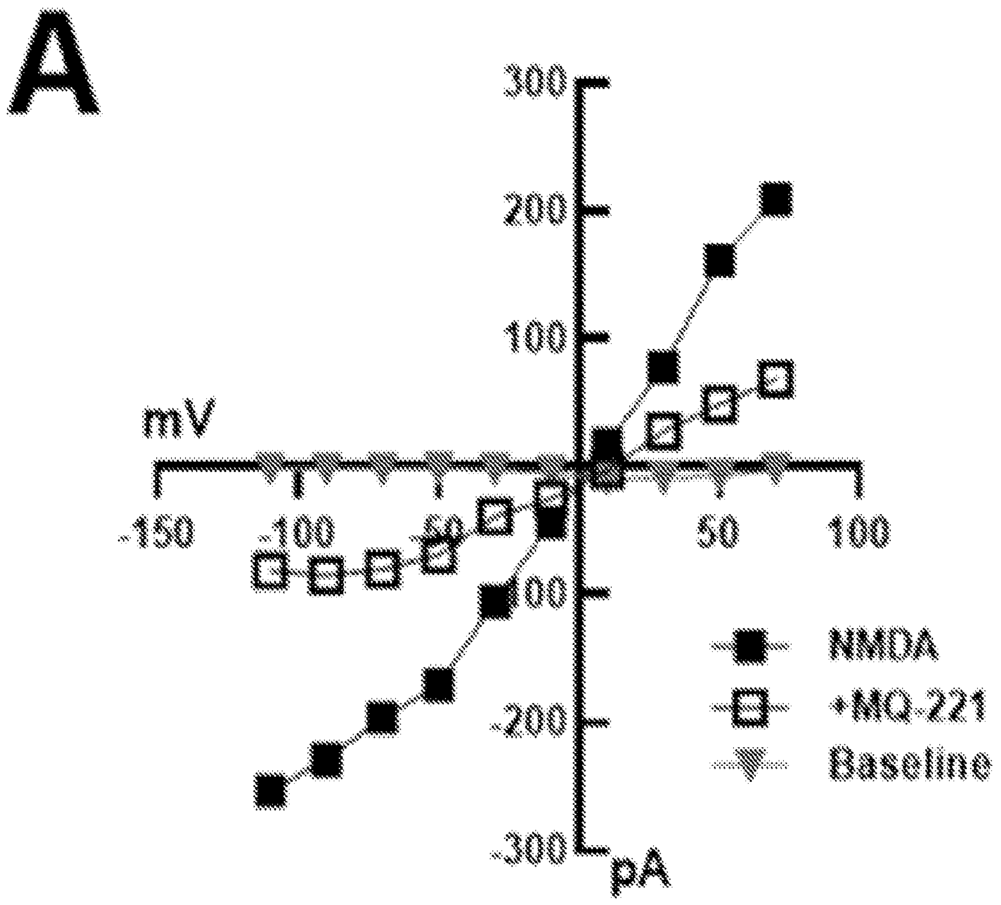
FIG. 6. MQ-221 inhibition is voltage independent. A, Example current-voltage relationships for steady-state responses at different voltages from a neuron to baseline, 10 μM NMDA, and NMDA in the presence of 2.5 μM MQ-221. B, Summary of relative MQ-221 inhibition in 6 cells at membrane potentials of −110 mV vs. +70 mV ($t=1.6$, $p=0.172$, paired t test). The red symbols represent the example from A.
Figure 6:
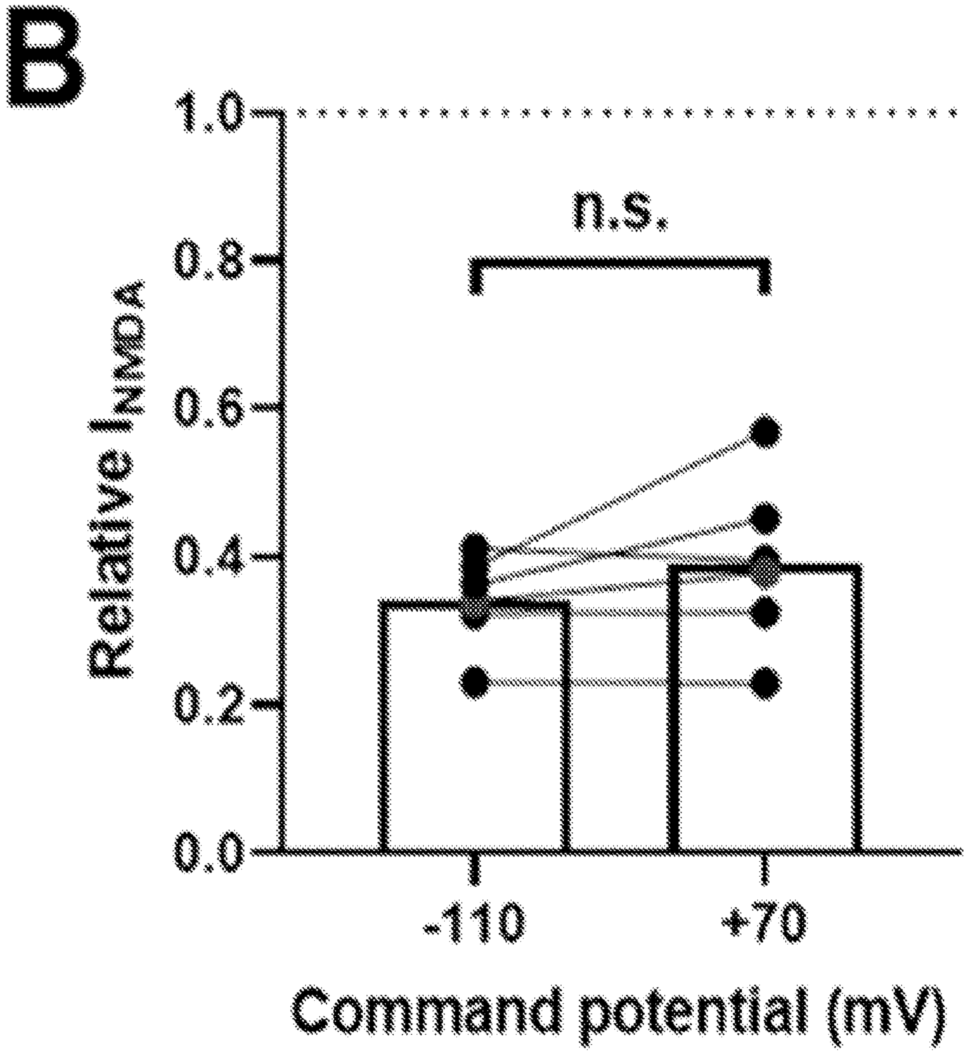

The slight activation dependence of MQ-221 inhibition raises the possibility that MQ-221 could access a site in the NMDAR channel. If channel access is sufficiently deep, whereby the negative charge on MQ-221 experiences the voltage difference across the membrane, we would expect voltage dependence of MQ-221 inhibition. However, current voltage-response analysis of NMDA responses in the absence of extracellular $Mg^{2+}$ showed no effect of MQ-221 inhibition on voltage between −110 mV and +70 mV (FIG. 6). Therefore, we conclude that MQ-221 is unlikely to be a channel blocker.

Figure 7:
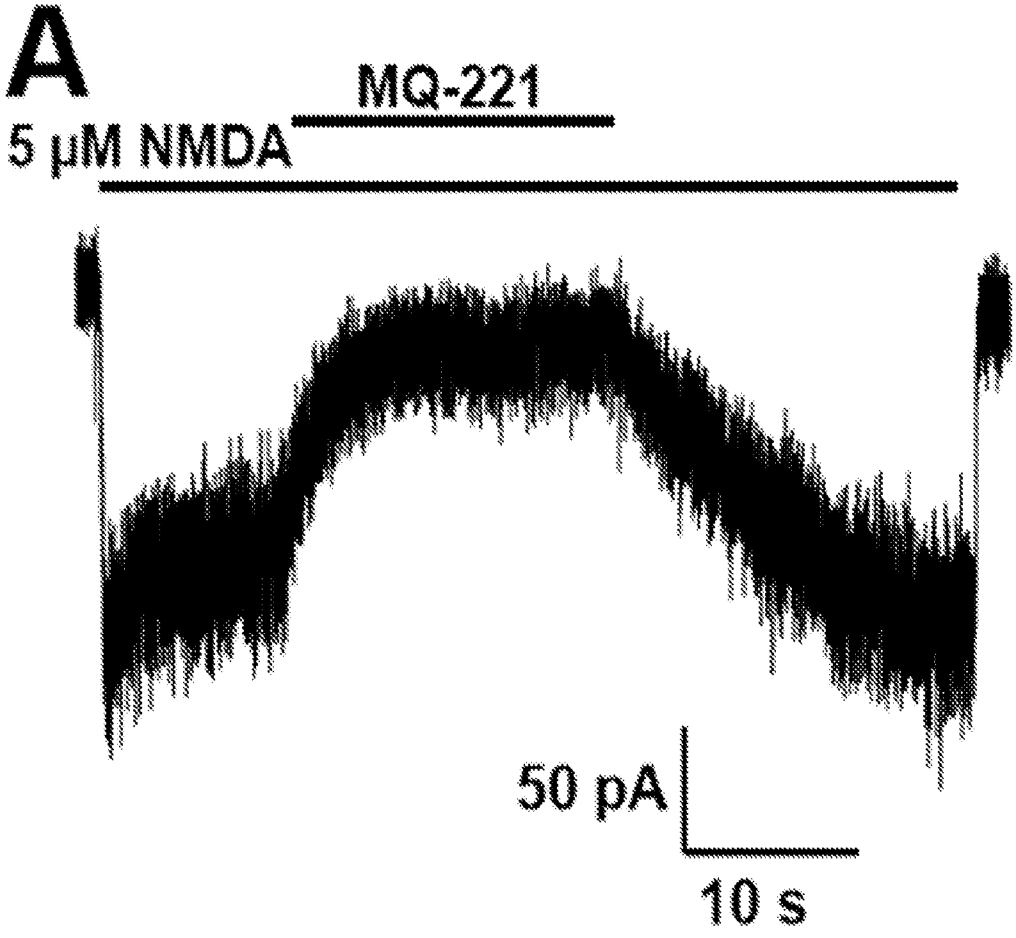
FIG. 7. Altering channel open probability alters MQ-221 kinetics but not steady-state inhibition. A, B, Example traces showing 2.5 μM MQ-221 inhibition of NMDA currents at 5
Figure 7:
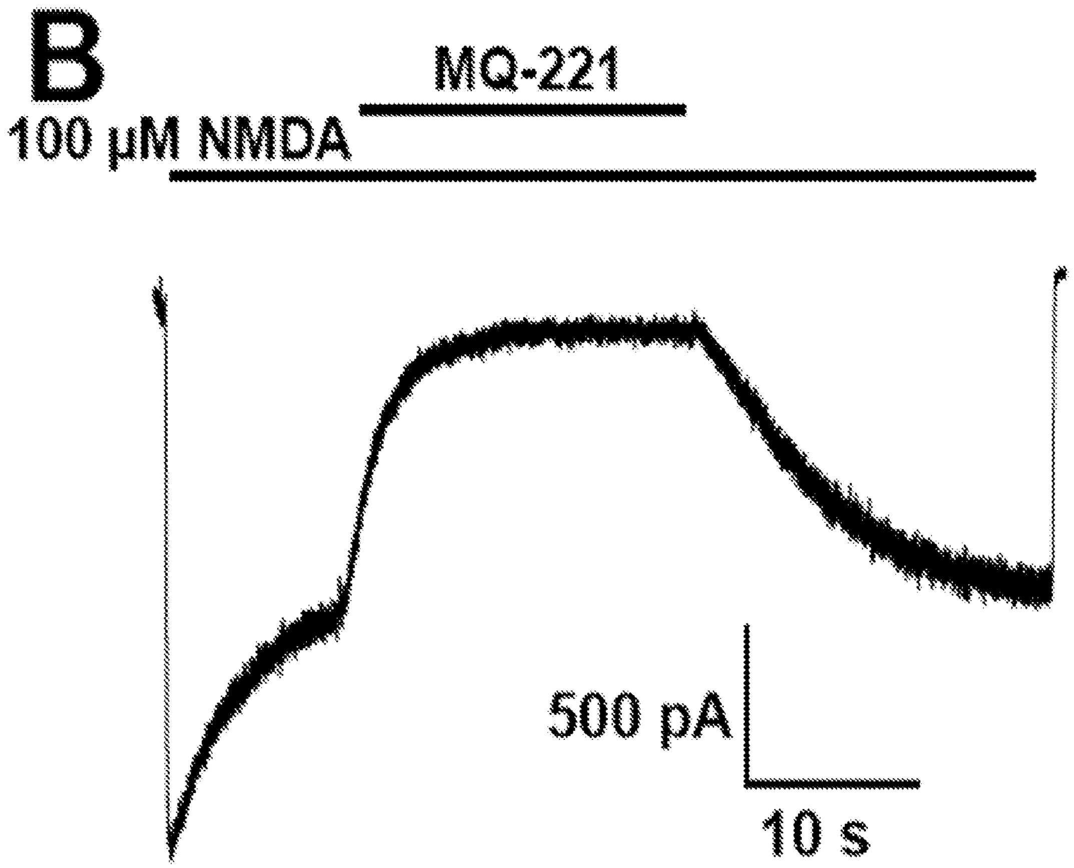
Figure 7:
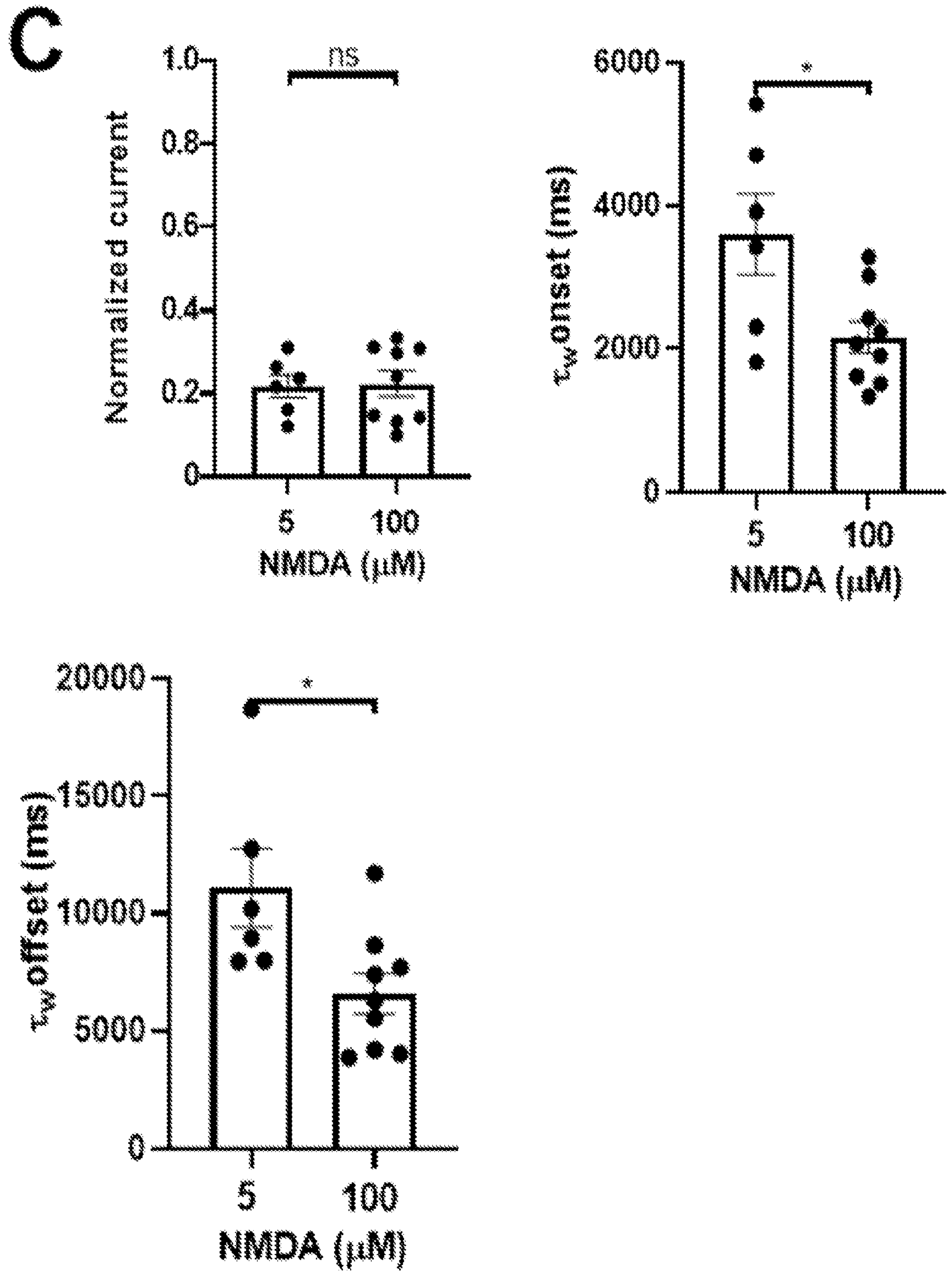
Figure 7:
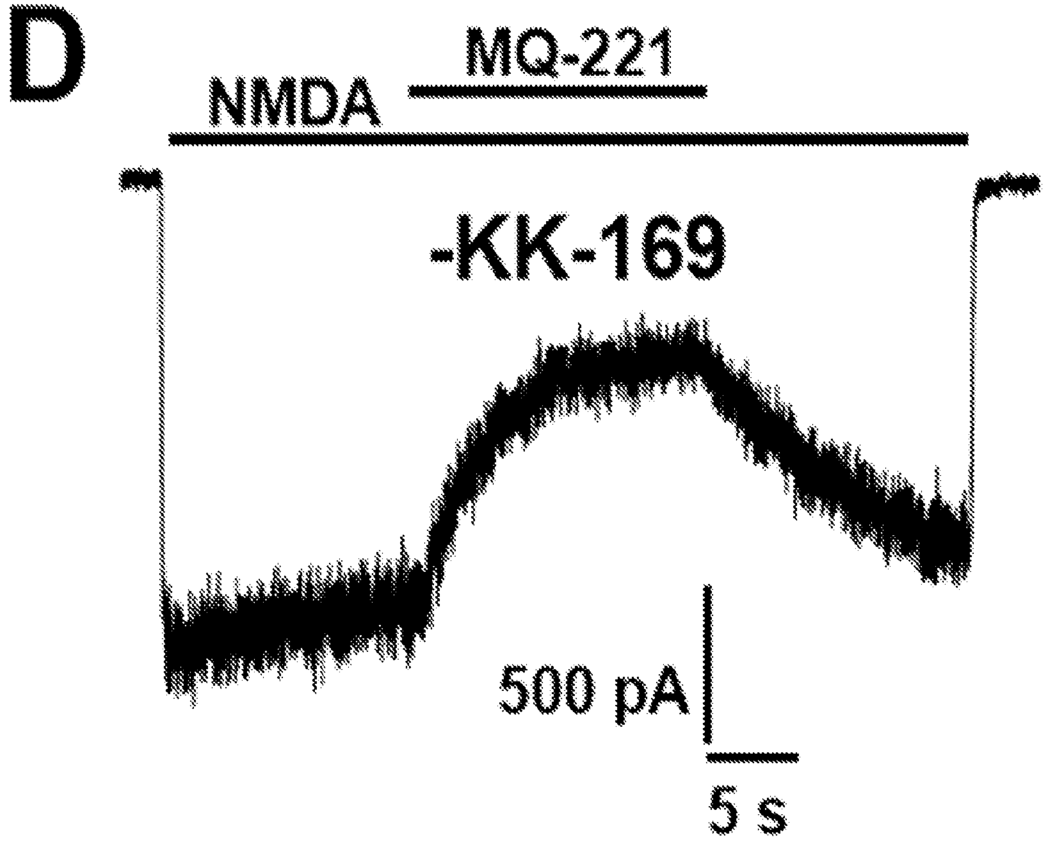
Figure 7:
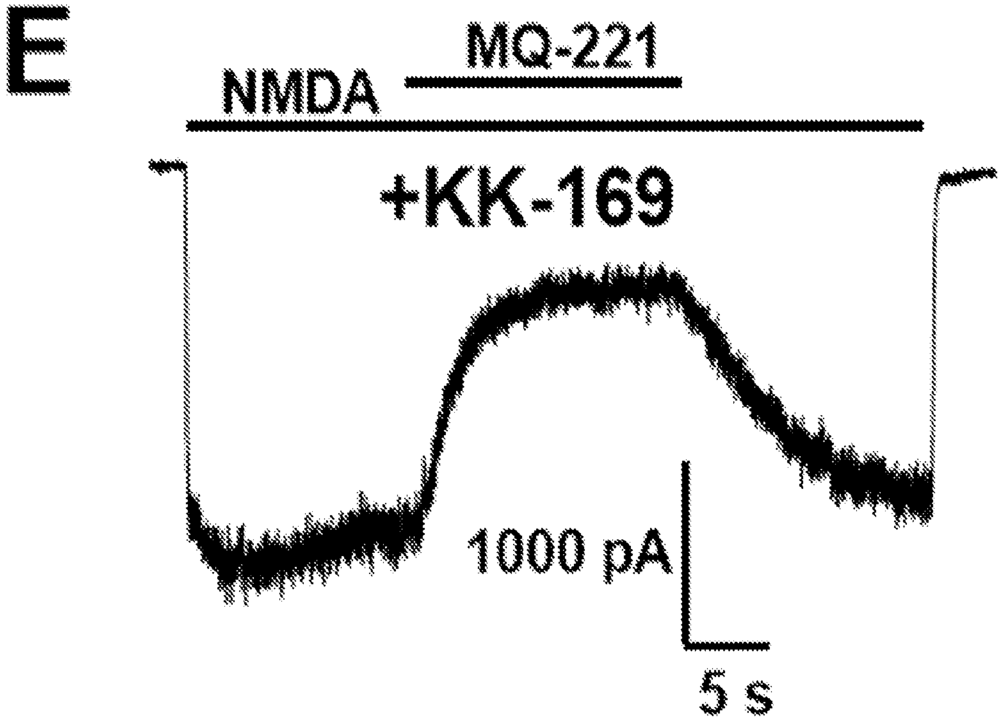
Figure 7:
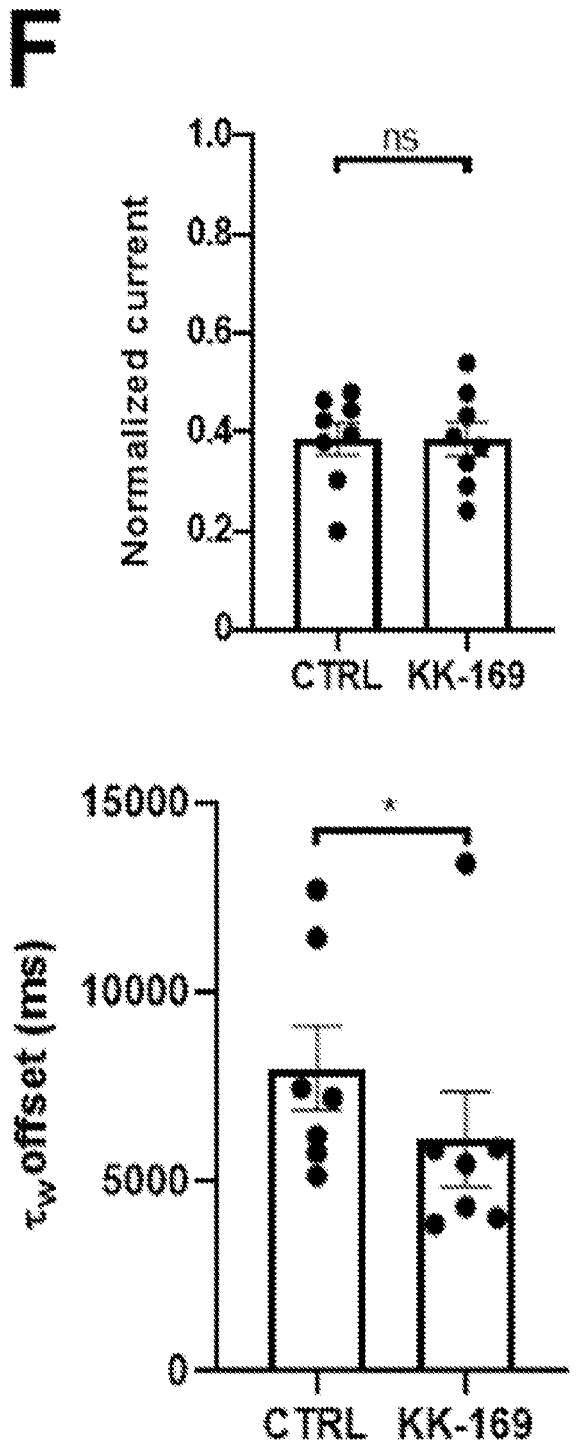

Other activation dependent inhibitors, such as ketamine and memantine, exhibit faster onset and offset kinetics as channel open probability is manipulated with positive allosteric modulators or with increased NMDA concentration (Emnett et al., 2015). Consistent with the other evidence for some activation dependence in the mechanism of MQ-221 (FIG. 7), both onset and offset weighted time constants were reduced by increasing NMDA concentration (FIG. 7, panels A-C). However, steady-state inhibition was unaffected by agonist concentration. To confirm these results, we used a strong NMDAR PAM that we have previously characterized, KK-169 (Chisari et al., 2019). As with increasing agonist concentration, co-application of KK-169 with NMDA and MQ-221 yielded faster MQ-221 onset (FIG. 7, panels D-F). Taken together, these results suggest that kinetics but not steady-state inhibition of MQ-221 are altered by channel open probability, consistent with some activation dependence of MQ-221 inhibition.

GluN2A versus GluN2B subtype-selective inhibitors of NMDARs are of interest for therapeutic purposes (Miller et al., 2014; Zanos and Gould, 2018). We tested subunit selectivity in native rat neuronal receptors by examining inhibition in the absence and presence of ifenprodil (10 μM), a selective inhibitor of NMDARs containing the GluN2B subunit. There appeared to be a modest reduction in MQ-221 sensitivity of cells challenged with MQ-221 in the presence of ifenprodil, suggesting that GluN2A-containing NMDARs may be less sensitive to MQ-221 (FIG. 8, panels A, B). We pursued this with a more definitive experiment that avoided combinatorial pharmacology by transfecting N2a cells with the obligatory GluN1a subunit and either GluN2A or GluN2B subunit. This experiment showed weaker sensitivity of GluN2A-containing NMDARs compared with GluN2B-containing receptors. We conclude that MQ-221 has subunit selectivity favoring GluN2B (FIG. 8, panels C-D).

Structure-Activity Characteristics

Given that MQ-221 seems unique in structure and in pharmacodynamics at $GABA_ARs$ and NMDARs, we examined several stereoisomers of MQ-221. We focused on carbon 3 and carbon 5 stereoisomers because stereochemistry at these positions is important for NMDAR and $GABA_AR$ activity of other steroid analogues (Covey et al., 2001; Weaver et al., 2000). Examination of the effect of the four resulting stereoisomers on NMDAR currents in hippocampal neurons showed that the 30 hydroxylation appeared important for inhibition of NMDAR function, and both 3a stereoisomers exhibited NMDAR potentiation (FIG. 9). To ascertain whether the other NMDAR inhibiting stereoisomer MQ-246 shared GABA-potentiating effects with MQ-221, we screened MQ-246 on GABA responses as in FIG. 1. In contrast to MQ-221, MQ-246 had only inhibiting effects on responses to 2 μM GABA (FIG. 9, panels C, D), even when evaluated at lower MQ-246 concentrations, at which potentiation might be more prominent (26±4% and 31±6% inhibition of peak GABA current at 1 μM and 3 μM MQ-246 respectively). We conclude that MQ-221 remains unique in its pharmacodynamic properties, rendering it an important compound.

Discussion

Neurosteroids and their analogues are emerging treatments for neuropsychiatric indications. The best understood targets of these compounds include $GABA_A$Rs and NMDARs. Historically, neurosteroids that alter NMDAR function are sulfated and universally inhibit $GABA_A$R function, potentially limiting usefulness. Here we describe a first-in-class compound, MQ-221, with a novel constellation of $GABA_A$R PAM and NMDAR NAM activities. Two existing classes of compounds, represented by ketamine and brexanolone (allopregnanolone) have utility for treating depressive disorders. We propose that MQ-221, by possessing the major actions of both ketamine and brexanolone, may represent a clinically fortuitous compound.

In addition to ketamine and brexanolone, acamprosate is a clinically used drug with $GABA_A$Rs and NMDARs as proposed targets. Acamprosate is FDA approved and modestly effective at treating alcohol use disorder (Kufahl et al., 2014). It may act at the same two receptor classes explored here and that are also responsible for acute actions of ethanol ($GABA_A$Rs and NMDARs) (Abrahao et al., 2017). By mimicking ethanol, acamprosate may ease withdrawal symptoms. However, acamprosate suffers from low potency at its receptor targets (Kufahl et al., 2014). The enhanced potency of MQ-221 over acamprosate suggests that, as with depression, alcohol use disorder may be an indication worthy of exploration for MQ-221-like compounds.

MQ-221 possesses several interesting characteristics, including the concentration range over which it engages targets. $GABA_A$R PAM neuroactive steroids (3β-hydroxy neurosteroids) typically are active in vitro in the high nanomolar to low micromolar range (Brown et al., 2002). Despite acting through a distinct mechanism from that of 3β-hydroxy neurosteroids, MQ-221 (a 3β-hydroxy neuroactive steroid) is an effective $GABA_A$R PAM at similar concentrations. Higher MQ-221 concentrations promote $GABA_A$R NAM effects in the late phase of prolonged GABA application (FIGS. 1 and 2). A NAM effect was not evident on IPSCs up to 2.5 μM, possibly because of the transient nature of IPSCs. In contrast to $GABA_A$R PAM neuroactive steroids, NMDAR NAM and PAM neuroactive steroids are sulfated at carbon 3 and typically active only above 10 μM (Horak et al., 2004; Park-Chung et al., 1997; but see Smith et al., 2014). A previous compound that we characterized, with overlapping effects to those of MQ-221, was limited by this low-potency at NMDARs (Mennerick et al., 2001). MQ-221 exhibits NAM activity in the low micromolar range, a similar concentration range as ketamine and in an overlapping range with $GABA_A$R PAM effects. This suggests that both targets are likely to be engaged by a single dose of MQ-221.

Among pharmacodynamic effects on NMDARs is the weak use dependence of MQ-221 compared with pregnanolone sulfate (FIG. 5). Ketamine also exhibits activation dependent block of NMDARs (MacDonald et al., 1987). It is unclear whether activation dependence is a requisite of antidepressant activity, since some experimental NMDAR antagonists without activation dependent properties are also of interest as antidepressants (Miller et al., 2014; Williams and Schatzberg, 2016; Zorumski et al., 2016).

Another pharmacodynamic effect of MQ-221 that may aid or may complicate clinical utility is the $GABA_A$R NAM activity observed at high concentrations and with strong $GABA_A$R activation. As noted above, this effect was not evident during spontaneous synaptic activity in cultures of hippocampal neurons. However, we cannot exclude the possibility that NAM effects might be relevant under certain physiological conditions in vivo. The NAM effect might self-limit $GABA_A$R PAM actions and prevent sedation and other side effects of $GABA_A$R PAMs at high concentrations. On the other hand, this feature may be a liability of MQ-221 by promoting convulsant activity observed with other $GABA_A$R NAMs such as picrotoxin (Baker et al., 1965). The hope is that the concentration separation between PAM and NAM activity would limit negative consequences.

We found that MQ-221 preferred GluN2B-containing NMDARs. This effect was not as apparent in native rat hippocampal neurons as it was with recombinant rat NMDAR subunits transfected into N2a cells (FIG. 8). Reasons for the differing results could include incomplete ifenprodil block, native tri-heteromeric receptors, or post-translational differences that modulate pharmacological properties. GluN2B selectivity could aid clinical benefit, as GluN2B preferring drugs have been associated with antidepressant effects (Miller et al., 2014; Zanos and Gould, 2018) and neuroprotection (Hardingham and Bading, 2010).

Finally, we considered structural features of MQ-221 that might account for the unusual dual $GABA_A$R/NMDAR actions of the compound. MQ-221 might be considered a hybrid between neurosteroids and oxysterols. Oxysterols are direct oxidation products of cholesterol. Compounds in this class oxidized on the cholesterol side chain can have effects on NMDARs, including PAM or NAM activity (Hu et al., 2014; Linsenbardt et al., 2014; Paul et al., 2013). NMDAR NAM activity may derive from the oxysterol-like structure rather than a neurosteroid-like structure. To date, oxysterols are not known to have effects on $GABA_A$Rs. Among possible additional structural manipulations of MQ-221, altering the side chain length is a straightforward change that could improve on the activity of MQ-221.

Bile acids are another class of cholesterol derivative with effects on $GABA_A$Rs and NMDARs (Mennerick et al., 2001; Schubring et al., 2012). Bile acids, like MQ-221, have a negatively charged side chain. However, the major bile acids are 5β-reduced, while MQ-221 is 5α-reduced. Our structural modifications showed that conversion to the 5β stereoisomer of MQ-221 retained NMDAR effects but sacrificed $GABA_A$R PAM activity in favor of NAM activity (FIG. 8), as predicted from previous work with bile acids. The stereochemistry of the 3-hydroxyl group was important for converting NMDAR NAM effects to NMDAR PAM effects and for enhancing $GABA_A$R NAM actions (FIG. 9). It seems clear that retaining the 3β-stereochemistry for the hydroxyl group is important for MQ-221 analogues with further enhanced activity. The nature of the $GABA_A$R PAM mechanisms for MQ-221 remains unclear since we have found previously that 3β-hydroxy neurosteroids are weak activation-dependent $GABA_A$R NAMS rather than PAMs (Wang et al., 2002), and a mutation that eliminates potentiation by allopregnanolone failed to reduce MQ-221 potentiation (FIG. 4).

REFERENCES

Abdallah, C. G., Sanacora, G., Duman, R. S., Krystal, J. H., 2018. The neurobiology of depression, ketamine and rapid-acting antidepressants: Is it glutamate inhibition or activation? Pharmacol. Ther. 190, 148-158.

Abrahao, K. P., Salinas, A. G., Lovinger, D. M., 2017. Alcohol and the Brain: Neuronal Molecular Targets, Synapses, and Circuits. Neuron 96, 1223-1238.

Baker, W. W., Kratky, M., Benedict, F., 1965. Electrographic responses to intrahippocampal injections of convulsant drugs. Exp. Neurol. 12, 136-145.

Belelli, D., Hogenkamp, D., Gee, K. W., Lambert, J. J., 2020. Realising the therapeutic potential of neuroactive steroid modulators of the $GABA_A$ receptor. Neurobiol. Stress 12, 100207.

Brown, N., Kerby, J., Bonnert, T. P., Whiting, P. J., Wafford, K. A., 2002. Pharmacological characterization of a novel cell line expressing human α4β3δ $GABA_A$ receptors. Br J Pharmacol 136, 965-974.

Chisari, M., Shu, H.-J., Taylor, A., Steinbach, J., Zorumski, C., Mennerick, S., 2010. Structurally diverse amphiphiles exhibit biphasic modulation of $GABA_A$ receptors: similarities and differences with neurosteroid actions. Br. J. Pharmacol. 160, 130-141.

Chisari, M., Wilding, T. J., Brunwasser, S., Krishnan, K., Qian, M., Benz, A., Huettner, J. E., Zorumski, C. F., Covey, D. F., Mennerick, S., 2019. Visualizing pregnenolone sulfate-like modulators of NMDA receptor function reveals intracellular and plasma-membrane localization. Neuropharmacology 144, 91-103.

Covey, D. F. F., Evers, A. S. S., Mennerick, S., Zorumski, C. F. F., Purdy, R. H. H., 2001. Recent developments in structure-activity relationships for steroid modulators of $GABA_A$ receptors. Brain Res. Rev. 37.

Duman, R. S., Shinohara, R., Fogaça, M. V., Hare, B., 2019. Neurobiology of rapid-acting antidepressants: convergent effects on GluA1-synaptic function. Mol. Psychiatry.

Eisenman, L. N., He, Y., Fields, C., Zorumski, C. F., Mennerick, S., 2003. Activation-dependent properties of pregnenolone sulfate inhibition of $GABA_A$ receptor-mediated current. J. Physiol. 550.

Emnett, C. M., Eisenman, L. N., Mohan, J., Taylor, A. A., Doherty, J. J., Paul, S. M., Zorumski, C. F., Mennerick, S., 2015. Interaction between positive allosteric modulators and trapping blockers of the NMDA receptor channel. Br. J. Pharmacol. 172.

Gunduz-Bruce, H., Silber, C., Kaul, I., Rothschild, A. J., Riesenberg, R., Sankoh, A. J., Li, H., Lasser, R., Zorumski, C. F., Rubinow, D. R., Paul, S. M., Jonas, J., Doherty, J. J., Kanes, S. J., 2019. Trial of SAGE-217 in patients with major depressive disorder. N. Engl. J. Med. 381, 903-911.

Hardingham, G. E., Bading, H., 2010. Synaptic versus extrasynaptic NMDA receptor signalling: implications for neurodegenerative disorders. Nat Rev Neurosci 11, 682-696.

Harrison, N. L., Vicini, S., Barker, J. L., 1987. A steroid anesthetic prolongs inhibitory postsynaptic currents in cultured rat hippocampal neurons. J. Neurosci. 7, 604-9.

Horak, M., Vlcek, K., Chodounska, H., Vyklicky Jr., L., 2006. Subtype-dependence of N-methyl-D-aspartate receptor modulation by pregnenolone sulfate. Neuroscience 137, 93-102.

Horak, M., Vlcek, K., Petrovic, M., Chodounska, H., Vyklicky Jr., L., 2004. Molecular mechanism of pregnenolone sulfate action at NR1/NR2B receptors. J. Neurosci. 24, 10318-10325.

Hosie, A. M., Wilkins, M. E., da Silva, H. M. A., Smart, T. G., 2006. Endogenous neurosteroids regulate $GABA_A$ receptors via two discrete transmembrane sites. Nature 444, 486-489.

Hosie, A. M., Wilkins, M. E., Smart, T. G., 2007. Neurosteroid binding sites on GABA(A) receptors. Pharmacology Ther. 116, 7-19.

Hu, H., Zhou, Y., Leng, T., Liu, A., Wang, Y., You, X., Chen, J., Tang, L., Chen, W., Qiu, P., Yin, W., Huang, Y., Zhang, J., Wang, L., Sang, H., Yan, G., 2014. The major cholesterol metabolite cholestane-3beta,5alpha,6beta-triol functions as an endogenous neuroprotectant. J. Neurosci. 34, 11426-11438.

Johnson, J. W., Glasgow, N. G., Povysheva, N. V, 2014. Recent insights into the mode of action of memantine and ketamine. Curr Opin Pharmacol 20C, 54-63.

Kanes, S., Colquhoun, H., Gunduz-Bruce, H., Raines, S., Arnold, R., Schacterle, A., Doherty, J., Epperson, C. N., Deligiannidis, K. M., Riesenberg, R., Hoffmann, E., Rubinow, D., Jonas, J., Paul, S., Meltzer-Brody, S., 2017. Brexanolone (SAGE-547 injection) in post-partum depression: a randomised controlled trial. Lancet 390, 480-489.

Korinek, M., Kapras, V., Vyklicky, V., Adamusova, E., Borovska, J., Vales, K., Stuchlik, A., Horak, M., Chodounska, H., Vyklicky Jr., L., 2011. Neurosteroid modulation of N-methyl-D-aspartate receptors: molecular mechanism and behavioral effects. Steroids 76, 1409-1418.

Kufahl, P. R., Watterson, L. R., Olive, M. F., 2014. The development of acamprosate as a treatment against alcohol relapse. Expert Opin. Drug Discov. 9, 1355-1369.

Linsenbardt, A. J., Taylor, A., Emnett, C. M., Doherty, J. J., Krishnan, K., Covey, D. F., Paul, S. M., Zorumski, C. F., Mennerick, S., 2014. Different oxysterols have opposing actions at N-methyl-D-aspartate receptors. Neuropharmacology 85.

MacDonald, J. F., Miljkovic, Z., Pennefather, P., 1987. Use-dependent block of excitatory amino acid currents in cultured neurons by ketamine. J. Neurophysiol. 58, 251-266.

Malayev, A., Gibbs, T. T., Farb, D. H., 2002. Inhibition of the NMDA response by pregnenolone sulphate reveals subtype selective modulation of NMDA receptors by sulphated steroids. Br J Pharmacol 135, 901-909.

Meltzer-Brody, S., Colquhoun, H., Riesenberg, R., Epperson, C. N., Deligiannidis, K. M., Rubinow, D. R., Li, H., Sankoh, A. J., Clemson, C., Schacterle, A., Jonas, J., Kanes, S., 2018. Brexanolone injection in post-partum depression: two multicentre, double-blind, randomised, placebo-controlled, phase 3 trials. Lancet 392, 1058-1070.

Meltzer-Brody, S., Kanes, S. J., 2020. Allopregnanolone in postpartum depression: Role in pathophysiology and treatment. Neurobiol. Stress.

Mennerick, S., Zeng, C.-M., Benz, A., Shen, W., Izumi, Y., Evers, A. S., Covey, D. F., Zorumski, C. F., 2001. Effects on γ-aminobutyric acid GABAA receptors of a neuroactive steroid that negatively modulates glutamate neurotransmission and augments GABA neurotransmission. Mol. Pharmacol. 60, 732-741.

Miller, O. H., Yang, L., Wang, C.-C., Hargroder, E. A., Zhang, Y., Delpire, E., Hall, B. J., 2014. GluN2B-containing NMDA receptors regulate depression-like behavior and are critical for the rapid antidepressant actions of ketamine. Elife 3.

Nilsson, K. R., Zorumski, C. F., Covey, D. F., 1998. Neurosteroid analogues. 6. The synthesis and $GABA_A$ receptor pharmacology of enantiomers of dehydroepiandrosterone sulfate, pregnenolone sulfate, and (3a, 5b)-3-hydroxypregnan-20-one sulfate. J Med Chem 41, 2604-2613.

Park-Chung, M., Wu, F. S., Purdy, R. H., Malayev, A. A., Gibbs, T. T., Farb, D. H., 1997. Distinct sites for inverse modulation of N-methyl-D-aspartate receptors by sulfated steroids. Mol. Pharmacol. 52, 1113-1123.

Parsons, C. G., Gruner, R., Rozental, J., Millar, J., Lodge, D., 1993. Patch clamp studies on the kinetics and selectivity of N-methyl-D-aspartate receptor antagonism by memantine (1-amino-3,5-dimethyladamantan). Neuropharmacology 32, 1337-1350.

Paul, S. M., Doherty, J. J., Robichaud, A. J., Belfort, G. M., Chow, B. Y., Hammond, R. S., Crawford, D. C., Linsenbardt, A. J., Shu, H.-J., Izumi, Y., Mennerick, S. J., Zorumski, C. F., 2013. The major brain cholesterol metabolite 24(S)-hydroxycholesterol is a potent allosteric modulator of N-Methyl-D-Aspartate receptors. J. Neurosci. 33.

Petrovic, M., Sedlacek, M., Horak, M., Chodounska, H., Vyklickf, L., 2005. 20-Oxo-5β-pregnan-3α:-yl sulfate is a use-dependent NMDA receptor inhibitor. J. Neurosci. 25, 8439-8450.

Schubring, S. R., Fleischer, W., Lin, J. S., Haas, H. L., Sergeeva, O. A., 2012. The bile steroid chenodeoxycholate is a potent antagonist at NMDA and GABA A receptors. Neurosci. Lett. 506, 322-326.

Smith, C. C., Martin, S. C., Sugunan, K., Russek, S. J., Gibbs, T. T., Farb, D. H., 2014. A role for picomolar concentrations of pregnenolone sulfate in synaptic activity-dependent $Ca^{2+}$ signaling and CREB activation. Mol Pharmacol 86, 390-398.

Wang, M., He, Y., Eisenman, L. N., Fields, C., Zeng, C.-M., Mathews, J., Benz, A., Fu, T., Zorumski, E., Steinbach, J. H., Covey, D. F., Zorumski, C. F., Mennerick, S., 2002. 3β-Hydroxypregnane steroids are pregnenolone sulfate-like $GABA_A$ receptor antagonists. J. Neurosci. 22, 3366-3375.

Weaver, C. E., Land, M. B., Purdy, R. H., Richards, K. G., Gibbs, T. T., Farb, D. H., 2000. Geometry and charge determine pharmacological effects of steroids on N-methyl-D-aspartate receptor-induced Ca(2+) accumulation and cell death. J. Pharmacol. Exp. Ther. 293, 747-754.

Williams, N. R., Schatzberg, A. F., 2016. NMDA antagonist treatment of depression. Curr. Opin. Neurobiol.

Zanos, P., Gould, T. D., 2018. Mechanisms of ketamine action as an antidepressant. Mol. Psychiatry 23, 801-811.

Zorumski, C. F., Izumi, Y., Mennerick, S., 2016. Ketamine: NMDA receptors and beyond. J. Neurosci. 36.

The invention claimed is:

1. A compound having a structure selected from the group consisting of:

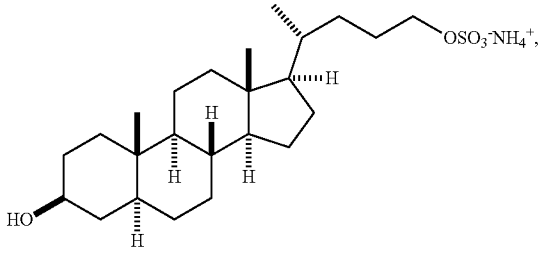

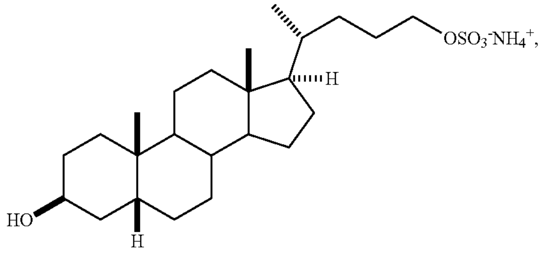

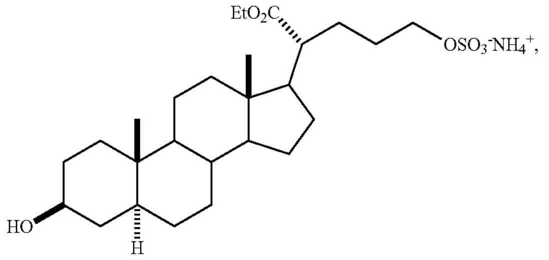

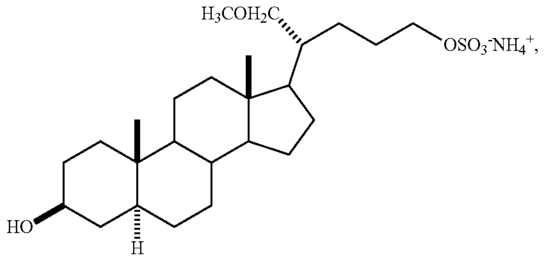

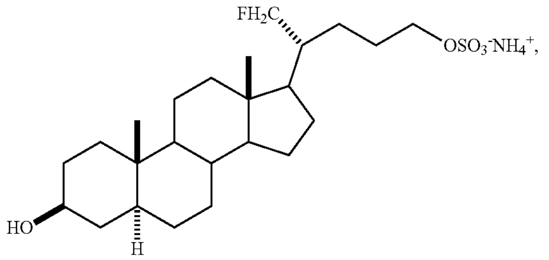

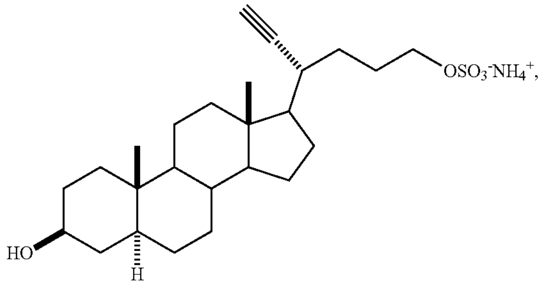

-continued

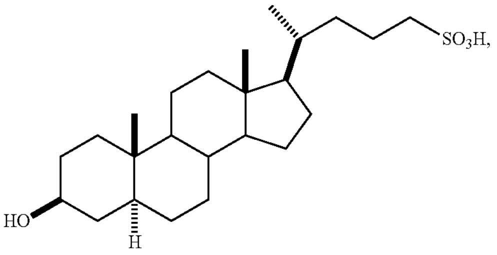

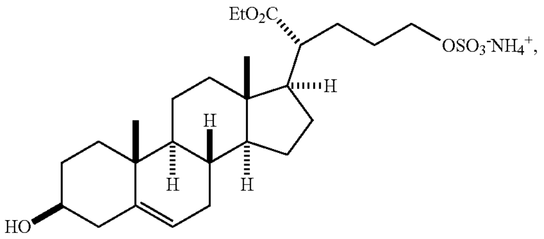

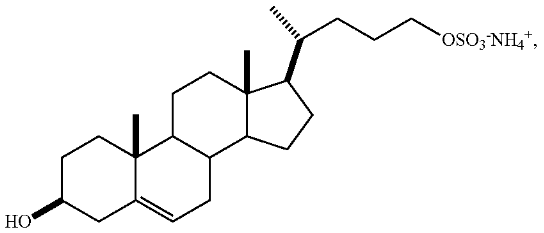

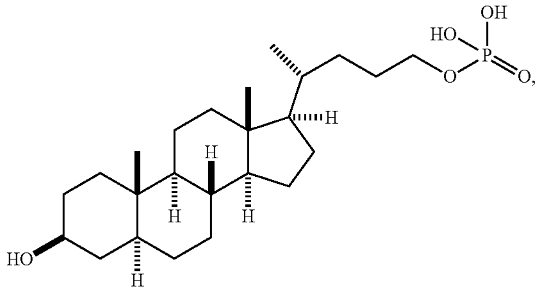

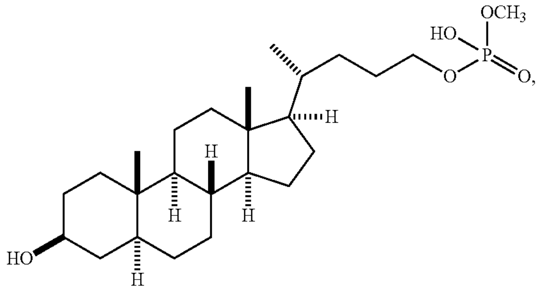

and pharmaceutically acceptable salts thereof.

2. The compound of claim 1, wherein the compound has a structure of:

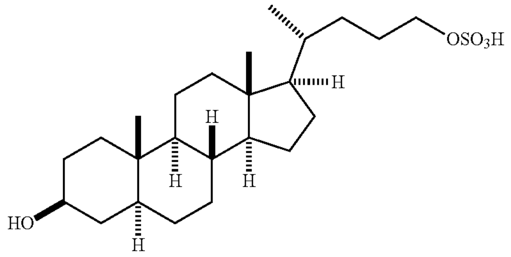

or a pharmaceutically acceptable salt thereof.

3. The compound of claim 1, wherein the compound has a structure of:

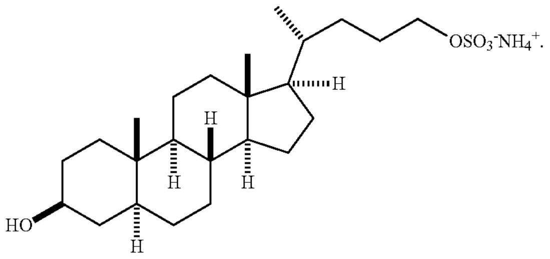

4. A method of inhibiting N-methyl-d-aspartate receptors (NMDAR) and/or potentiating γ-aminobutyric acid receptors ($GABA_AR$) comprising administering to a subject a composition comprising a compound of claim 1.

5. The method of claim 4, wherein the method is for treating a psychiatric disease, disorder, or condition in a subject in need thereof.

6. A method of treating alcohol use disorder in a subject in need thereof comprising administering to the subject a composition comprising an effective amount of a compound of claim 1.

7. A method of treating alcohol use disorder in a subject in need thereof comprising administering to the subject a composition comprising an effective amount of a compound of the following structure:

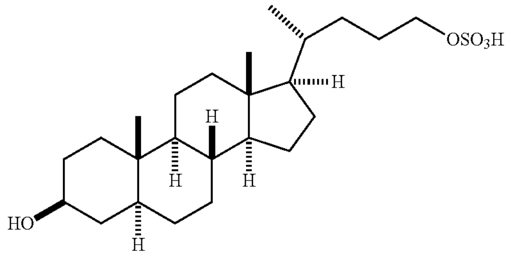

or pharmaceutically acceptable salt thereof.

* * * * *